(12) United States Patent
Raymond et al.

(10) Patent No.: US 7,476,240 B2
(45) Date of Patent: Jan. 13, 2009

(54) DEVICES AND METHODS FOR INSERTING A SPINAL FIXATION ELEMENT

(75) Inventors: Douglas Raymond, Randolph, MA (US); James Roveda, Boston, MA (US); Brian Murphy, Quincy, MA (US); Christopher Sicvol, Boston, MA (US); Sean Selover, Westport, MA (US); Erasmo Lopez, Abington, MA (US); Ramon Ruberte, Ann Arbor, MA (US); Bryan S. Jones, West Roxbury, MA (US); Christopher Ramsay, West Wareham, MA (US)

(73) Assignee: Depuy Spine, Inc., Raynham, MA (US)

( * ) Notice: Subject to any disclaimer, the term of this patent is extended or adjusted under 35 U.S.C. 154(b) by 177 days.

(21) Appl. No.: 11/051,983

(22) Filed: Feb. 3, 2005

(65) Prior Publication Data

US 2005/0192589 A1 Sep. 1, 2005

Related U.S. Application Data

(60) Provisional application No. 60/542,548, filed on Feb. 6, 2004, provisional application No. 60/565,784, filed on Apr. 27, 2004.

(51) Int. Cl.
*A61B 17/88* (2006.01)
(52) U.S. Cl. .......................... 606/279; 606/99
(58) Field of Classification Search ............. 606/60–61, 606/99, 246, 250–262, 264–279, 96, 104, 606/323, 198, 914, 916, 86 A
See application file for complete search history.

(56) References Cited

U.S. PATENT DOCUMENTS

| | | | |
|---|---|---|---|
| 4,913,134 A | 4/1990 | Lugue | |
| 5,242,446 A | 9/1993 | Steffee | |
| 5,984,923 A | 11/1999 | Breard | |
| 6,235,028 B1 | 5/2001 | Brumfield | |
| 6,458,491 B1 | 10/2002 | Wimberly | |
| 6,530,929 B1 | 3/2003 | Justis | |
| 6,540,749 B2 | 4/2003 | Schafer | |
| 6,554,831 B1 | 4/2003 | Rivard | |
| 6,652,527 B2 | 11/2003 | Zucherman | |
| 7,008,422 B2 | 3/2006 | Foley | |
| 2002/0116000 A1 | 8/2002 | Zucherman | |

(Continued)

FOREIGN PATENT DOCUMENTS

DE 3434807 12/1985

(Continued)

*Primary Examiner*—Eduardo C Robert
*Assistant Examiner*—James L Swiger, III

(57) ABSTRACT

A method for introducing a spinal fixation element between two bone anchors includes engaging a spinal fixation element to a shaft of an instrument, positioning the shaft of the instrument through a sidewall opening of a first percutaneous access device connected to a first bone anchor and through a side wall opening of a second percutaneous access device connected to a second bone anchor, the spinal fixation element extending in an orientation substantially parallel to the longitudinal axis of at least one of the first percutaneous access device and the second percutaneous access device, and pivoting the instrument to change the orientation of the spinal fixation element and position the spinal fixation element in proximity to the first bone anchor and in proximity to the second bone anchor.

12 Claims, 58 Drawing Sheets

U.S. PATENT DOCUMENTS

| | | |
|---|---|---|
| 2002/0138077 A1 | 9/2002 | Ferree |
| 2002/0169448 A1 | 11/2002 | Vanacker |
| 2003/0083657 A1 | 5/2003 | Drewry |
| 2003/0208203 A1 | 11/2003 | Lim |
| 2003/0229347 A1 | 12/2003 | Sherman |
| 2004/0138662 A1 | 7/2004 | Landry |
| 2004/0143265 A1 | 7/2004 | Landry |
| 2005/0065516 A1 | 3/2005 | Jahng |
| 2005/0085813 A1 | 4/2005 | Spitler |
| 2005/0090824 A1 | 4/2005 | Schluzas |
| 2005/0131408 A1 | 6/2005 | Sicvol |
| 2005/0131419 A1 | 6/2005 | McCord |
| 2005/0131420 A1 | 6/2005 | Techiera |
| 2005/0131421 A1 * | 6/2005 | Anderson et al. ............. 606/99 |
| 2005/0131422 A1 | 6/2005 | Anderson |
| 2005/0192570 A1 | 9/2005 | Jackson |
| 2005/0192579 A1 | 9/2005 | Jackson |
| 2006/0030839 A1 | 2/2006 | Park |
| 2006/0036244 A1 | 2/2006 | Spitler |
| 2006/0036255 A1 | 2/2006 | Pond |
| 2006/0074445 A1 | 4/2006 | Gerber |
| 2006/0079894 A1 | 4/2006 | Colleran |
| 2006/0084993 A1 | 4/2006 | Landry |
| 2006/0095035 A1 | 5/2006 | Jones |
| 2006/0106380 A1 | 5/2006 | Colleran |
| 2006/0111712 A1 | 5/2006 | Jackson |
| 2006/0111713 A1 | 5/2006 | Jackson |
| 2006/0111714 A1 | 5/2006 | Foley |
| 2006/0122597 A1 | 6/2006 | Jones |
| 2006/0142761 A1 | 6/2006 | Landry |
| 2006/0149237 A1 | 7/2006 | Markworth |

FOREIGN PATENT DOCUMENTS

| | | |
|---|---|---|
| WO | 0128436 | 4/2001 |
| WO | 2004041100 | 5/2004 |

* cited by examiner

FIG. 5A
FIG. 5B
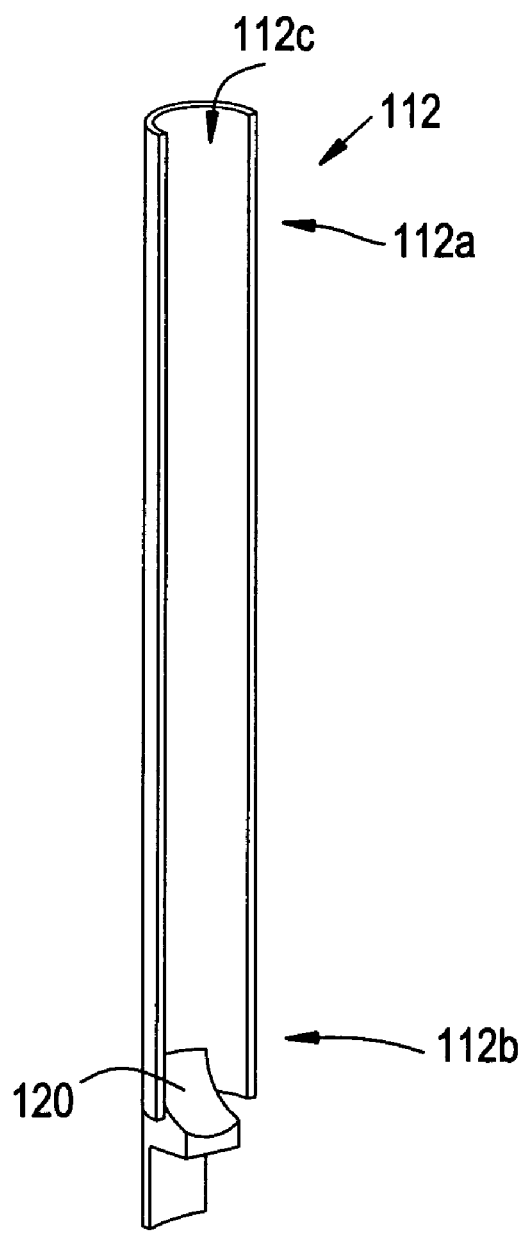
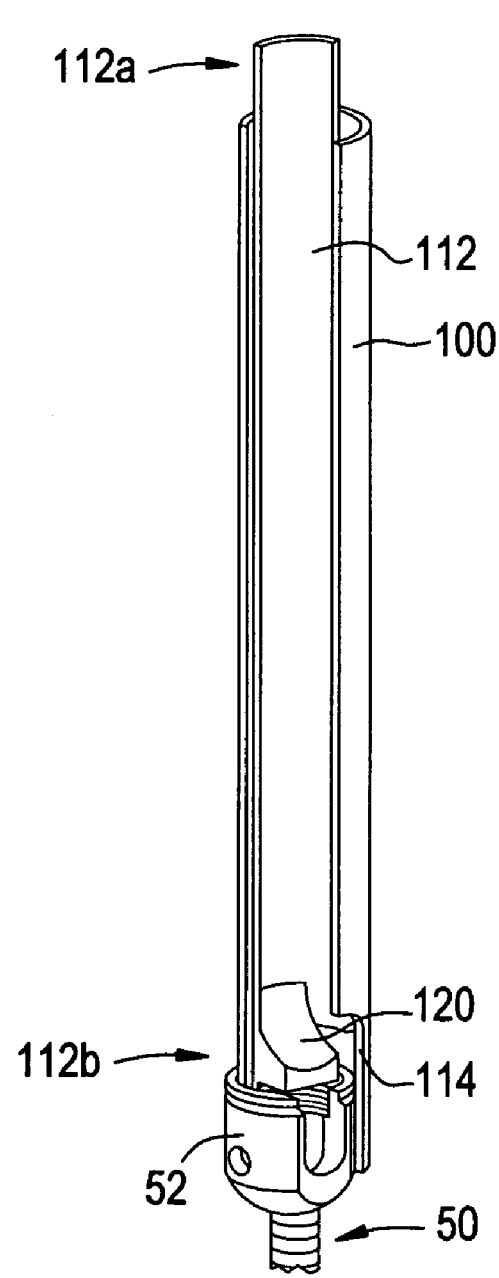

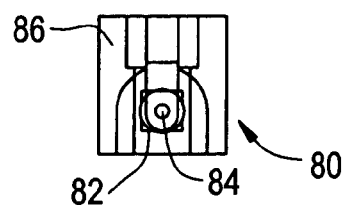
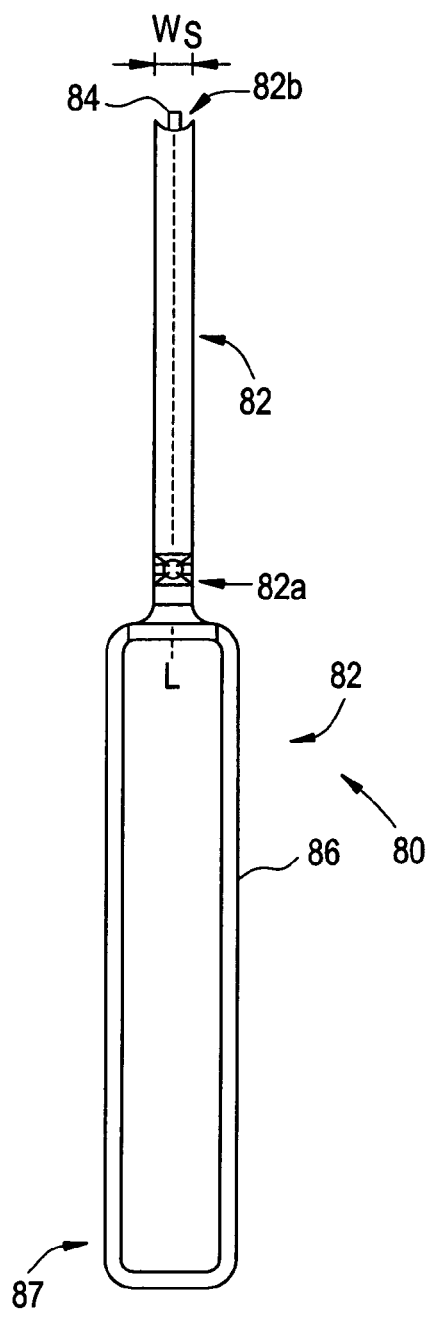
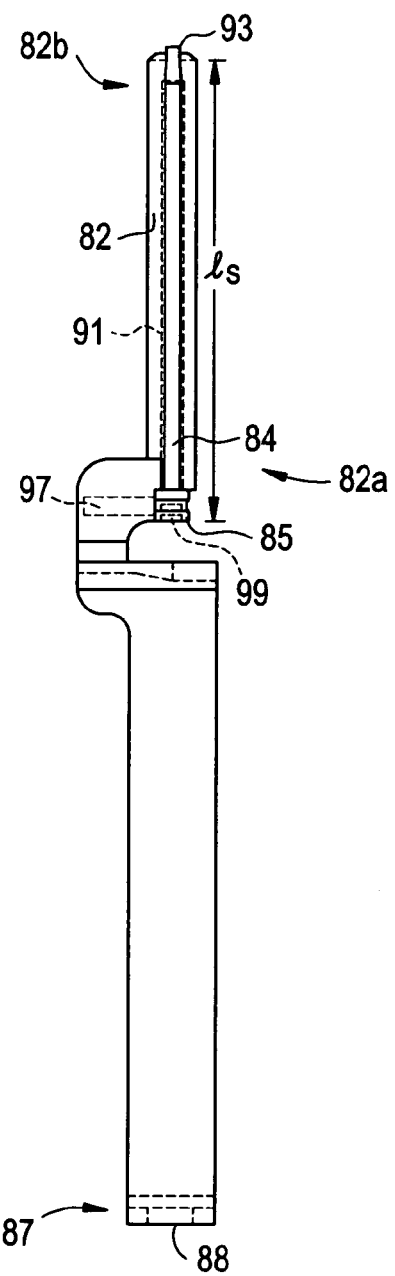

FIG. 8A
FIG. 8B
FIG. 8C
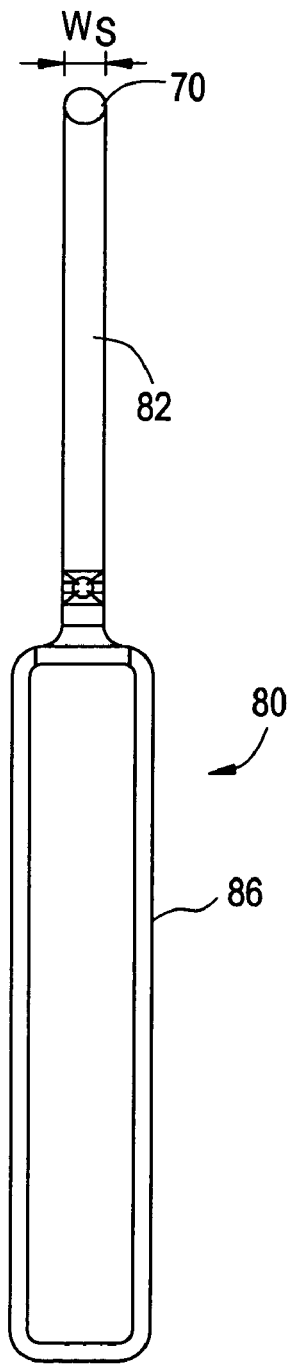
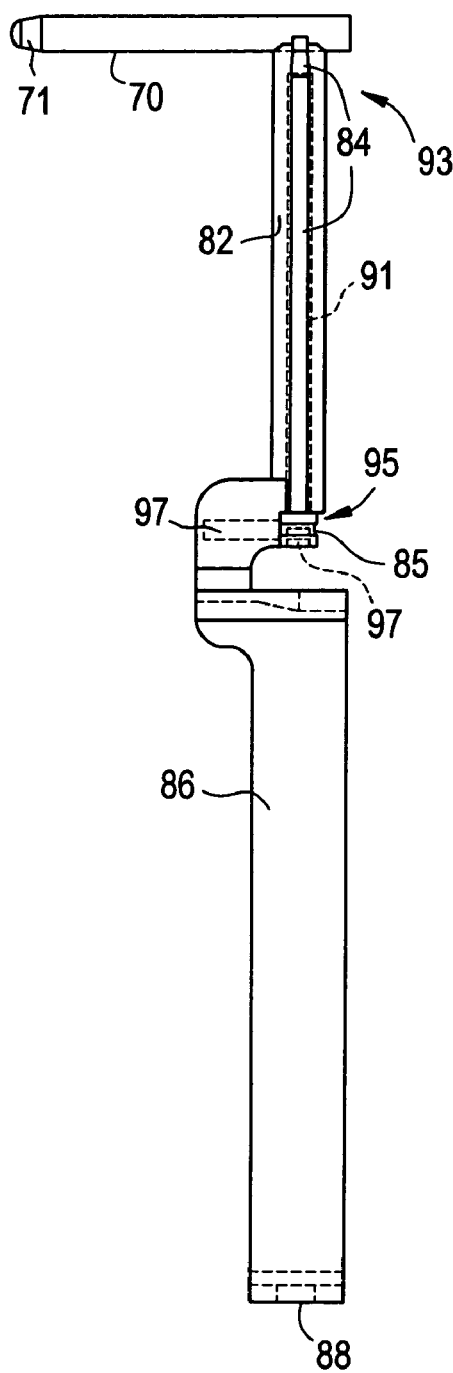
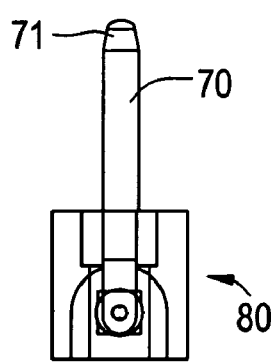

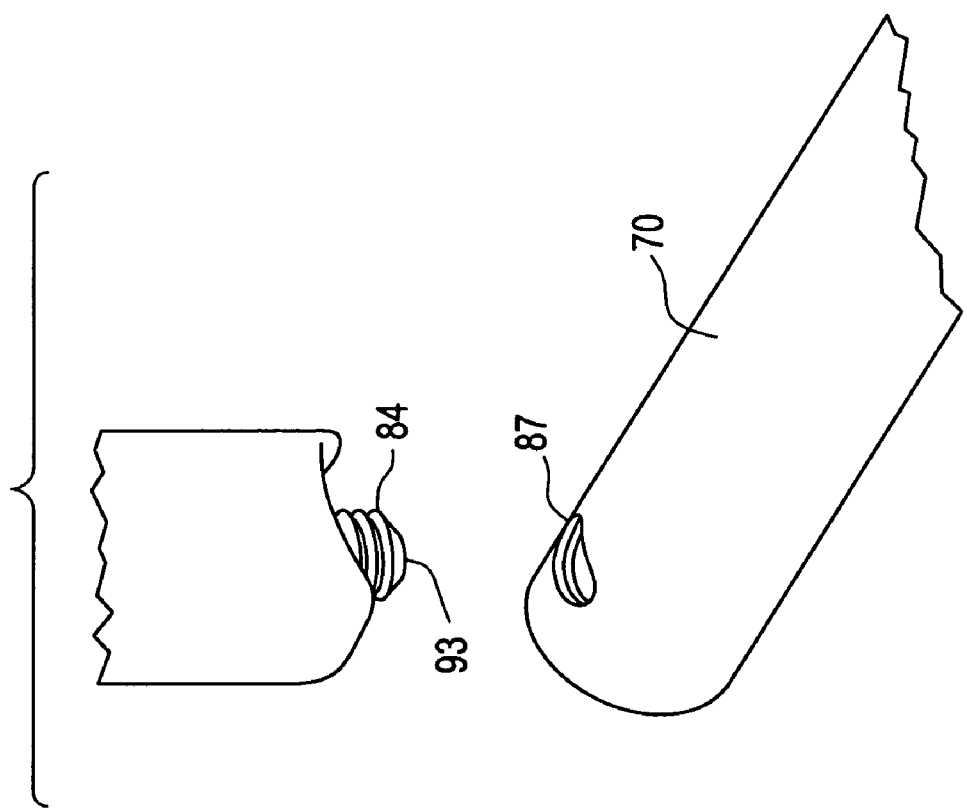

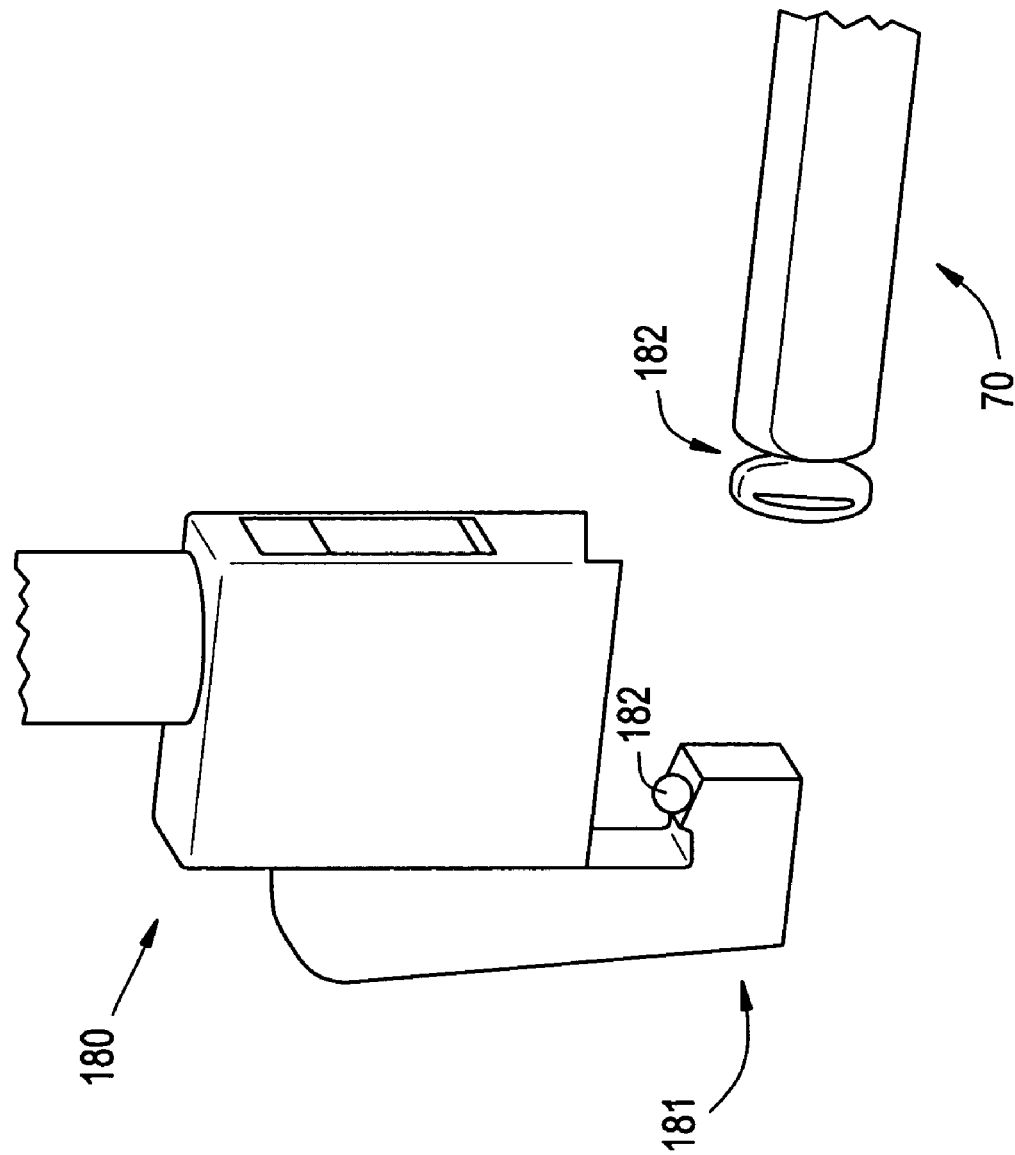

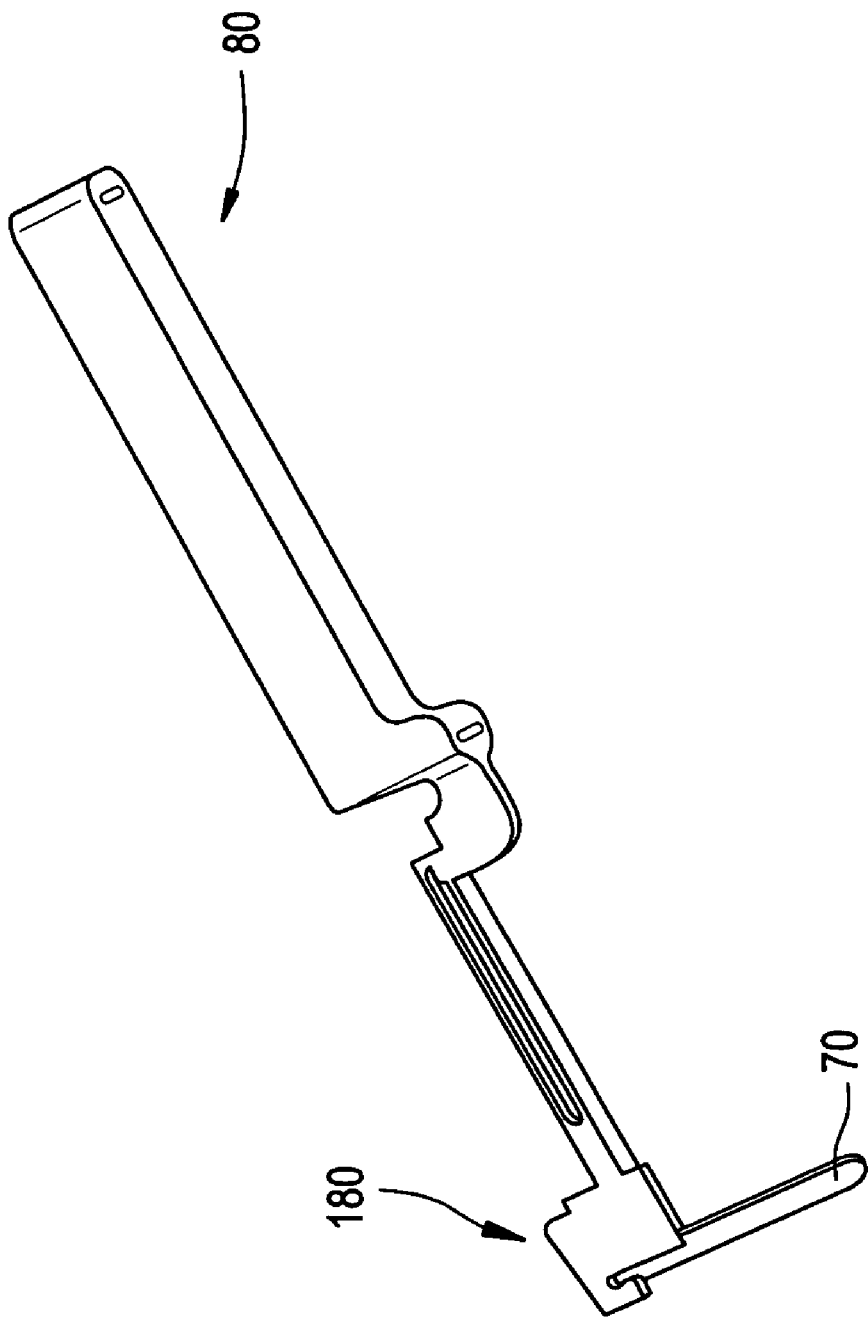

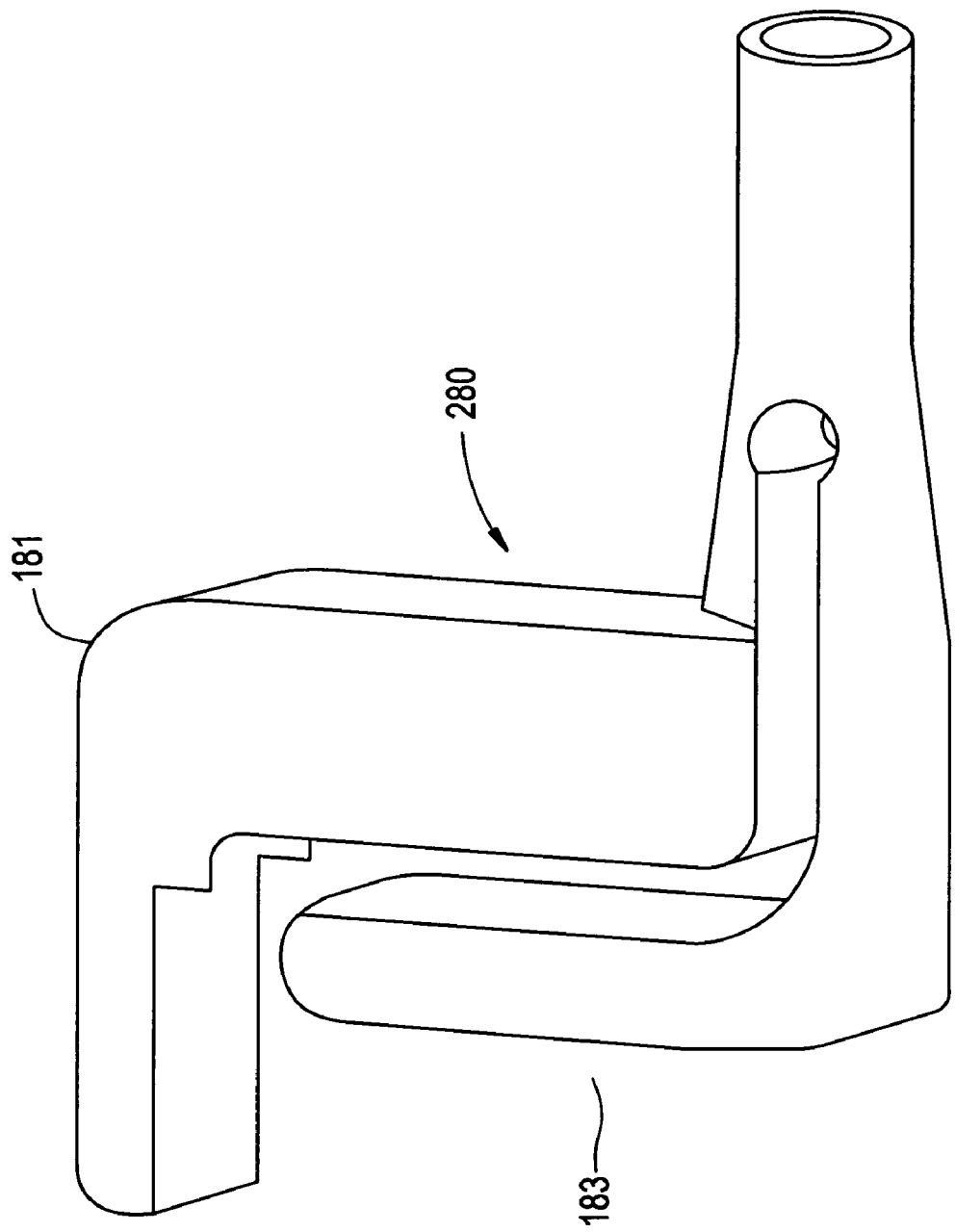

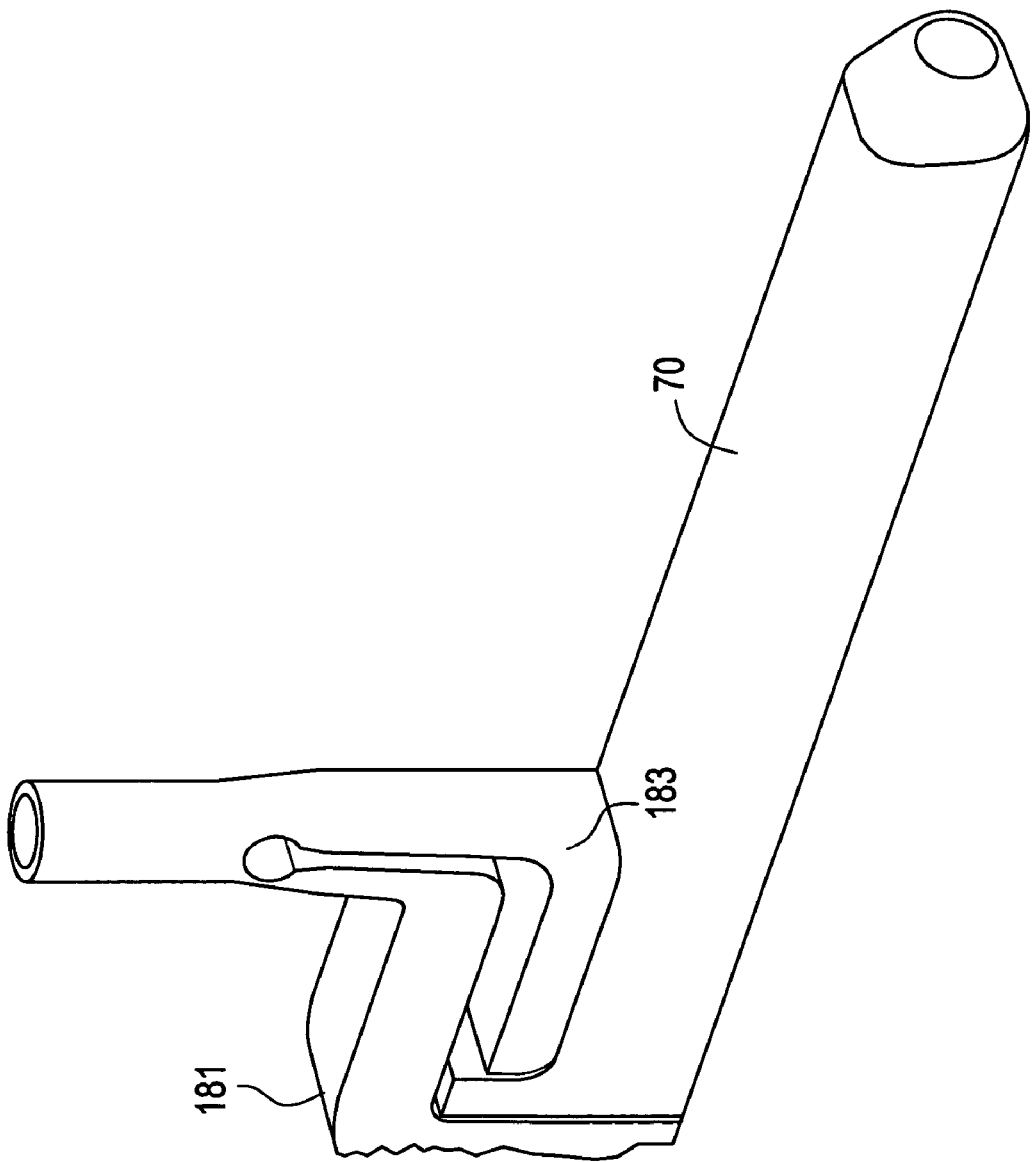

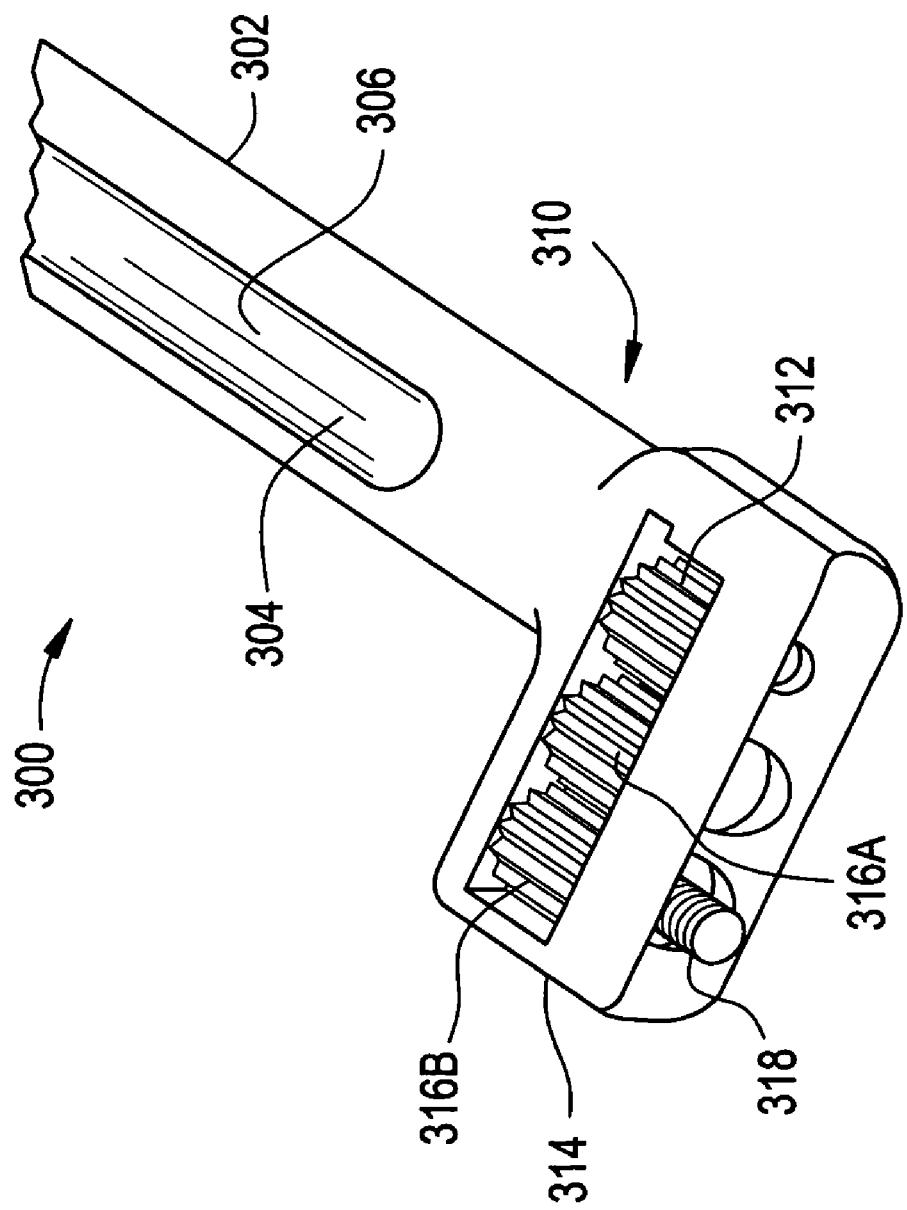

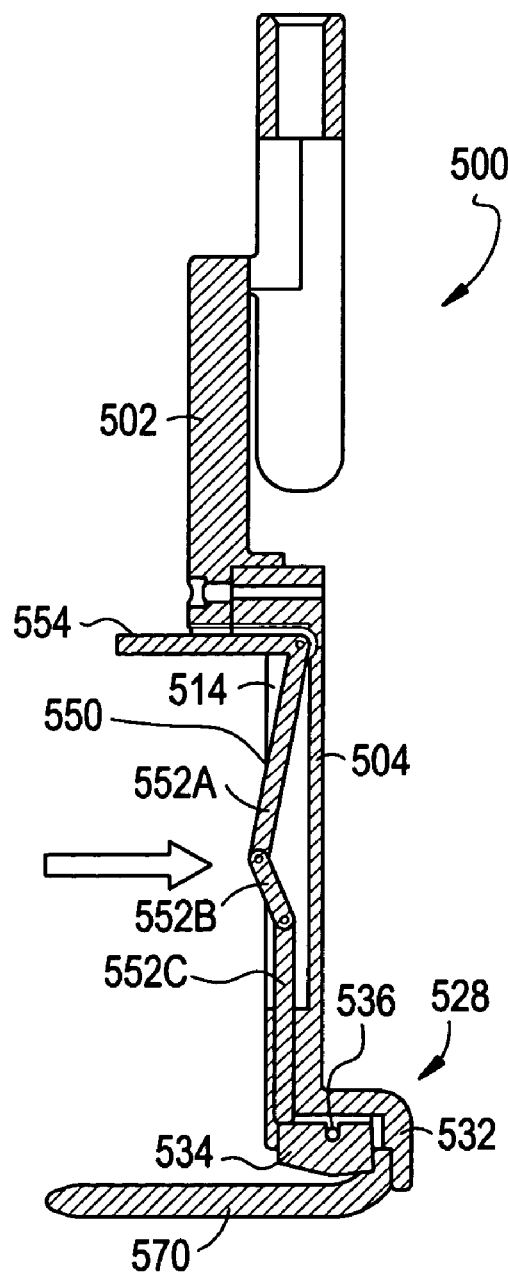
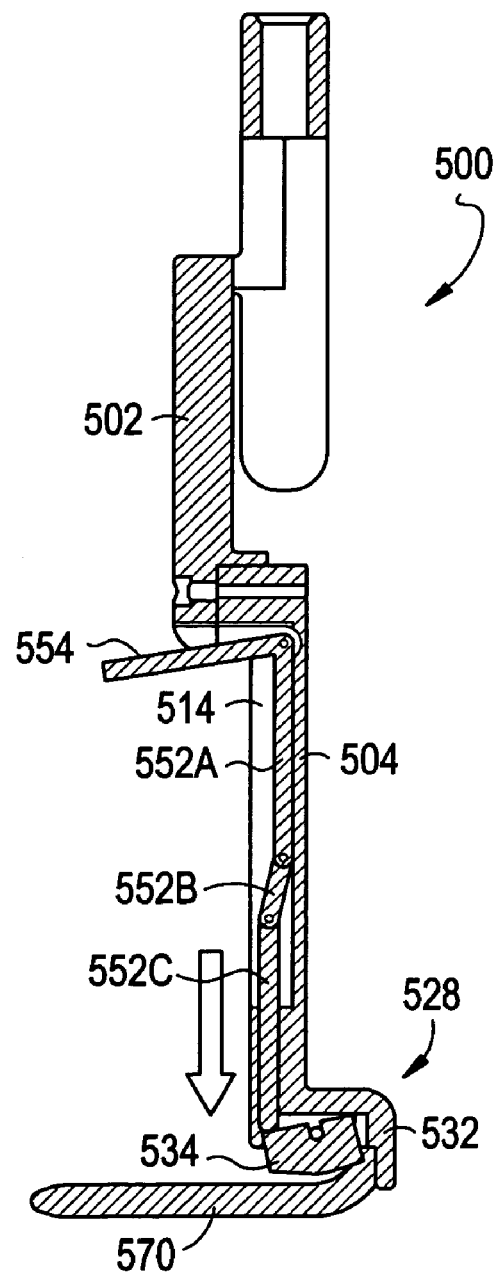
FIG. 42A
FIG. 42B

DEVICES AND METHODS FOR INSERTING A SPINAL FIXATION ELEMENT

CROSS-REFERENCE TO RELATED APPLICATIONS

This application claims priority to U.S. Provisional Patent Application No. 60/542,548, filed Feb. 6, 2004, and U.S. Provisional Patent Application No. 60/565,784, filed Apr. 27, 2004, both of which are incorporated herein by reference.

BACKGROUND

This application relates to tools for use in spinal surgery, and in particular to minimally invasive methods and devices for introducing a spinal fixation element to one or more spinal anchor sites within a patient's spine.

For a number of known reasons, spinal fixation devices are used in orthopedic surgery to align and/or fix a desired relationship between adjacent vertebral bodies. Such devices typically include a spinal fixation element, such as a relatively rigid fixation rod, that is coupled to adjacent vertebrae by attaching the element to various anchoring devices, such as hooks, bolts, wires, or screws. The fixation elements can have a predetermined contour that has been designed according to the properties of the target implantation site, and once installed, the instrument holds the vertebrae in a desired spatial relationship, either until desired healing or spinal fusion has taken place, or for some longer period of time.

Spinal fixation elements can be anchored to specific portions of the vertebrae. Since each vertebra varies in shape and size, a variety of anchoring devices have been developed to facilitate engagement of a particular portion of the bone. Pedicle screw assemblies, for example, have a shape and size that is configured to engage pedicle bone. Such screws typically include a threaded shank that is adapted to be threaded into a vertebra, and a head portion having a rod-receiving element, usually in the form of a U-shaped slot formed in the head. A set-screw, plug, or similar type of fastening mechanism is used to lock the fixation element, e.g., a spinal rod, into the rod-receiving head of the pedicle screw. In use, the shank portion of each screw is threaded into a vertebra, and once properly positioned, a rod is seated through the rod-receiving member of each screw and the rod is locked in place by tightening a cap or other fastener mechanism to securely interconnect each screw and the fixation rod.

Recently, the trend in spinal surgery has been moving toward providing minimally invasive devices and methods for implanting spinal fixation devices. One such method, for example, is disclosed in U.S. Pat. No. 6,530,929 of Justis et al. and it utilizes two percutaneous access devices for implanting an anchoring device, such as a spinal screw, into adjacent vertebrae. A spinal rod is then introduced through a third incision a distance apart from the percutaneous access sites, and the rod is transversely moved into the rod-engaging portion of each spinal screw. The percutaneous access devices can then be used to apply closure mechanisms to the rod-engaging heads to lock the rod therein. While this procedure offers advantages over prior art invasive techniques, the transverse introduction of the rod can cause significant damage to surrounding tissue and muscle. Moreover, the use of three separate access sites can undesirably lengthen the surgical procedure, and increase patient trauma and recovery time.

Accordingly, there remains a need for improved minimally invasive devices and methods for introducing a spinal fixation element into a patient's spine.

SUMMARY

Disclosed herein are minimally invasive methods and devices for delivering a spinal fixation element to one or more spinal anchor sites in a patient's spinal column. In one exemplary embodiment, a method for introducing a spinal fixation element into a patient's spinal column may comprise providing at least two percutaneous access devices, engaging a spinal fixation element to a shaft of a manipulator instrument, positioning the shaft of the manipulator instrument through the at least one sidewall opening of the at least two percutaneous access devices such that the spinal fixation element extends in an orientation substantially parallel to the longitudinal axis of each percutaneous access device, and rotating the manipulator instrument to change the orientation of the spinal fixation element to a substantially transverse orientation to seat the spinal fixation element in the receiver head of at least two adjacent spinal anchors.

In another exemplary embodiment, a percutaneous access system for introducing a spinal fixation element into a patient's body may comprise a plurality of spinal anchors that are adapted to be implanted in bone, a plurality of elongate, generally cylindrical hollow tubes, a manipulator instrument adapted to engage a spinal fixation element, and a spinal fixation element that is adapted to be engaged by the manipulator instrument and positioned in relation to at least two spinal anchors disposed within adjacent vertebra. In the exemplary embodiment, the tubes may have a proximal end, a distal end that is adapted to mate to a spinal anchor, and at least one sidewall opening extending from the distal end of the hollow tube and terminating at a position distal to the proximal end.

In a further exemplary embodiment, an instrument for positioning a spinal rod through a lumen of a cannula may comprise a shaft having a proximal end, a distal end and a longitudinal axis extending therebetween, and a rod engaging mechanism disposed at the distal end of the shaft. In the exemplary embodiment, the shaft may have an extent in a direction transverse to the longitudinal axis that is less than an extent of the lumen of the cannula and the rod engaging mechanism may have a rod engaging surface. The rod engaging mechanism, in the exemplary embodiment, may be movable between a first position, in which the rod engaging surface engages the rod, and a second position, in which the rod engaging surface is displaced from the rod.

In another exemplary embodiment, a method for determining the length of a spinal fixation element for insertion between two bone anchors may comprise inserting a first arm of a measuring instrument through a first percutaneous access device into proximity to a first bone anchor connected to the first percutaneous access device, inserting a second arm of the measuring instrument through a second percutaneous access device into proximity to a second bone anchor connected to the second percutaneous access device, determining the distance between a distal end of the first arm and distal end of a second arm, and selecting a spinal fixation element based on the determined distance.

In a further exemplary embodiment, a method for introducing a spinal fixation element between two bone anchors may comprise engaging a spinal fixation element to a shaft of an instrument, positioning the shaft of the instrument through a sidewall opening of a first percutaneous access device connected to a first bone anchor and through a side wall opening of a second percutaneous access device connected to a second bone anchor, the spinal fixation element extending in an orientation substantially parallel to the longitudinal axis of at least one of the first percutaneous access device and the second percutaneous access device, and pivoting the instrument to change the orientation of the spinal fixation element and position the spinal fixation element in proximity to the first bone anchor and in proximity to the second bone anchor.

BRIEF DESCRIPTION OF THE DRAWINGS

These and other features and advantages of the methods and devices disclosed herein will be more fully understood by reference to the following detailed description in conjunction with the attached drawings in which like reference numerals refer to like elements through the different views. The drawings illustrate principles of the methods and devices disclosed herein and, although not to scale, show relative dimensions.

FIGS. 5A and B are cutaway perspective views of an exemplary embodiment of a percutaneous access device having a guide member;

FIG. 7A is front view of an exemplary embodiment of an instrument for engaging a spinal fixation element;

FIG. 7B is a side view of the instrument of FIG. 7A;

FIG. 7C is an bottom view of the instrument of FIG. 7C;

FIG. 8A is a front view of the instrument of FIG. 7A, illustrating a spinal fixation element connected to a distal end of the instrument;

FIG. 8B is a side view of the instrument of FIG. 7A, illustrating a spinal fixation element connected to a distal end of the instrument;

FIG. 8C is a bottom view of the instrument of FIG. 7A, illustrating a spinal fixation element connected to a distal end of the instrument;

FIG. 8D is a perspective view of the distal end of the instrument of FIG. 7A, illustrating the connection of a spinal fixation element to the instrument;

FIG. 9A is a perspective view of a distal end of an instrument for engaging a spinal fixation element, the exemplary instrument having a clamping mechanism with a clamp jaw;

FIG. 9B is a perspective view of the instrument of FIG. 9A, illustrating the instrument connected to a spinal fixation element;

FIG. 10B is a perspective view of the collet of the instrument of FIG. 10A;

FIG. 10C is a perspective view of the collet of the instrument of FIG. 10A, illustrating the collet engaging a spinal fixation element;

FIG. 11B is a perspective view of the distal end of the instrument of FIG. 11A, illustrating the instrument engaged to a spinal fixation element;

FIG. 42A is a side elevational view in cross section of the instrument of FIG. 40, illustrating the instrument in a first, disengaged position;

FIG. 42B is a side elevational view in cross section of the instrument of FIG. 40, illustrating the instrument in a second, engaged position;

DETAILED DESCRIPTION

Figure 1:
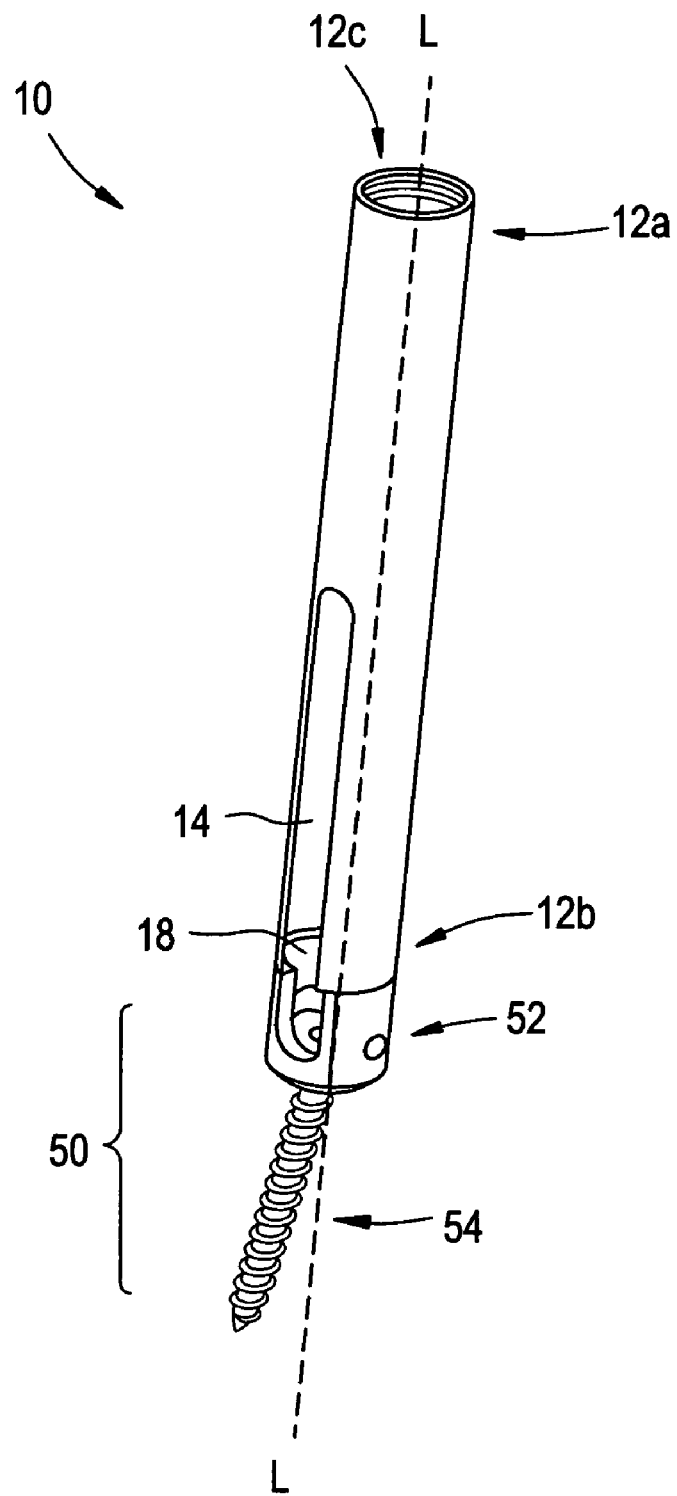
FIG. 1 is a perspective view of an exemplary embodiment of a percutaneous access device coupled to a spinal anchor.

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The articles "a" and "an" are used herein to refer to one or to more than one (i.e. to at least one) of the grammatical object of the article. By way of example, "an element" means one element or more than one element.

The terms "comprise," "include," and "have," and the derivatives thereof, are used herein interchangeably as comprehensive, open-ended terms. For example, use of "comprising," "including," or "having" means that whatever element is comprised, had, or included, is not the only element encompassed by the subject of the clause that contains the verb.

Disclosed herein are minimally invasive methods and devices for introducing a spinal fixation element into a surgical site in a patient's spinal column. In general, the methods disclosed herein involve advancing a spinal fixation element in a lengthwise orientation along a minimally invasive pathway that extends from a minimally invasive percutaneous incision to a spinal anchor site. In one exemplary embodiment, a percutaneous access device is used to create the minimally invasive pathway for receiving the spinal fixation element and for delivering the fixation element to a spinal anchor site. The spinal fixation element is preferably inserted through a lumen in the percutaneous access device in a lengthwise orientation, such that the spinal fixation element is oriented substantially parallel to a longitudinal axis of the percutaneous access device. As the spinal fixation element approaches or reaches the distal end of the pathway, the spinal fixation element can be manipulated to orient it at a desired angle with respect to the percutaneous access device, preferably such that the spinal fixation element is substantially parallel to the patient's spinal column. The spinal fixation element can then optionally be positioned to couple the spinal fixation element, either directly or indirectly, to one or more spinal anchors. A fastening element or other closure mechanism, if necessary, can then be introduced into the spinal anchor site to fixedly mate the spinal fixation element to the anchor(s).

The methods and devices disclosed herein are particularly advantageous in that they can be achieved using one or more minimally invasive percutaneous incisions for accessing the spinal column. Such incisions minimize damage to intervening tissues, and reduce recovery time and post-operative pain. The methods and devices disclosed herein may advantageously provide techniques for delivering spinal fixation elements and anchors along a minimally invasive pathway, thus eliminating the need to create a large working area at the surgical site.

Figure 2:
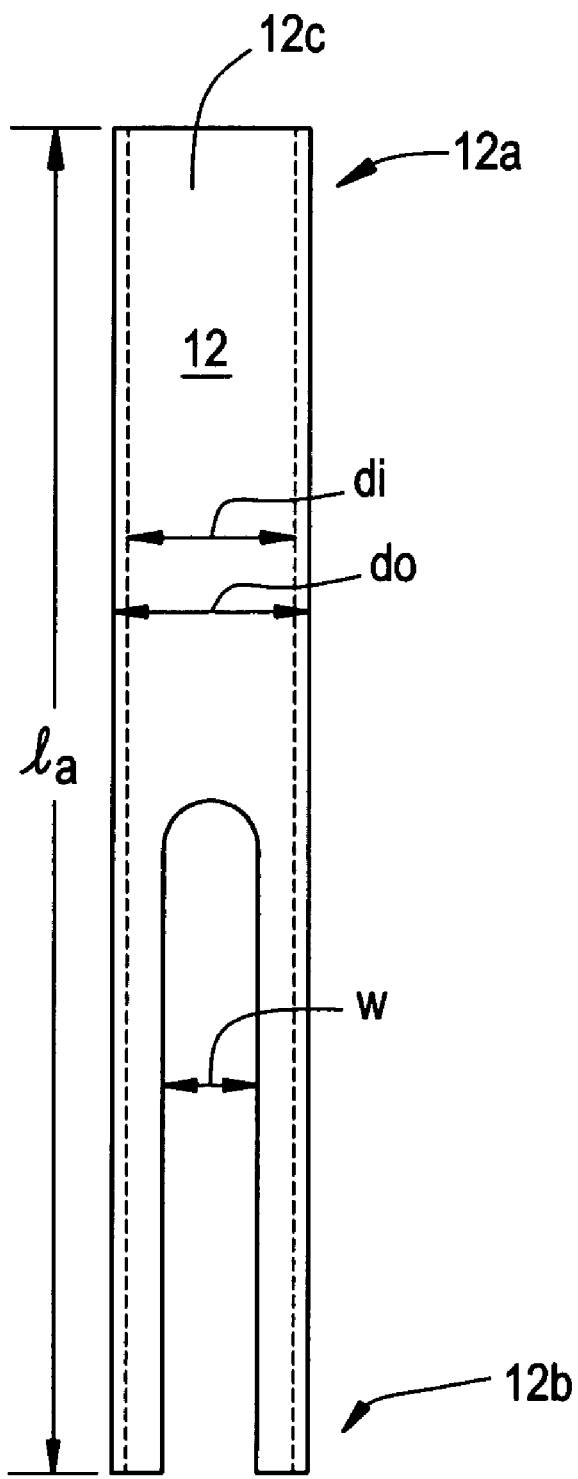
FIG. 2 is a side elevational view taken along the longitudinal axis L of the percutaneous access device shown in FIG. 1.

While a variety of devices can be used to perform the methods disclosed herein, FIGS. 1 and 2 illustrate an exemplary embodiment of a percutaneous access device 12 that is mated to a spinal anchor 50 (FIG. 1) to form a spinal implant assembly 10. As shown, the device 12 is in the form of a generally elongate, cylindrical tube having an inner lumen 12c formed therein and defining a longitudinal axis L that extends between proximal and distal ends 12a, 12b. The size of the access device 12 can vary depending on the intended use. In certain exemplary embodiments, for example, the percutaneous access device 12 may have a length $l_a$ that allows the proximal end 12a of the access device 12 to be positioned outside the patient's body, while the distal end 12b of the access device 12 is coupled to, or positioned adjacent to, a spinal anchor, e.g., anchor 50, that is disposed in a vertebra in a patient's spine. The illustrated exemplary percutaneous access device 12 provides a minimally invasive pathway for the delivery of a spinal fixation element, such as a spinal rod. The exemplary percutaneous access device 12 may be implanted through a minimally invasive percutaneous incision, which is a relatively small incision that typically has a length that is less than a diameter or width of the device being inserted therethrough. For example, a minimally invasive percutaneous incision may be a stab or point incision through which the percutaneous access device is positioned.

In an exemplary embodiment, the device 12 has an inner diameter $d_i$ that is sufficient to allow a spinal fixation element to be introduced therethrough, preferably in a lengthwise orientation. The inner diameter $d_i$ can also optionally be configured to allow a driver mechanism to be introduced therethrough for applying a closure mechanism to lock the spinal fixation element in relation to a spinal anchor. The outer diameter $d_o$ of the access device 12 can also vary, and it can be the same as, less than, or greater than an outer diameter $d_r$ of the spinal anchor. In the illustrated embodiment, the access device 12 has an outer diameter $d_o$ that is substantially the same as an outer diameter of the spinal anchor, which, in the illustrated exemplary embodiment, is the outer diameter of the receiver head or member 52 of the exemplary spinal screw 50. This is particularly advantageous in that the size of the incision does not need to be any larger than necessary. The matching outer diameters of the access device 12 and the anchor 50 also allow the access device 12 and/or the anchor 50 to be introduced through a cannula. If the access device 12 is mated to the anchor 50, the matching outer diameters also allow a sleeve or other device to be slidably disposed therearound to prevent disengagement between the access device 12 and the anchor 50. In another, exemplary embodiment, the outer diameter $d_o$ of the access device 12 can be slightly greater than the outer diameter of the spinal anchor. By way of non-limiting example, where a receiver head of the spinal anchor has an outer diameter that is about 13 mm, the access device 12 preferably has an outer diameter $d_o$ that is about 15 mm.

The percutaneous access device 12 may also include a pair of opposed sidewall openings or slots 14a formed therein and extending proximally from the distal end 12b thereof. In an alternate exemplary embodiment of a percutaneous access device 212 shown in FIG. 3, an additional pair of opposed proximal sidewall openings 14b are also formed in alignment with the first pair of distal sidewall openings 14a and extend distally from the proximal end 12a of the device. A web 16 is formed in the middle portion of the device separating the proximal and distal sidewall openings 14a, 14b. The sidewall openings 14a,b provide access to the lumen of the device 212 for an instrument holding a spinal fixation element and the spinal fixation element.

Figure 3:
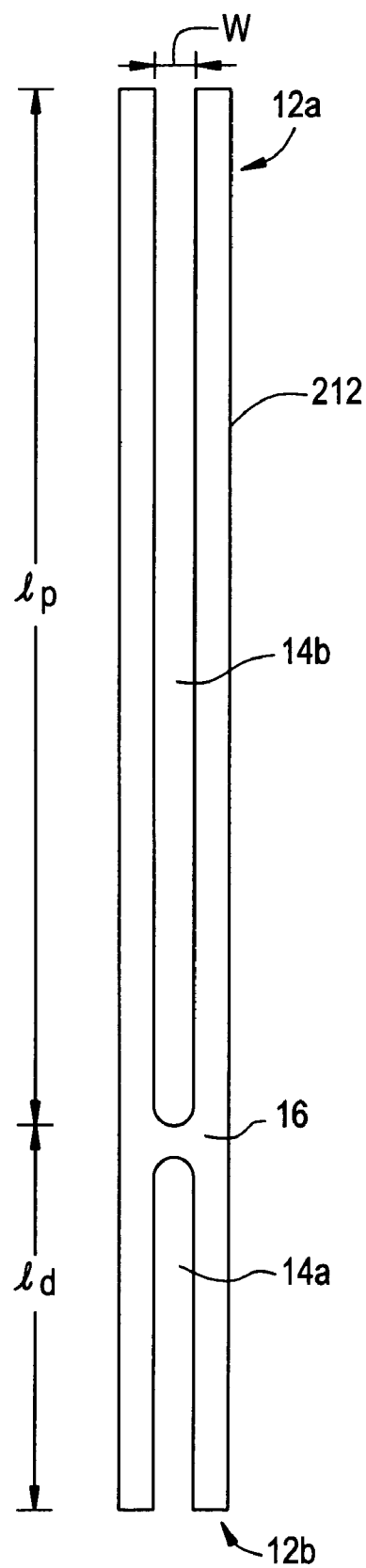
FIG. 3 is a side view of an exemplary embodiment of a percutaneous access device.

A spinal fixation element, such as, for example, a spinal rod, may be introduced through a sidewall opening, such as a proximal sidewall opening 14b of the embodiment illustrated in FIG. 3, into the lumen of the device 212 in a first, lengthwise orientation, in which the spinal fixation element is substantially parallel to the longitudinal axis L of the access device 212. The spinal fixation element can then to be manipulated to extend at an angle with respect to the first orientation, such that the fixation element extends in a direction substantially transverse to the longitudinal axis L of the access device 212, for example, in a direction that is substantially parallel to the patient's spine. Since the length L of the spinal fixation element will necessarily be greater than the inner diameter $d_i$ of the access device 212, the openings 14 allow the spinal fixation element to pass therethrough while being transitioned from the first, lengthwise orientation to the second orientation. A person skilled in the art will appreciate that the exact position of the spinal fixation element with respect to the longitudinal axis L will of course vary depending on the configuration of the spinal fixation element.

Figure 4:
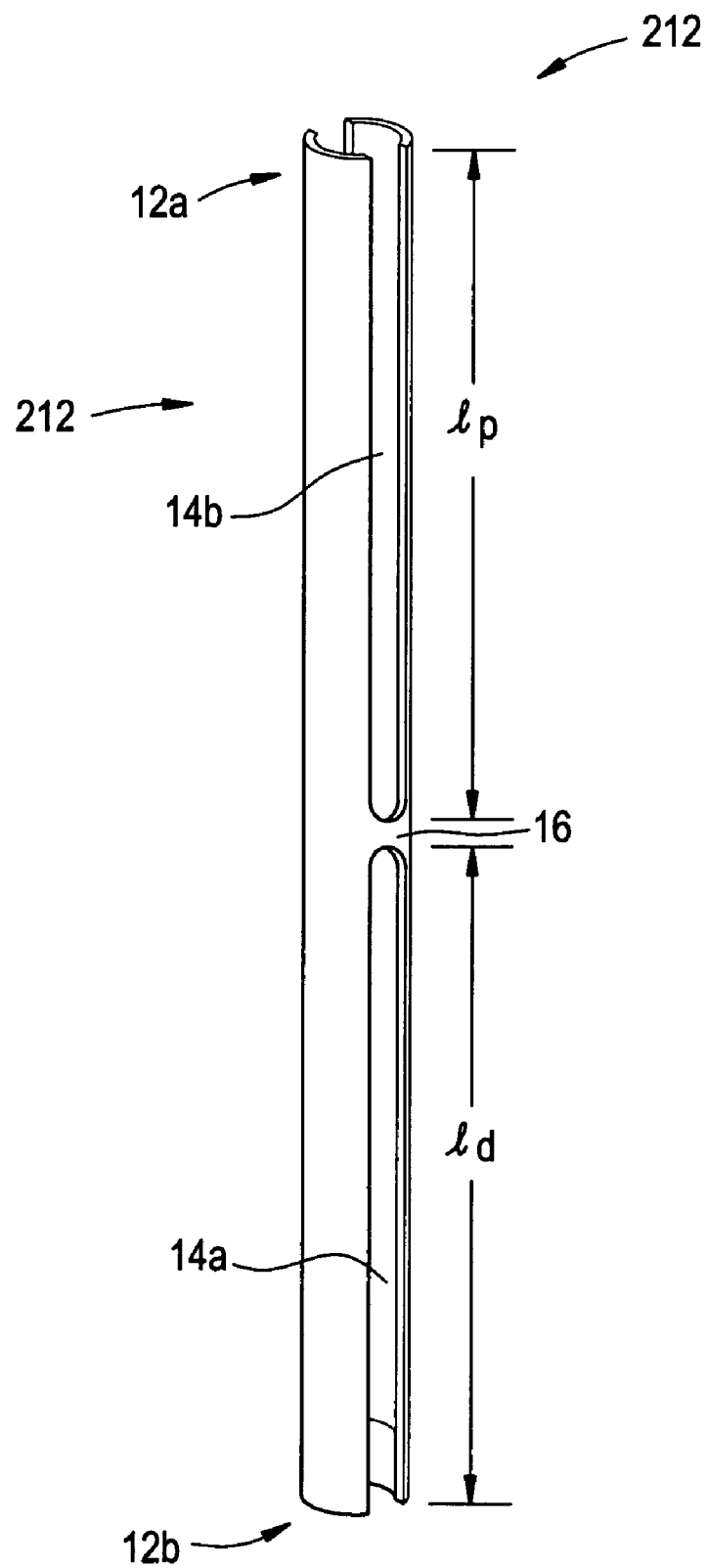
FIG. 4 is a perspective view of an exemplary embodiment of a percutaneous access device.

As shown in FIGS. 3 and 4, the shape and size of each sidewall opening 14a,b can vary, but the opening(s) 14a,b may be effective to allow movement of the spinal fixation element from the first orientation to the second orientation. The relationship of the length of the sidewall openings can vary. For example in the embodiment illustrated in FIG. 4, each pair of sidewall openings 14a,b extend over about less than half of the length of the percutaneous access device 212. In this exemplary embodiment, the device exhibits a generally H-shape when viewed facing the openings 14. In the exemplary embodiment illustrated in FIG. 3, the length of the proximal sidewall openings extends over more than half the length of the device and is longer than the length of the distal sidewall openings, however, one skilled in the art will appreciate that in other embodiments the length of the distal sidewall openings may be greater than the length of the proximal sidewall openings, depending for example, on the surgical approach, e.g., posterior, anterior, or lateral, and the region of the spine treated. In addition, the length $l_p$ of the sidewall openings 14b at the proximal end of the device may depend on, for example, the size of the patient and the design of the instrument to hold the spinal fixation element.

The proximal sidewall openings 14b of the device, in the exemplary embodiment, are open at the proximal end 12a of the device. The proximal sidewall openings 14b terminate at the distal end thereof at the web 16. Leaving the proximal sidewall openings 14b open at the proximal end 12a of the device allows for the instrument holding the spinal fixation element to pass through unobstructed as the instrument manipulates the spinal fixation element from one orientation to another orientation.

In the exemplary embodiment, the distal sidewall openings 14a in the distal end of the device may be open at the distal end 12b. The distal sidewall openings 14a terminate at the proximal end thereof at the web 16. The web 16, in the exemplary embodiment, provides strength and rigidity to the device 212 and provides a bearing surface to facilitate manipulation of the spinal fixation element with an instrument, as discussed below. The length $l_d$ of the distal sidewall openings 14a can be, for example, a function of the distance between the spinal anchors, the length of the spinal fixation element, the surgical approach, the region of the spine being treated, and/or the patient anatomy. The length of the sidewall openings 14a, 14b may determine the placement of the web 16, which can be used as a guide to facilitate rotation of the instrument holding the spinal fixation element when manipulating the fixation element from one orientation to a second orientation. The shape of the sidewall openings 14a, b can be generally elongate, and may have a width w that is sufficient to accommodate the diameter of the spinal fixation element and the shaft of the instrument holding the spinal fixation element. Another function of the length of the access device is to enable the shaft of the manipulator instrument to maintain contact with the device as it manipulates the spinal fixation element from the first orientation to the second.

A person skilled in the art will appreciate that the percutaneous access device 12 can include any number of sidewall openings or slots having any shape that is sufficient to allow a spinal fixation element to be moved from the first orientation to the second orientation. Other embodiments of percutaneous access devices are described in commonly owned U.S. Patent Application Publication No. US 2005/0131421 A1, entitled "Methods and Devices for Minimally Invasive Spinal Fixation Element Placement" and U.S. Patent Application Publication No. 2005/0131422 A1, entitled "Methods and Devices for Spinal Fixation Element Placement," both of which are incorporated by reference in their entirety herein.

Figure 6A:
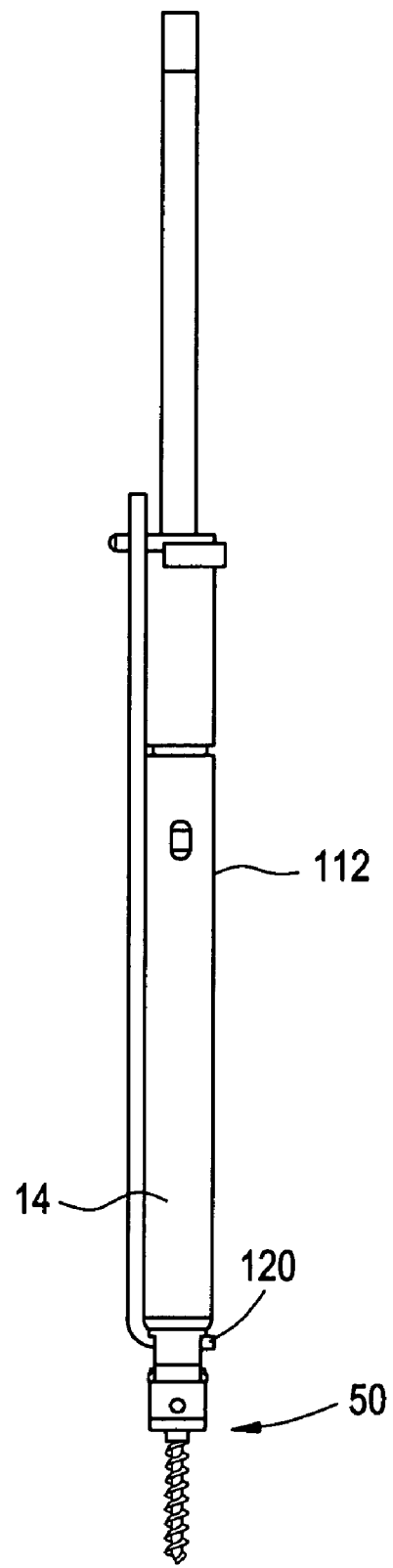
FIG. 6A is a sideview of an exemplary embodiment of a percutaneous access device having an external guide member.
Figure 6B:
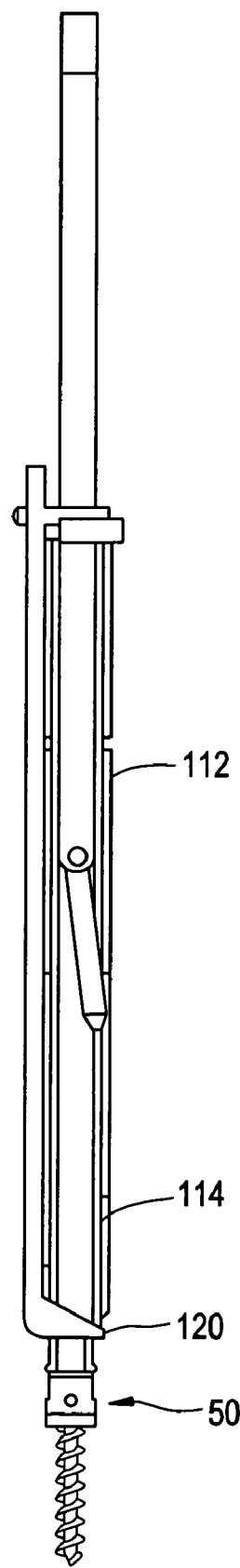
FIG. 6B is cutaway view showing a spinal fixation element moving through the percutaneous access device of FIG. 6A.

FIGS. 5-6B, illustrate another exemplary embodiment of a percutaneous access device 112 that includes an optional guide member 120 formed within the distal end 112b of the lumen 112c to facilitate guiding the spinal fixation element from a first orientation to a second orientation. The guide member 120 can have a variety of configurations, but it preferably is effective to guide the spinal fixation element from a first orientation toward the anchor 50 attached to, or positioned adjacent to, the access device 112, and optionally toward anchor(s) implanted in adjacent vertebrae. In an exemplary embodiment, as shown in FIGS. 5A-5B, the guide member 120 is in the form of a sloped shelf formed within the inner lumen 112c of the access device 112 and preferably positioned opposite to a single sidewall slot 114 formed in the access device 112. In an alternate embodiment, shown in FIGS. 6A-6B the sloped shelf can be externally attached to the proximal end of the access device 112 and enter the lumen from the sidewall opening 14. The sloped shelf can be adjustable to any position within the sidewall opening depending on where the user wants the spinal fixation element to begin changing its orientation. The sloped shelf 120 can vary in shape and size depending on the type of fixation element being used and/or the geometry of the access device. In use, as the leading end of a spinal fixation element, such as a spinal rod, contacts the shelf 120, the shelf 120 begins to direct the spinal fixation element into the second orientation, thereby causing the spinal fixation element to extend in a direction that is substantially transverse to the axis L of the device 112, and that is preferably substantially parallel to the patient's spinal column. The spinal fixation element can then be manipulated to position it in relation to one or more spinal anchors, as will be discussed in more detail below.

Referring back to FIG. 1, in use, the percutaneous access device 12 can be adapted to attach to a spinal anchor 50. Accordingly, the distal end 12b of the percutaneous access device 12 can include one or more mating elements 18 formed thereon or therein for engaging the anchor 50. Suitable mating elements include, for example, threads, a twist-lock engagement, a snap-on engagement, or any other technique known in the art, and in an exemplary embodiment the mating elements are formed on opposed inner surfaces of the distal end 12b of the access device 12. A sleeve 100 (partially shown in FIG. 5B) or other device, preferably having sidewall openings (not shown) that correspond with the sidewall openings 14 formed in the percutaneous access device 12, can also be placed over the percutaneous access device 12, and optionally over the implant 50 as well, to prevent disengagement of the access device 12 from the implant 50 during use. Exemplary techniques for mating the percutaneous access device 12 to an anchor are disclosed in commonly owned U.S. Patent Application Publication No. 2005/0131408 A1, entitled "Percutaneous Access Devices and Bone Anchor Assemblies," which is incorporated by reference in its entirety herewith. A person skilled in the art will appreciate that a variety of other techniques can be used to removably mate the percutaneous access device to an anchor.

FIGS. 7-8D illustrate an exemplary instrument 80 for holding a spinal fixation element, such as, for example, a spinal rod, and manipulating the spinal fixation element into position relative to a spinal anchor through a cannula, such as a percutaneous access device described above. The exemplary instrument 80 has a generally elongate shaft 82 defining a longitudinal axis L that extends between proximal 82a and distal 82b ends. The distal end 82b is adapted to engage a spinal fixation element. The width $w_s$ of the shaft 82 is sized to fit within the lumen of the cannula through which the spinal fixation element is to be introduced. In embodiments in which a percutaneous access device is employed, for example, the width $w_s$ of the shaft 82 is sized to fit within the sidewall openings and lumen of the percutaneous access device. The length $l_s$ of the shaft 82 can vary depending on the cannula with which it is designed to be used. In embodiments in which a percutaneous access device is employed, for example, the length $l_s$ may vary depending on, for example, the length of the percutaneous access device to be used and the sidewall configurations. In the exemplary embodiment, the shaft 82 may have an inner lumen 91 formed therein to provide access to the spinal fixation element and, in certain exemplary embodiments, such as the illustrated embodiment, to accommodate at least a portion of a spinal fixation element engagement mechanism. As discussed in more detail below, the spinal fixation element engagement mechanism allows the instrument to be connected to a spinal fixation element and permits the spinal fixation element to be released from the instrument when, for example, the spinal fixation element is in a final position relative to a spinal anchor.

In the illustrated exemplary embodiment, the proximal end 82a of the shaft 82 connects to a handle 86 having a U-shaped configuration adapted to fit around or cup the proximal end of a cannula, such as, for example, a percutaneous access device. The proximal end 87 of the handle 86 has a through-hole 88 to allow an instrument to be inserted therethrough to access the spinal fixation element engagement mechanism and/or the spinal fixation element through the inner lumen 91.

In certain exemplary embodiment, the spinal fixation element engagement mechanism of the instrument may rigidly engage the spinal fixation element to maintain the spinal fixation element in a fixed position during the entire procedure. Preferably, the spinal fixation element engagement mechanism, in such exemplary embodiments, orients the longitudinal axis of the instrument shaft 82 perpendicular to the spinal fixation element to facilitate entry into the percutaneous access device. For example, the illustrated instrument includes a spinal fixation element engaging mechanism comprising an elongated pin 84 having a threaded distal end 93 for engaging a spinal fixation element. For example, in the illustrated embodiment, the spinal fixation element is a rod having an internally threaded hole 87 positioned thereon for receiving the threaded distal end 93 of the elongated pin 84. The proximal end 95 of the elongated pin 84 includes a drive feature 85 that is accessible at the proximal end 82a of the shaft 82. The drive feature 85, and the pin 84, is retained in position by a retaining pin 97 that limits axial motion of the drive feature 85 relative to the instrument shaft 82 but permits relative rotation. In the exemplary embodiment, the drive feature 85 is generally spool-shaped and includes a hexagonal or other suitable shaped socket 99 for receiving an instrument, such as a screw driver or the like, for rotating the pin 84. Such an instrument, for example, a screwdriver, may be positioned through the through hole 88 in the proximal end 87 of the instrument handle 86 to engage the drive feature 85. In operation, rotation of the pin 84 one direction cause the distal end 93 of the pin 84 advance into to the hole 87 in the exemplary rod 70 and rotation in the opposite direction causes the distal end 93 to retreat from the hole 87.

One skilled in the art will appreciate that the threaded hole 87 may be provided at any position on the rod 70. In the illustrated exemplary embodiment, for example, the threaded hole 87 is positioned at an end of the rod 70. In certain embodiments, such as the illustrated embodiment, the rod 70 may have a bullet-shaped tip 71 to facilitate advancement of rod 70 through tissue. In such embodiments, the threaded hole 87 may be positioned at an end of the rod 70 opposite the tip 71.

In certain exemplary embodiments, the shaft 82 of the instrument 80 may have an extent, at least the distal end 82b of the shaft 82, in a direction transverse to the longitudinal axis L of the shaft 82, that is less than or equal to the extent of the spinal fixation element in a direction transverse to the longitudinal axis of the spinal fixation element. For example, in the illustrated embodiment, the width $w_s$ is less that or equal to the diameter of the spinal rod 70. In the illustrated exemplary embodiment, the shaft 82 has a generally circular cross section such that width $w_s$ is the diameter of the shaft 82. In other exemplary embodiments, the shaft 82 may have a non-circular cross section, including for example, oblong, elliptical, polygonal, and/or rectilinear. In the case of a non-circular cross section, the width $w_s$ can be measured in a direction transverse to the longitudinal axis L of the shaft 82.

Figure 11A:
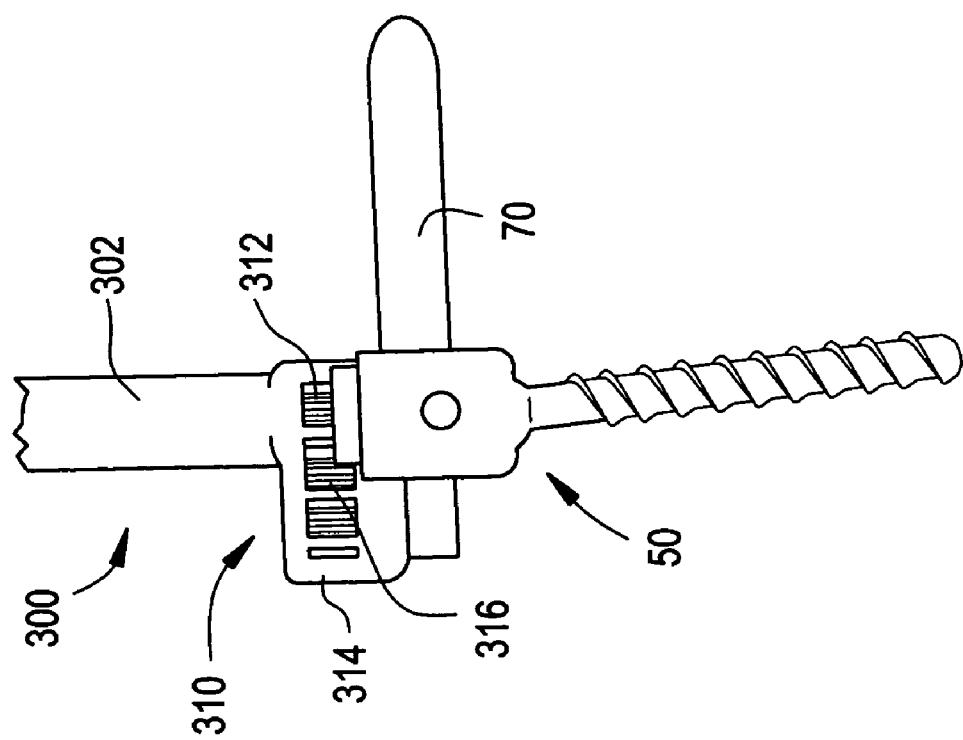
FIG. 11A is a perspective view of the distal end of another exemplary embodiment of an instrument for engaging a spinal fixation element, illustrating the instrument connected to a spinal rod.
Figure 11C:
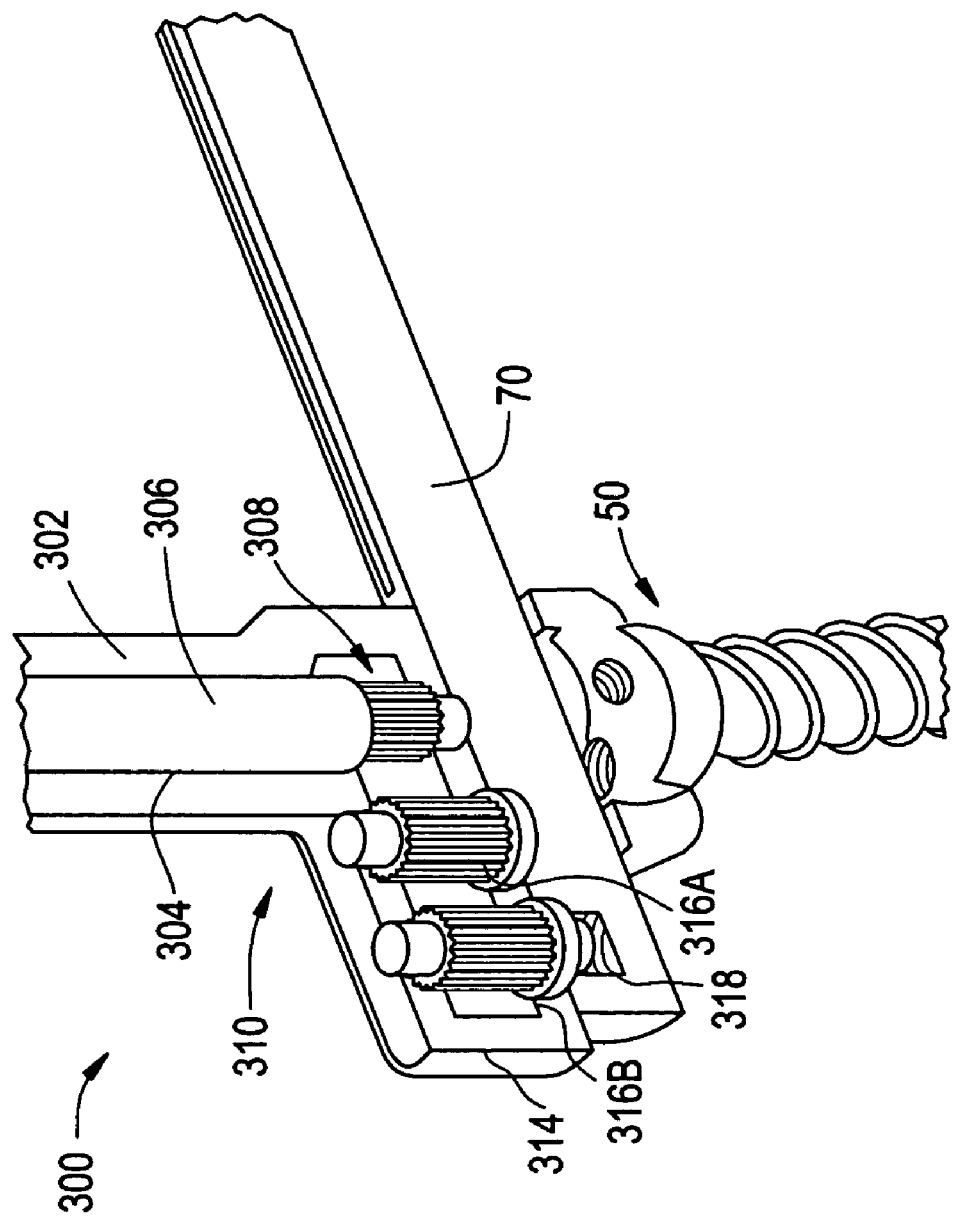
FIG. 11C is a partially cut away, perspective view of the distal end of the instrument of FIG. 11A, illustrating the instrument disengaged from a spinal fixation element.

FIGS. 11A-11C illustrate another exemplary embodiment of instrument 300 for positioning a spinal fixation element through a lumen of a cannula. In the illustrated embodiment, the instrument 300 includes instrument shaft 302 having a distal end 310 that is configured to threadingly engage a spinal fixation element, such as, for example, a spinal rod 70. The instrument shaft 302 includes a lumen 304 through which an actuation mechanism is positioned. In the illustrated exemplary embodiment, the actuation mechanism is an elongated pin 306 that is rotatable within the lumen 304 and includes a distal end 308 having a first gear 312A formed thereon. The distal end 310 of the instrument shaft 302 is generally L-shaped and includes a laterally offset housing 314 that extends in a direction transverse to the longitudinal axis of the instrument shaft 302. The laterally offset housing 314 may include a spinal fixation element engaging mechanism, which in the exemplary embodiment comprises one or more gears 312 for translating the rotational motion of the pin 306 to a threaded shaft 318 that is configured to engage an internally threaded hole 87 in the spinal fixation element. In the illustrated exemplary embodiment, three adjacent gears 312A, B,C are provided, although any number of gears may be provided depending on the application. In the illustrated exemplary embodiment, the threaded shaft 318 is connected to one of the gears 312A. In operation, rotation of the shaft 306 causes the first gears 312A to rotate and, through engagement of the gear teeth of the second and third gears 312B,C, the rotational movement is translated to threaded shaft 318.

Figure 10A:
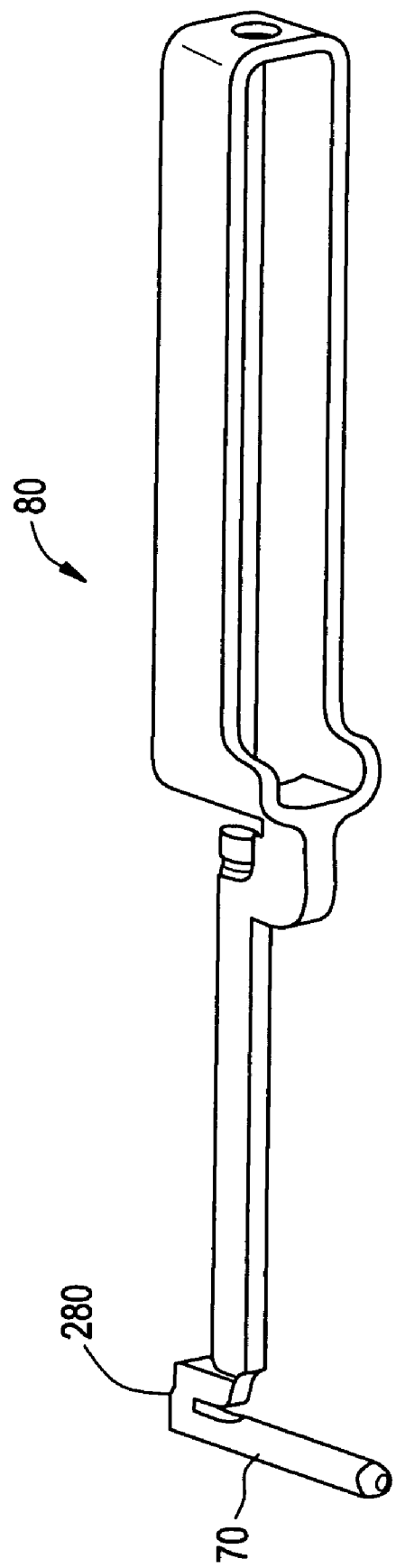
FIG. 10A is a perspective view of an instrument for engaging a spinal fixation element, the exemplary instrument having a collet designed to engage a spinal fixation element.

In another embodiment, the instrument rigidly engages the spinal fixation element by a clamping mechanism. The clamping mechanism at the distal end of the instrument shaft can be a jaw clamp 180 having one arm 181 biased in an open position to allow the fixation element to be inserted. The arm 181 has a projection 182 adapted to mate with a groove 183 on the spinal fixation element to secure it within the clamp. An example of a jaw clamp is shown in FIGS. 9A-B. The arm is spring loaded in the open position and movable to a closed position by using a screwdriver. The clamping arm can mate with any projection such as a lip or tab or indention such as a groove, channel or detent of the fixation element to hold the element in place during manipulation through the percutaneous access device into final position with the spinal anchors. Instead of a jaw clamp, a collet style clamp can be used where two fingers 181, 183 of the collet are squeezed together by an outer sleeve to clamp a projection 282 on the spinal fixation element. An example of a collet style clamp 280 is shown in FIGS. 10A-C.

FIGS. 32A-38D illustrate other exemplary embodiments of an instrument 400 for engaging a spinal fixation element, such as a spinal rod 470, and manipulating the spinal fixation element through a cannula, such as a percutaneous access device described above. In the illustrated exemplary embodiment, the instrument 400 includes a handle 402 and an instrument shaft 404. The handle 402 may be configured in a manner analogous to the instrument 80 described above and may be connected to the instrument shaft 404 by one or more fasteners 406. In the illustrated exemplary embodiment, for example, two threaded bolts 406 connect the handle 402 to the instrument shaft 404. The bolts are received in threaded holes 408 provided in the instrument shaft 404. In alternative exemplary embodiments, such as that shown in FIG. 38D the handle 402 and shaft 404 may be of unitary construction.

The instrument shaft 404 of the exemplary instrument 400 may include a lumen 414 through which an actuation mechanism is positioned. In the illustrated exemplary embodiment, the actuation mechanism is elongated pin 416 positioned in the lumen 414. The pin 416 is rotatable within the lumen 414 and includes a proximal end 418 that includes external threads 420 for matingly engaging internal threads 424 provided in the lumen 414 at the proximal end 422 of the instrument shaft 404. Rotation of the elongated pin 416 in a first direction causes the distal end 426 of the elongate pin 416 to advance toward the distal end 428 of the instrument shaft 404. Rotation of the elongate pin 416 in a second direction, opposite the first direction, causes distal end 426 of the elongate pin 416 to retreat from the distal end 428 of the instrument shaft 404.

The distal end 428 of the instrument shaft 404 is configured to house a spinal fixation element engaging mechanism and to seat the spinal fixation element, which in the illustrated embodiment is a spinal rod 470. In the illustrated exemplary embodiment, the distal end 428 of the instrument shaft 404 is oriented at an angle to the longitudinal axis and includes an angled lumen 430 that houses and defines a path of motion for the rod engaging mechanism. In the illustrated exemplary embodiment, the path defined by the angled lumen 430 is generally linear and can be oriented between approximately 40° and approximately 60° to the longitudinal axis of the instrument shaft 404, although, one skilled in art will appreciate that the other shapes and orientations of the path, including, for example, arcuate, are possible. In the exemplary embodiment illustrated in FIG. 38A, for example, the path is oriented at 45° to the longitudinal axis of the instrument shaft 404. In the exemplary embodiment illustrated in FIG. 38B, for example, the path is oriented at 55° to the longitudinal axis of the instrument shaft 404. The distal end 428 of the instrument shaft 404, in the illustrated exemplary embodiment, includes a generally hook shaped rod seat 432 positioned distal to and at the terminus of the angled lumen 430. The rod engaging mechanism, in the illustrated exemplary embodiment, is a cylindrically shaped component 434 that is seated in and movable within the path defined by the angled lumen 430. The cylindrical component 434 includes a proximal surface 436 and a distal, rod engaging surface 438.

Figure 38A:
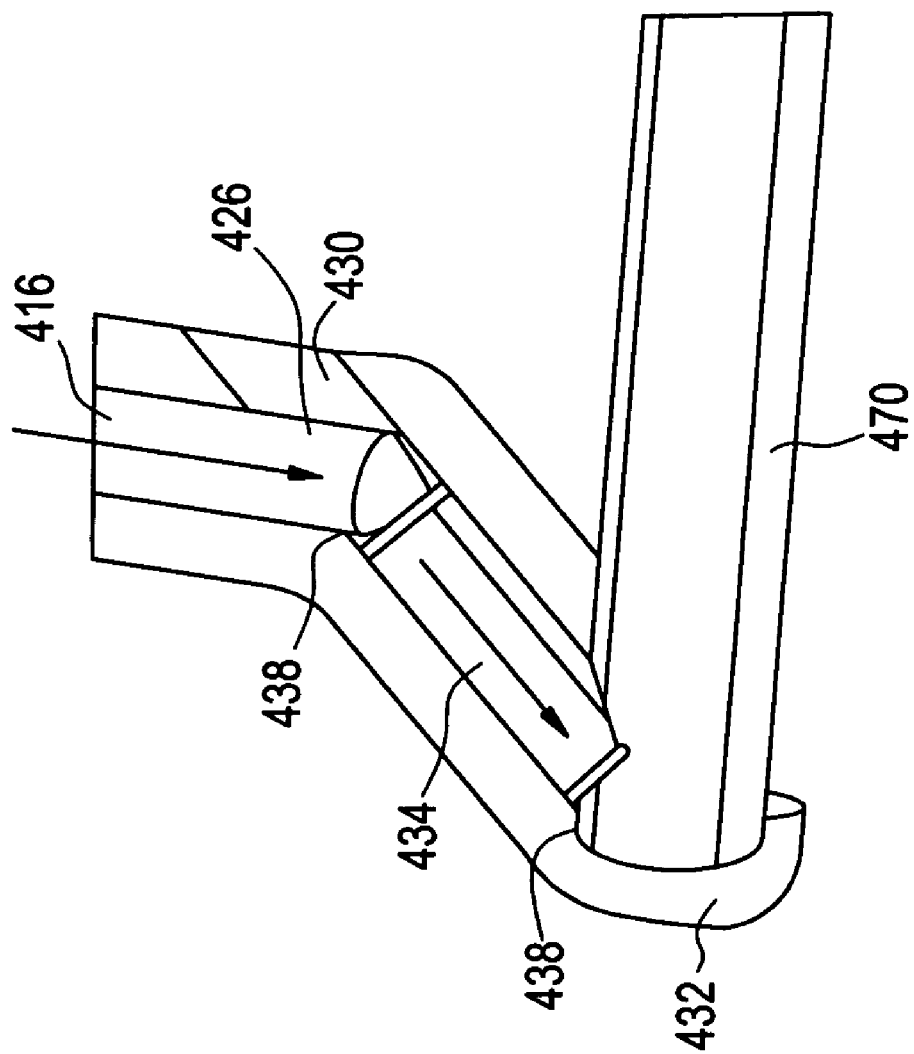
FIG. 38A is a side elevational view in cross section of the distal end of the shaft of the instrument of FIG. 32A, illustrating the operation of the instrument.
Figure 38B:
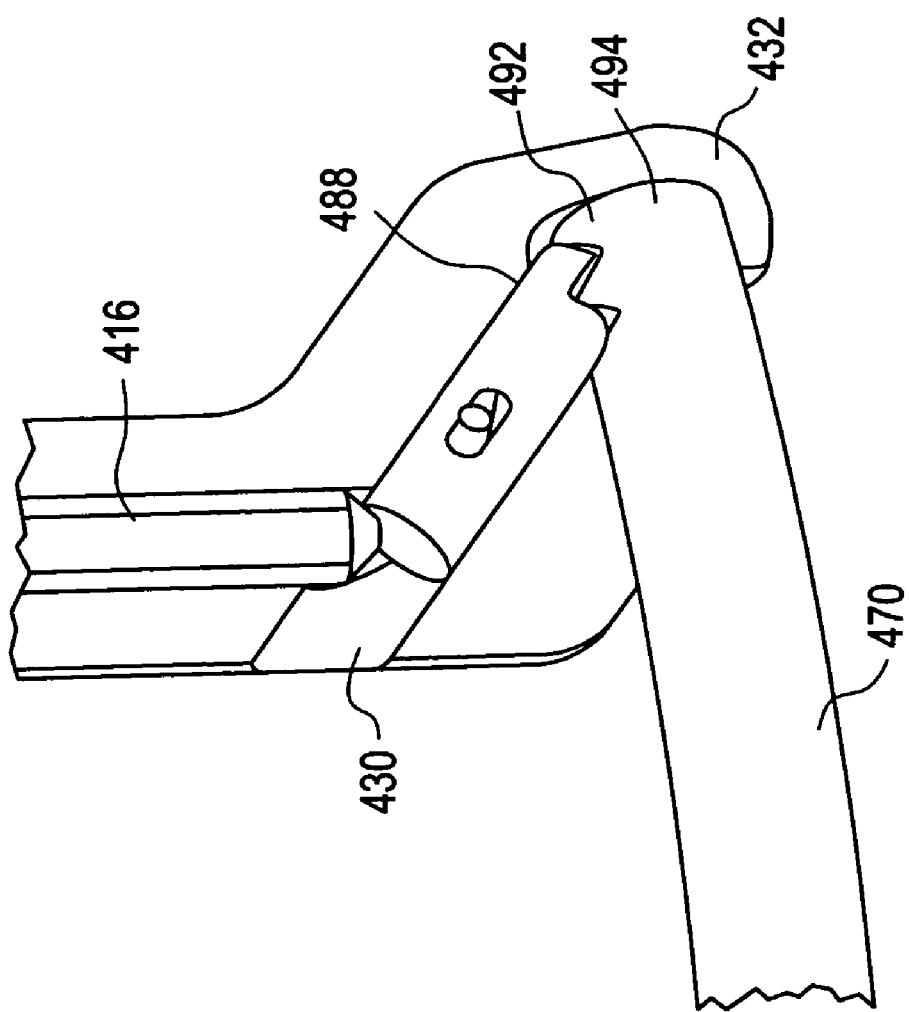
FIGS. 38B and 38C are a side elevational views in cross section of an alternate embodiment of a distal end of the shaft of the instrument of FIG. 32A, illustrating the instrument connected to a spinal fixation element.
Figure 38C:
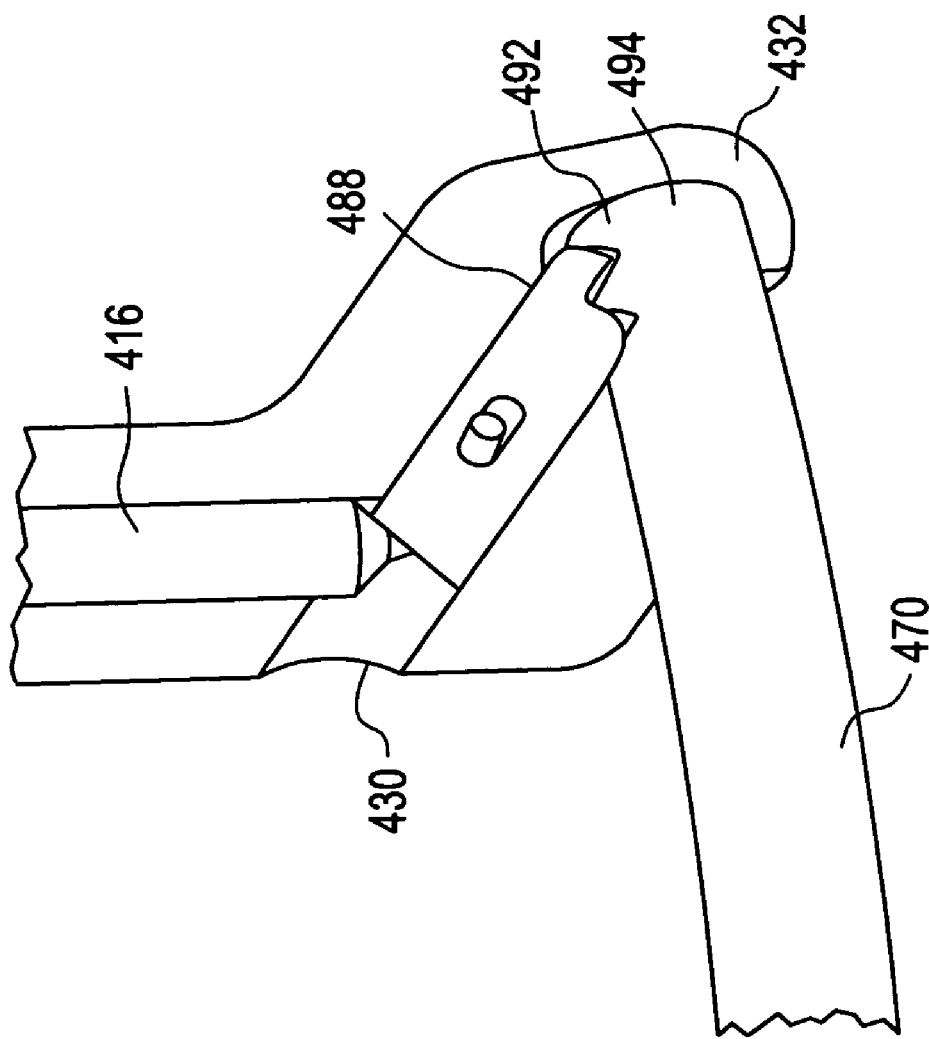
Figure 38D:
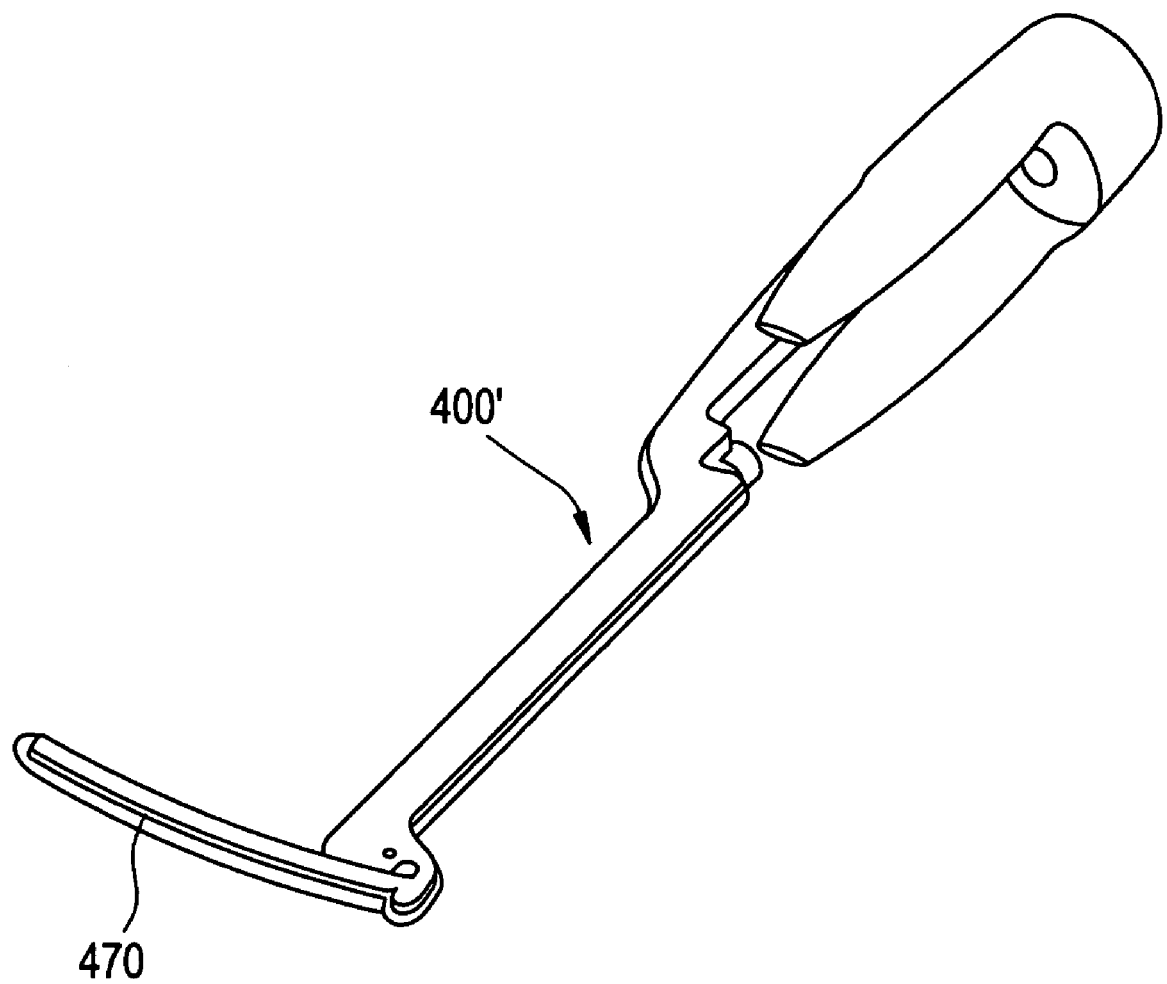
FIG. 38D is a perspective view of an instrument having the distal end illustrated in FIGS. 38B and 38C.

In operation, rotation of the elongate pin 416 in the first direction causes the distal end 426 of the elongate pin 416 to engage the proximal end 436 of the cylindrical component 434 and advance the distal, rod engaging surface 438 of the cylindrical component 434 into engagement with the rod, thereby fixing the rod 470 between the rod engaging surface 438 of the cylindrical component 434 and the rod seat 432, as illustrated in FIG. 38A. Rotation of the elongate pin 416 in the second direction causes the rod engaging surface 438 to be displaced away from the rod 470, to facilitate removal of the rod. In certain exemplary embodiments, a spring or other biasing mechanism may be provided to bias the cylindrical component 434, and/or the elongate pin 416, in a proximal or distal orientation. In the illustrated embodiment, for example, a spring may be provided to bias the rod engaging surface 438 of the cylindrical component 434 distally into engagement with the rod 470. Alternately, the elongated pin 416 may be rotatably connected to the cylindrical component 434 so that rotation of the pin 416 retracts the cylindrical component 434 away from the rod.

Figure 39:
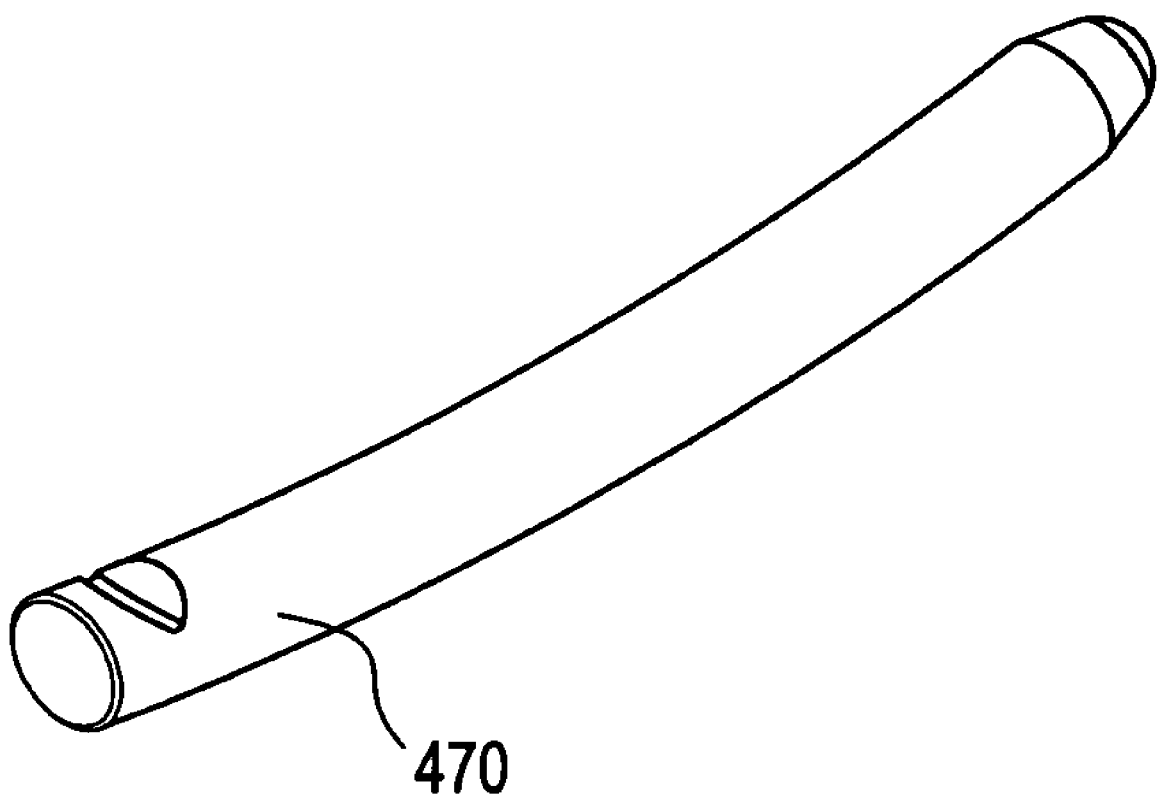
FIG. 39 is a perspective view of an exemplary embodiment of a spinal fixation element.

In certain exemplary embodiments, the spinal fixation element may include one or more features to facilitate connection with the instrument. In the illustrated exemplary embodiment, for example, the exemplary spinal rod 470 includes a generally V-shaped notch 472 at the distal end 474 thereof to facilitate engagement of the cylindrical component 434 with the rod 470, as illustrated in FIG. 39. An alternate embodiment of an instrument 400' illustrated in FIGS. 38B-38D, the spinal rod 470 includes a generally W-shaped notch 492 at the distal end 494 thereof to facilitate engagement with the complementary W-shaped distal end 488 of the cylindrical component 434.

FIGS. 40-43 illustrate another exemplary embodiment of an instrument 500 for engaging a spinal fixation element, such as a spinal rod 570, and manipulating the spinal fixation element through a cannula, such as a percutaneous access device described above. In the illustrated exemplary embodiment, the instrument 500 includes a handle 502 and an instrument shaft 504. The handle 502 may be configured in a manner analogous to the instrument 80 described above and may be connected to the instrument shaft 504 by one or more fasteners. In alternative exemplary embodiments, the handle and shaft may be of unitary construction.

The instrument shaft 504 of the exemplary instrument 500 may include a lumen 514 through which an actuation mechanism is positioned. In the illustrated exemplary embodiment, the actuation mechanism is linkage 550 positioned in the lumen 414. The linkage 550 comprises multiple links 552 positioned within the lumen 514 and a proximal handle 554 connected to a proximal link 552A. In the illustrated exemplary embodiment, the linkage 550 includes three pivotably connected links—first link 552A, second link 552B, and third link 552C. The links 552 cooperate to move within the lumen 514 to adjust the position of the rod engaging mechanism described below. Pivoting the linkage handle 554 from a first position, illustrated in FIG. 42A, in which the linkage handle 554 is oriented generally perpendicular to the longitudinal axis of the instrument shaft 504, to a second position, illustrated in FIG. 42B, causes the third link 552C to advance distally. One skilled in the art will appreciate that the number of links provided may be varied depending on, for example, the length of instrument shaft 504.

The distal end 528 of the instrument shaft 504 is configured to house a spinal fixation element engaging mechanism and to seat the spinal fixation element, which in the illustrated embodiment is a spinal rod 570. In the illustrated exemplary embodiment, the distal end 528 of the instrument shaft 504 is oriented generally transverse to the longitudinal axis and includes a housing for the rod engaging mechanism. In the illustrated exemplary embodiment, the distal end 528 of the instrument shaft 504 includes a rod seat 532. The rod engaging mechanism, in the illustrated exemplary embodiment, is a generally block shaped component 534 that is pivotable about a pivot axis defined by a pivot pin 536. The block shaped component 534 includes a first surface 538 and a second, rod engaging surface 540.

Figure 40:
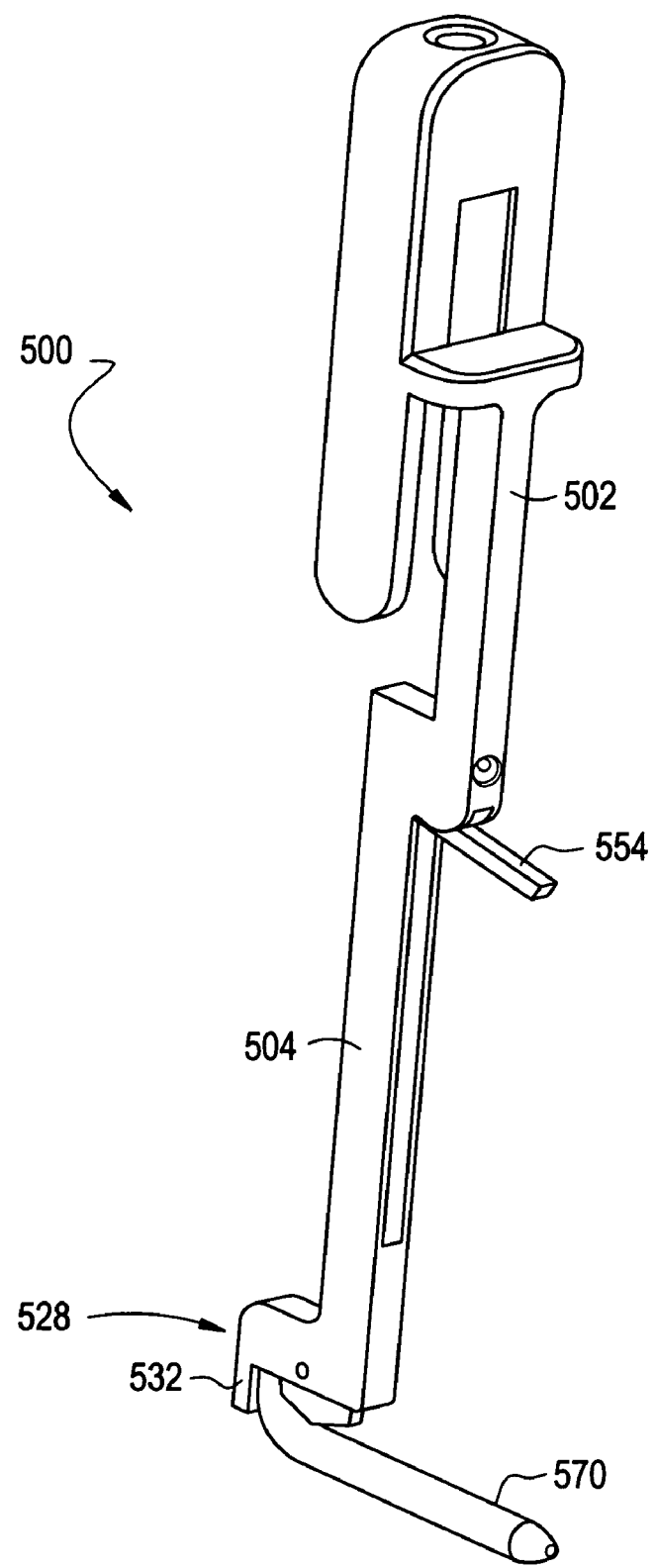
FIG. 40 is a perspective view of another exemplary embodiment of an instrument for engaging a spinal fixation element, illustrating the instrument connected to a spinal fixation element.
Figure 41:
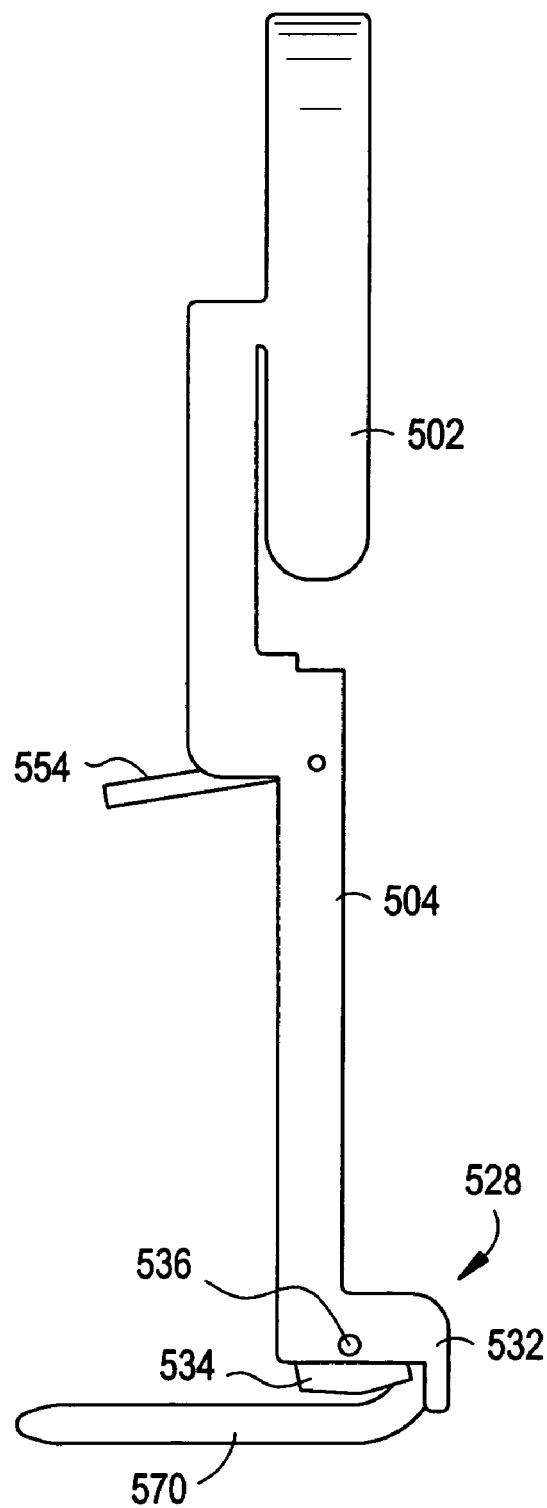
FIG. 41 is a side elevational view of the instrument of FIG. 40.
Figure 43:
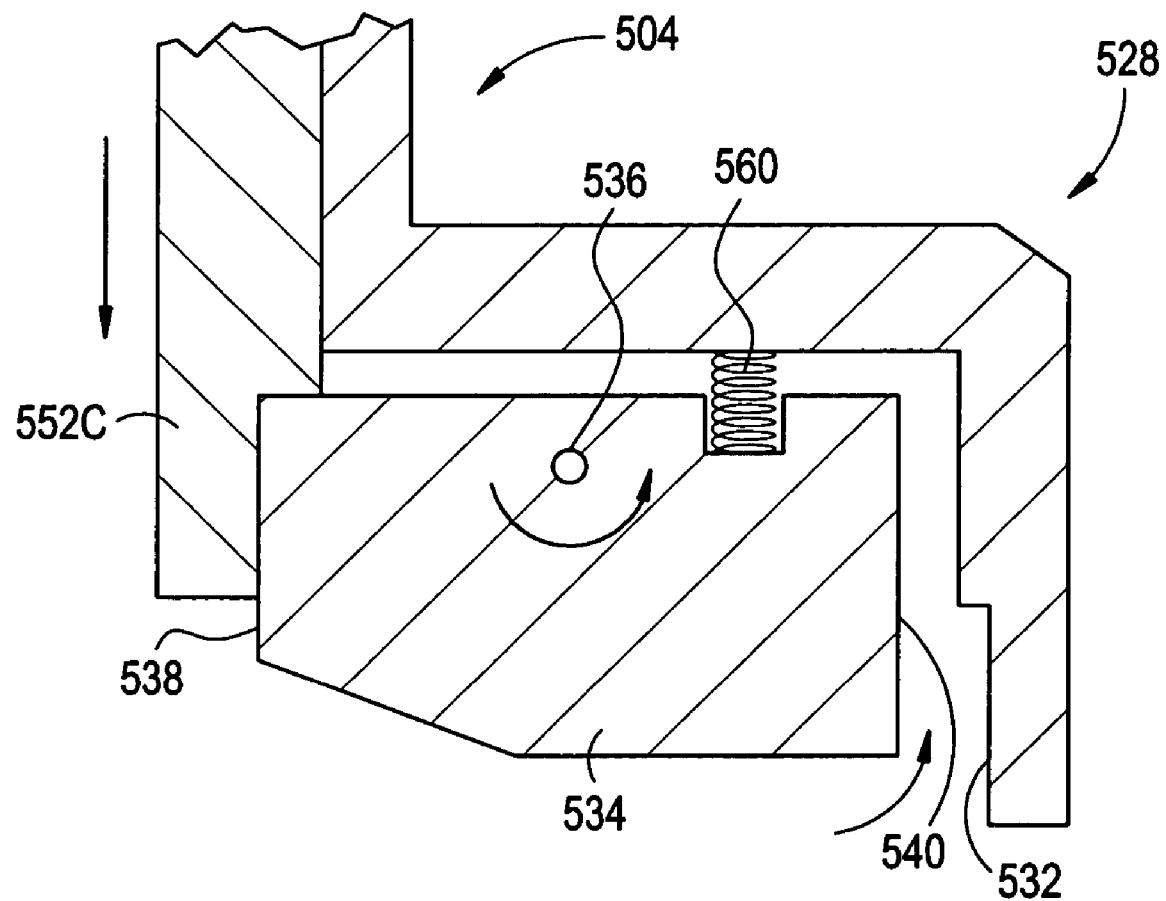
FIG. 43 is a side elevational view in cross section of the distal end instrument of FIG. 40, illustrating operation of the rod engaging mechanism of the instrument.

In operation, pivoting of the linkage handle 554 from the first position to the second position causes the third link 552C of the linkage 550 to advance distally in the lumen 514 and engage the first surface 538 of the component 534. As the link 552C is advanced the distally, the component 534 pivots causing the rod engaging surface 534 of the component 550 to engage the rod, thereby fixing the rod 570 between the rod engaging surface 540 and the rod seat 532, as illustrated in FIG. 40. In certain exemplary embodiments, a spring or other biasing mechanism may be provided to bias the component 534, and/or the linkage 550, in a particular orientation. In the illustrated embodiment, for example, a spring 560 may be provided to bias the rod engaging surface 538 of the component 534 away from the rod seat 532.

Figure 29:
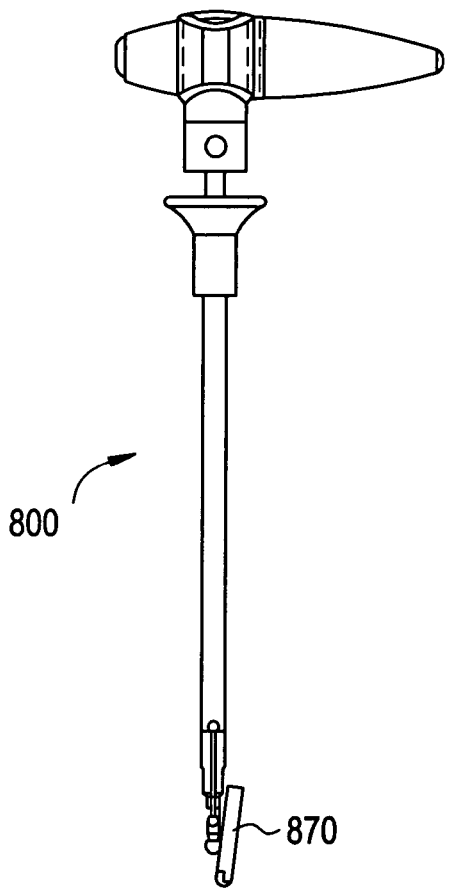
FIGS. 29-31 illustrate another exemplary embodiment of an instrument for engaging a spinal fixation element, the exemplary instrument engaging the spinal fixation element to facilitate articulation of the spinal fixation element.
Figure 30:
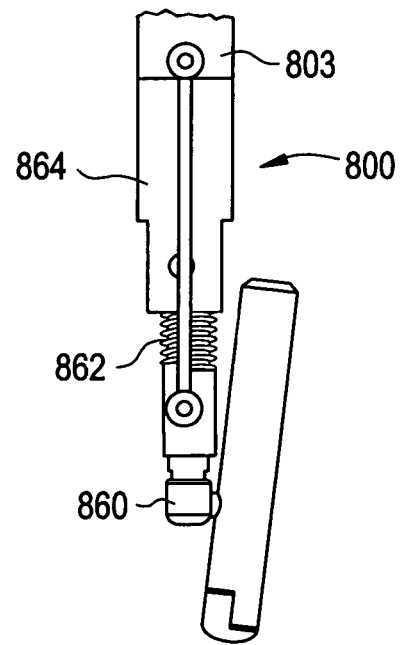
Figure 31:
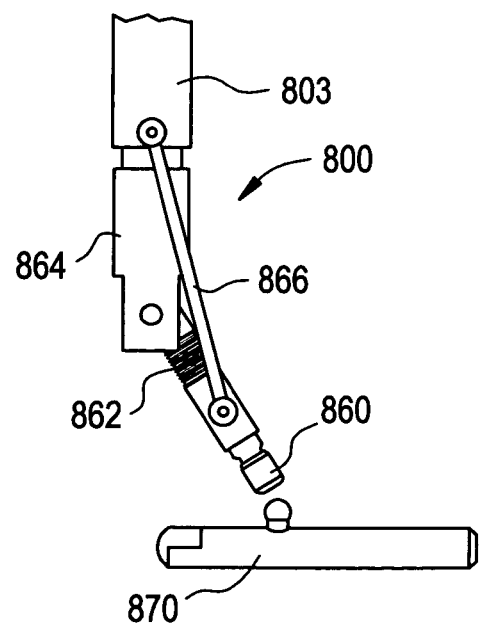
Figure 32A:
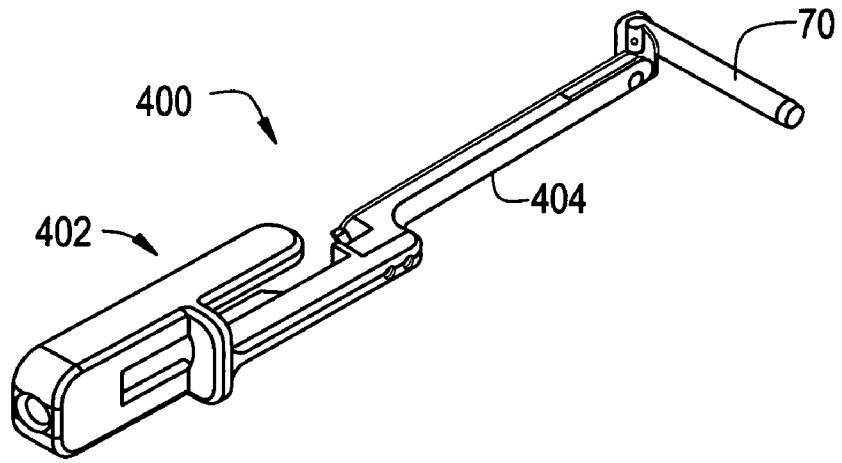
FIG. 32A is a perspective view of another exemplary embodiment of an instrument for engaging a spinal fixation element, illustrating the instrument connected to a spinal rod.
Figure 32B:
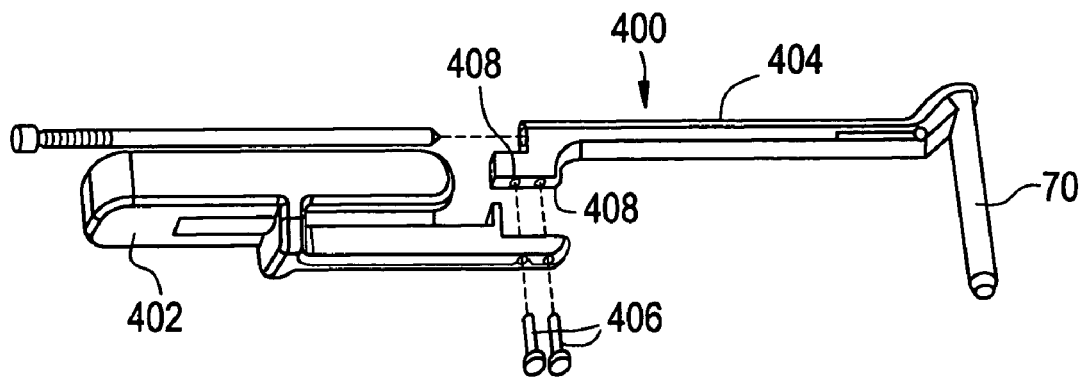
FIG. 32B is an exploded perspective view of the instrument of FIG. 32A.
Figure 33A:
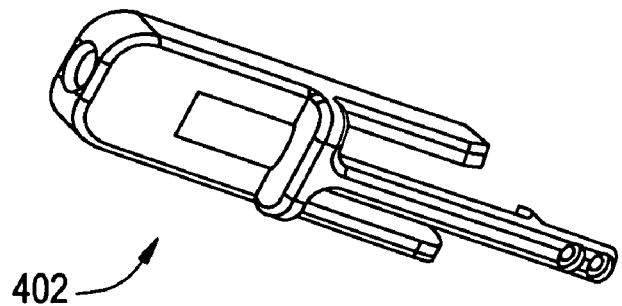
FIG. 33A is a front perspective view of the handle of the instrument of FIG. 32A.
Figure 32C:
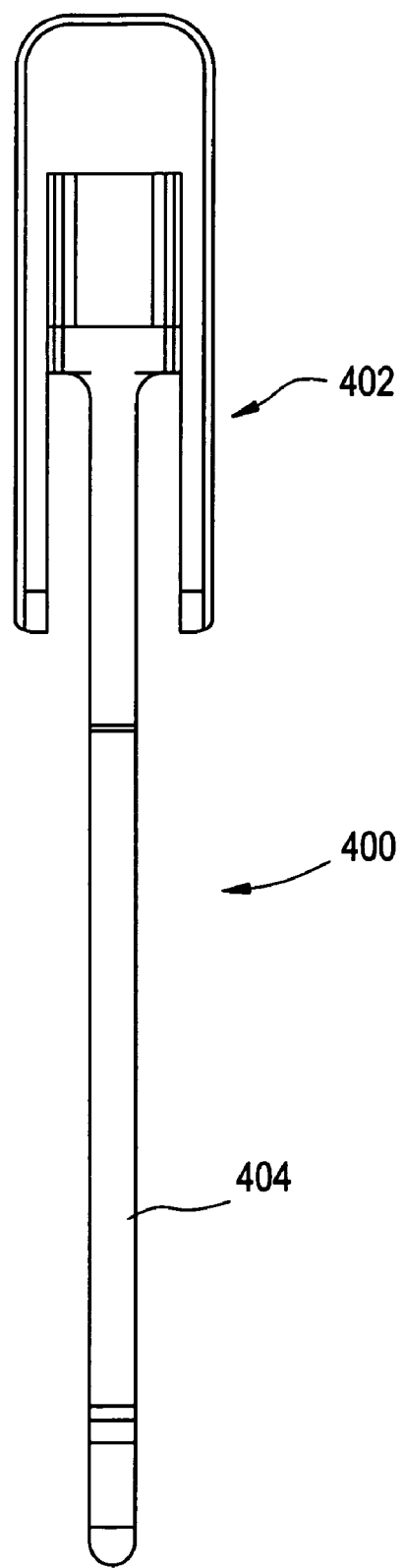
FIG. 32C is a rear elevation view of the instrument of FIG. 32A.
Figure 33B:
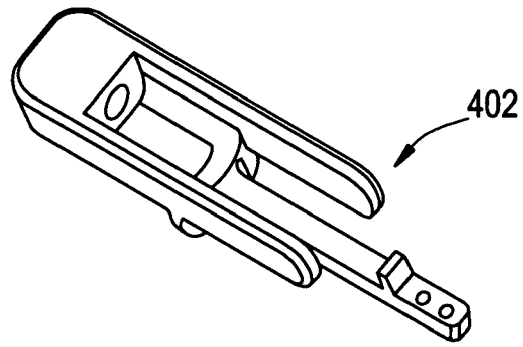
FIG. 33B is a rear perspective view of the handle of the instrument of FIG. 32A.
Figure 33C:
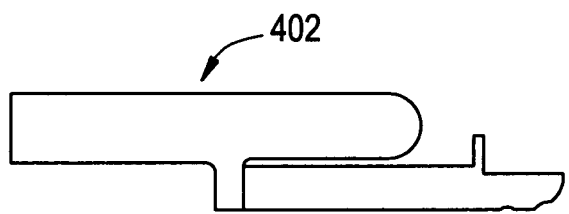
FIG. 33C is a side elevational view of the handle of the instrument of FIG. 32A.
Figure 34A:
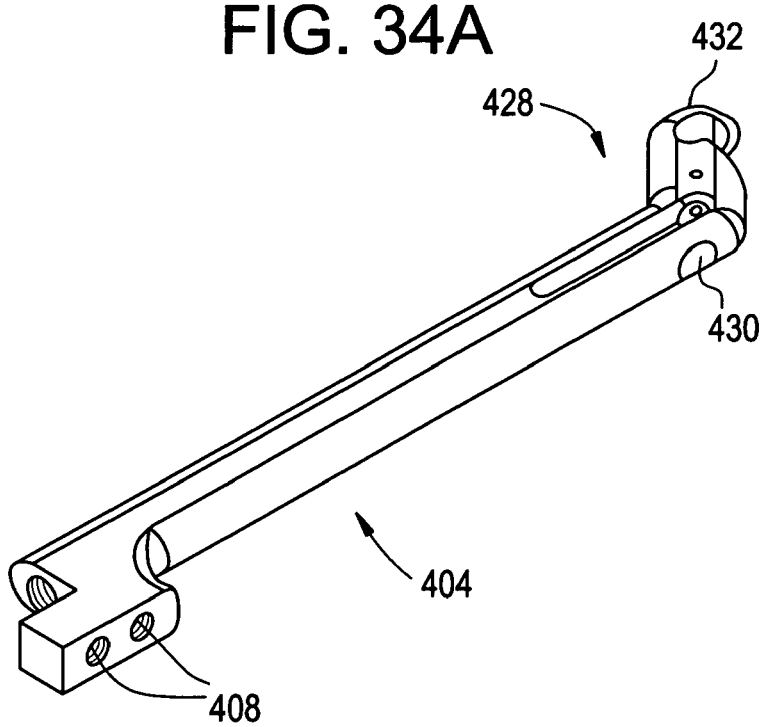
FIG. 34A is a perspective view of the shaft of the instrument of FIG. 32A.
Figure 34B:
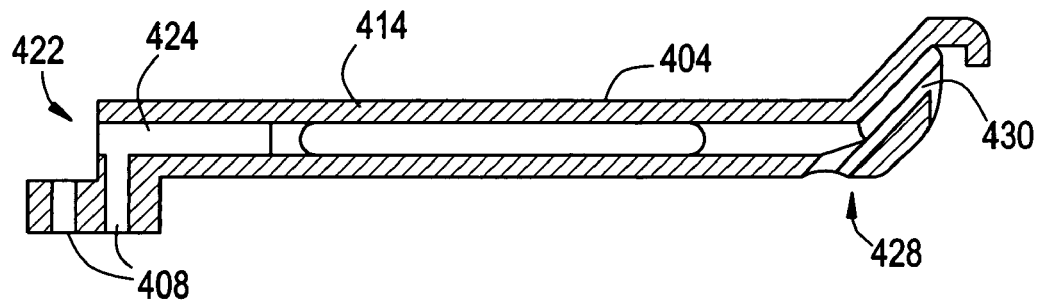
FIG. 34B is a side elevation view in cross section of the shaft of the instrument of FIG. 32A.
Figure 35A:
FIG. 35A is a side elevational view of the elongated pin of the instrument of FIG. 32A.
Figure 35B:
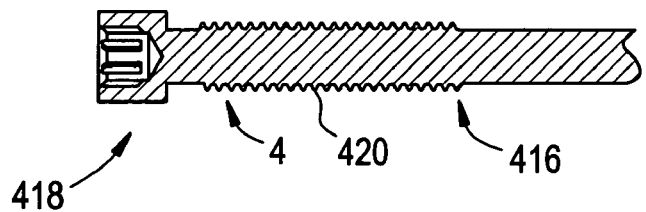
FIG. 35B is a side elevational view in cross section of the proximal end of the elongated pin of the instrument of FIG. 32A.
Figure 36:
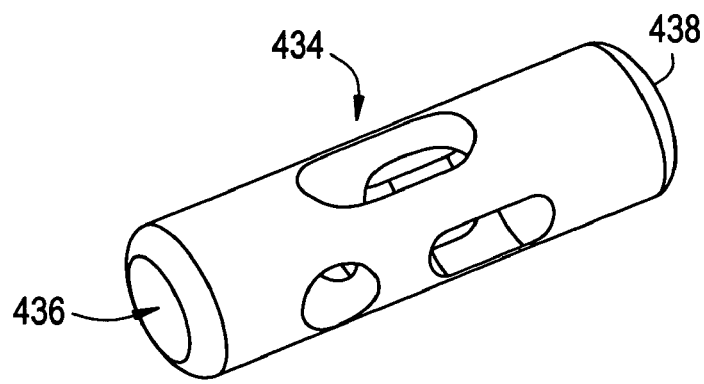
FIG. 36 is a perspective view of the rod engagement mechanism of the instrument of FIG. 32A.
Figure 37:
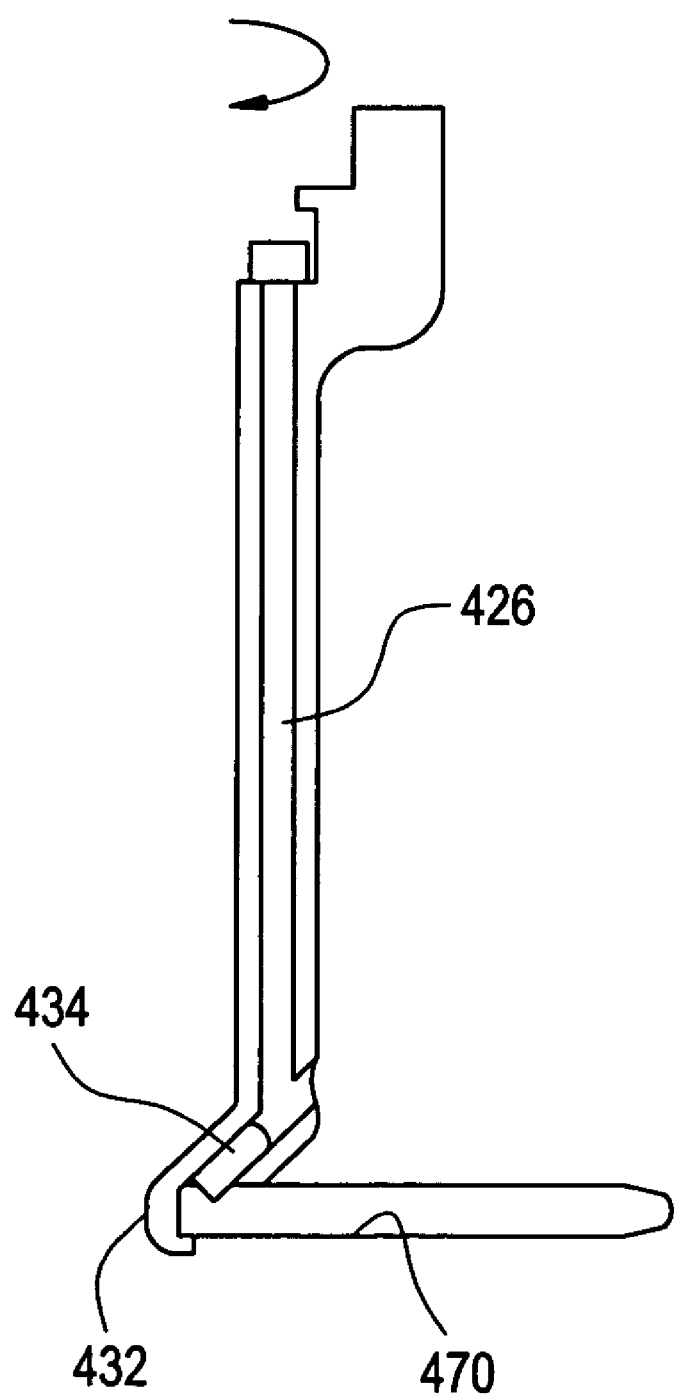
FIG. 37 is a side elevational view in cross section of the shaft of the instrument of FIG. 32A, illustrating the operation of the instrument.

In an alternate embodiment, it may be desirable for the engagement between the instrument and the spinal fixation element to change the orientation of the spinal fixation element with respect to the instrument shaft during the procedure. This embodiment of the instrument has an articulating engagement that allows for manipulation of the fixation element from an orientation parallel with the instrument shaft to an orientation perpendicular to the shaft during the procedure. An example of an instrument allowing these movements is disclosed U.S. Patent Application Publication No. US2005/0131419 A1, entitled "Pivoting Implant Holder" and U.S. Patent Application Publication No. US2005/0131420 A1, entitled "Pivoting Implant Holder," each of which are incorporated by reference in their entirety herein. Another embodiment of an instrument 800 having an articulating engagement with the spinal fixation element is shown in FIGS. 29-30. The instrument 800 engages a projection 872 on a spinal fixation element, shown as a spinal rod 870, by a collet 860 extending by a spring 862 from the distal end of the instrument shaft 803. A locking sleeve 864 locks the projection 872 of the rod 870 within the collet 860. Articulation of the rod 870 is provided by two linking arms 866 extending from the shaft 803 to the collet 860, which allow the rod 870 to rotate or pivot.

For reference purposes, FIG. 1 illustrates an exemplary spinal anchor for use with the methods and devices of the present invention. A person skilled in the art will appreciate that a variety of anchors can be used with the devices and methods of the present invention, including, for example, spinal screws, hooks, bolts, and wires. FIG. 1 illustrates a spinal screw that includes a distal, bone-engaging portion, e.g., a threaded shank 54, and a proximal, U-shaped, receiver member head 52 that is adapted to seat a spinal fixation element, for example a spinal rod. The threaded shank 54 can be fixedly attached to the receiver head 52 to form a monoaxial screw, or alternatively the shank 54 can be configured as a polyaxial screw, as shown, that is rotatably disposed through an opening formed in the distal end of the receiver head 52 to allow rotation of the shank 54 with respect to the receiver head 52. A variety of techniques can be used to allow rotation of the head 52 with respect to the shank 54.

FIGS. 12-17 show a minimally invasive method of implanting a spinal fixation element. While the method is shown and described in connection with the percutaneous access device 12 (FIG. 1), percutaneous access device 212 (FIG. 3), and spinal screw 50 disclosed herein, a person skilled in the art will appreciate that the method is not limited to use with such devices, and that a variety of other devices described herein and known in the art can be used. Moreover, while only two access devices 12, 212 and two anchors 50, 50' are shown in FIGS. 12-17, the method of the present invention can be performed using any number of access devices and anchors. The method can also be performed using only some of the method steps disclosed herein, and/or using other methods known in the art.

An example of a procedure for placing the spinal anchors and percutaneous access devices is disclosed in U.S. Patent Application Publication No. US 2005/0131421 A1, entitled "Methods and Devices for Minimally Invasive Spinal Fixation Element Placement," which is incorporated herein by reference. After the anchors 50, 50' are implanted with the percutaneous access devices attached, a spinal fixation element 70 may be delivered to the anchor site as described below.

Figure 12:
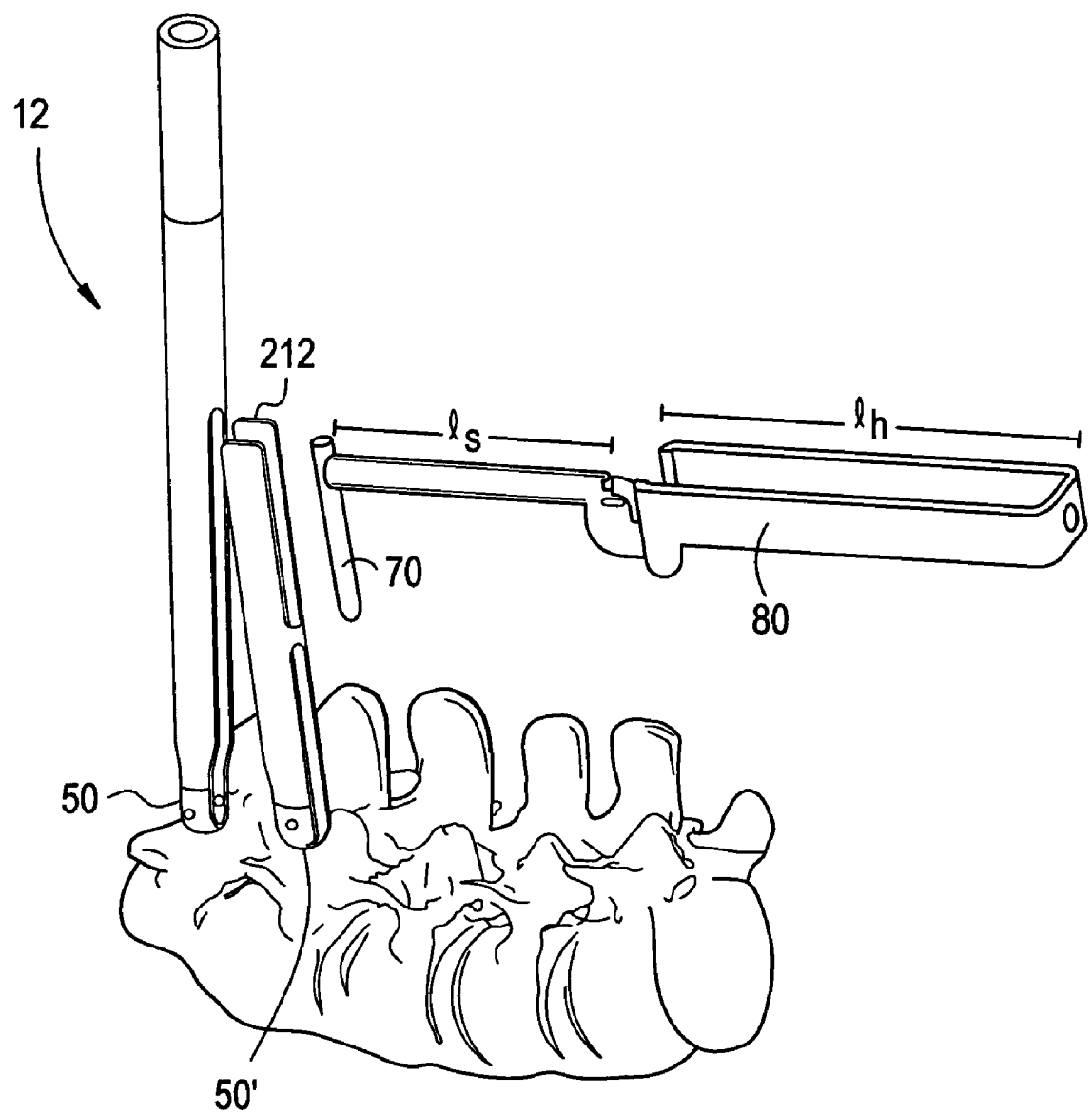
FIGS. 12-17 illustrate a method of inserting a spinal fixation element through the percutaneous access devices shown in FIGS. 1-4.
Figure 13:
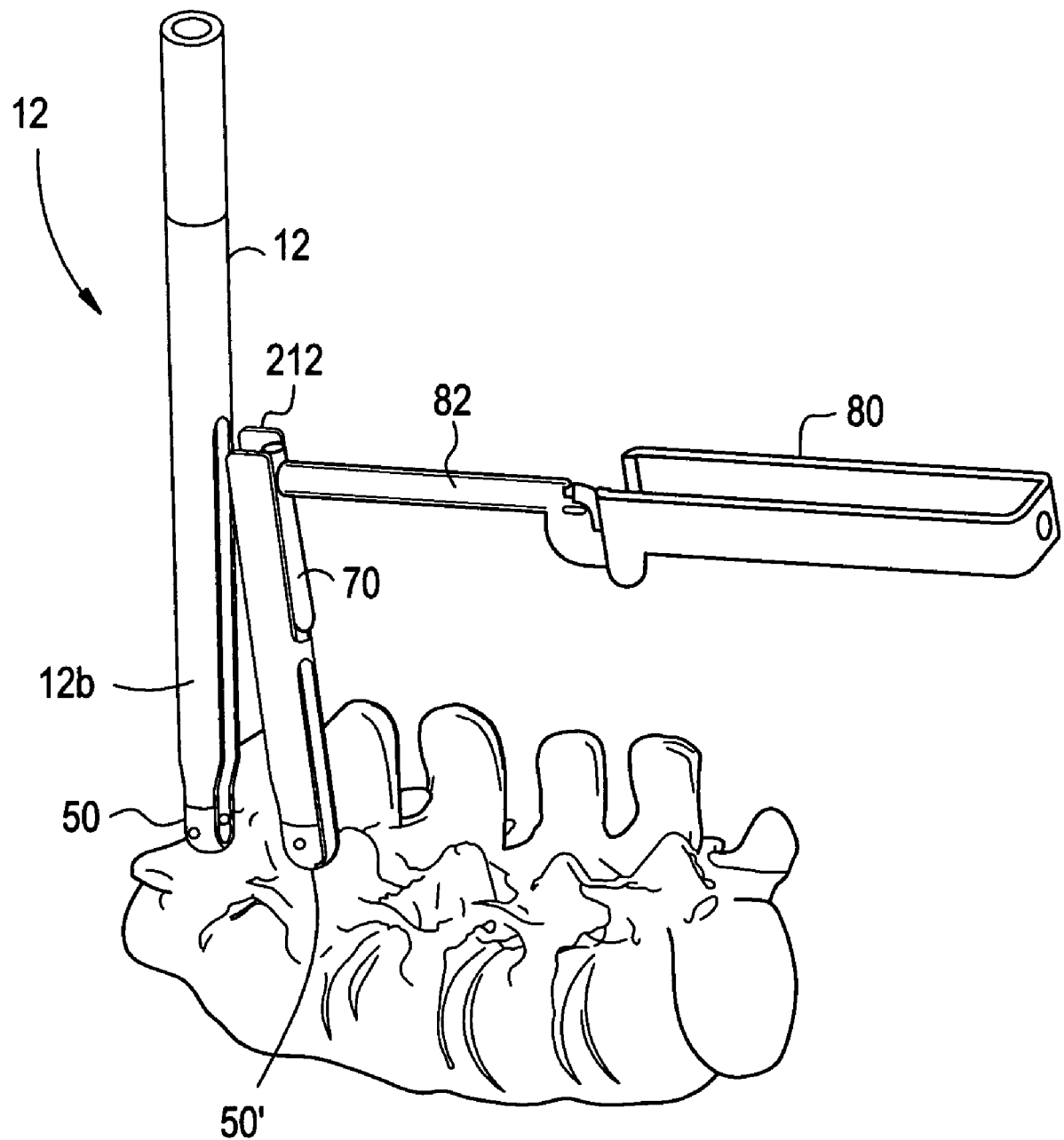
Figure 14:
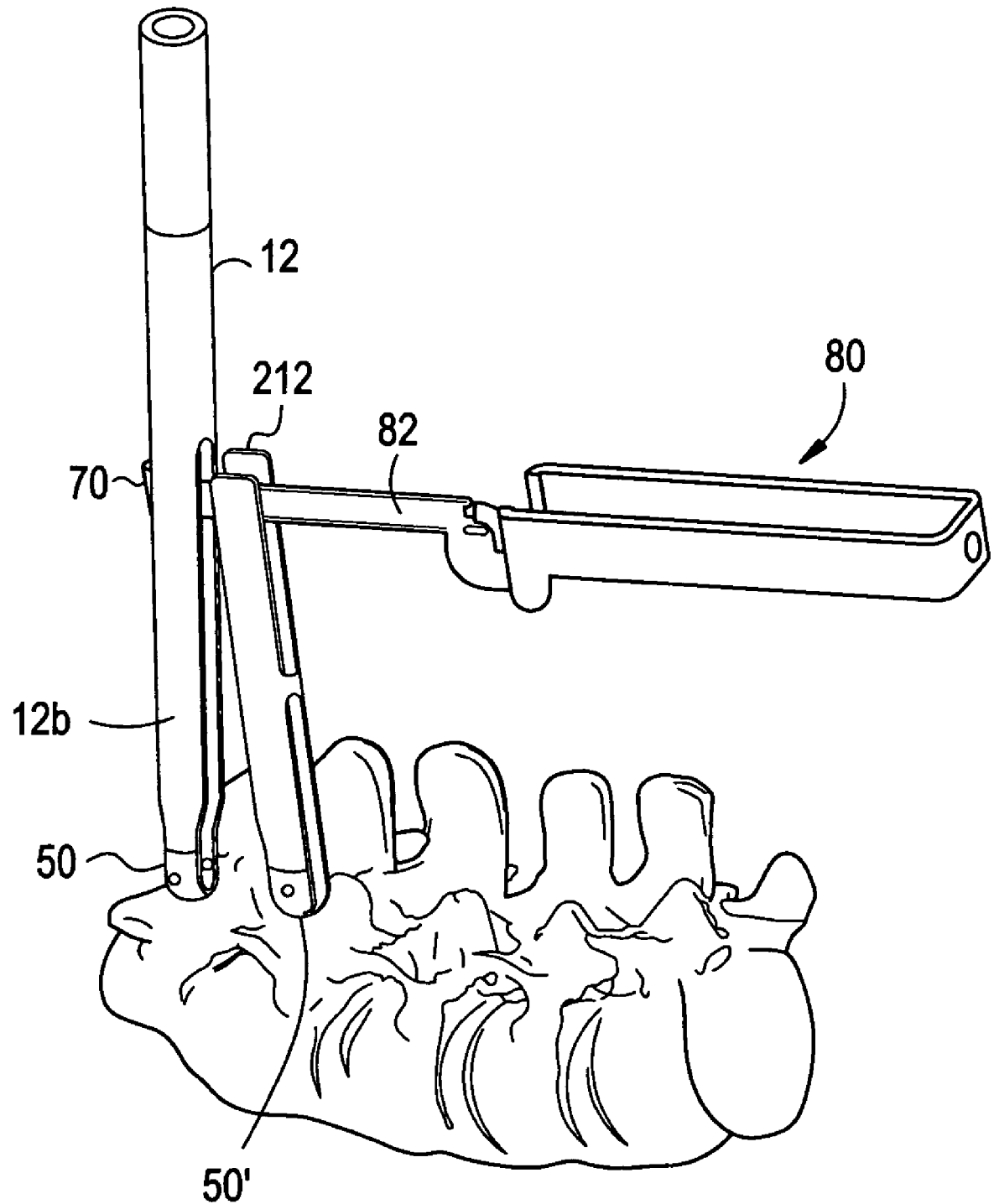

In accordance with one exemplary method, an instrument for engaging and manipulating a spinal fixation element, such as the instrument 80 described above, may be connected to a spinal fixation element, e.g., a spinal rod 70, as illustrated in FIG. 12. The shaft 82 of the instrument 80, with the spinal rod 70 engaged at the distal end of the shaft 82, may be positioned through the side wall openings 14b of the percutaneous access device 212 attached to a second bone anchor 50' and through the sidewall opening 14b of the percutaneous access device 12 attached to a first bone anchor 50, as illustrated in FIGS. 13 and 14. The spinal rod 70 may be introduced into percutaneous access device 12 in a first, lengthwise orientation, such that the spinal rod 70 is oriented substantially parallel to the longitudinal axis L of the access device 12. Where the spinal fixation element has a curved orientation or it has some other configuration, it is understood that the fixation element is in the "substantially parallel" orientation when it is positioned lengthwise through the percutaneous access device.

Figure 15:
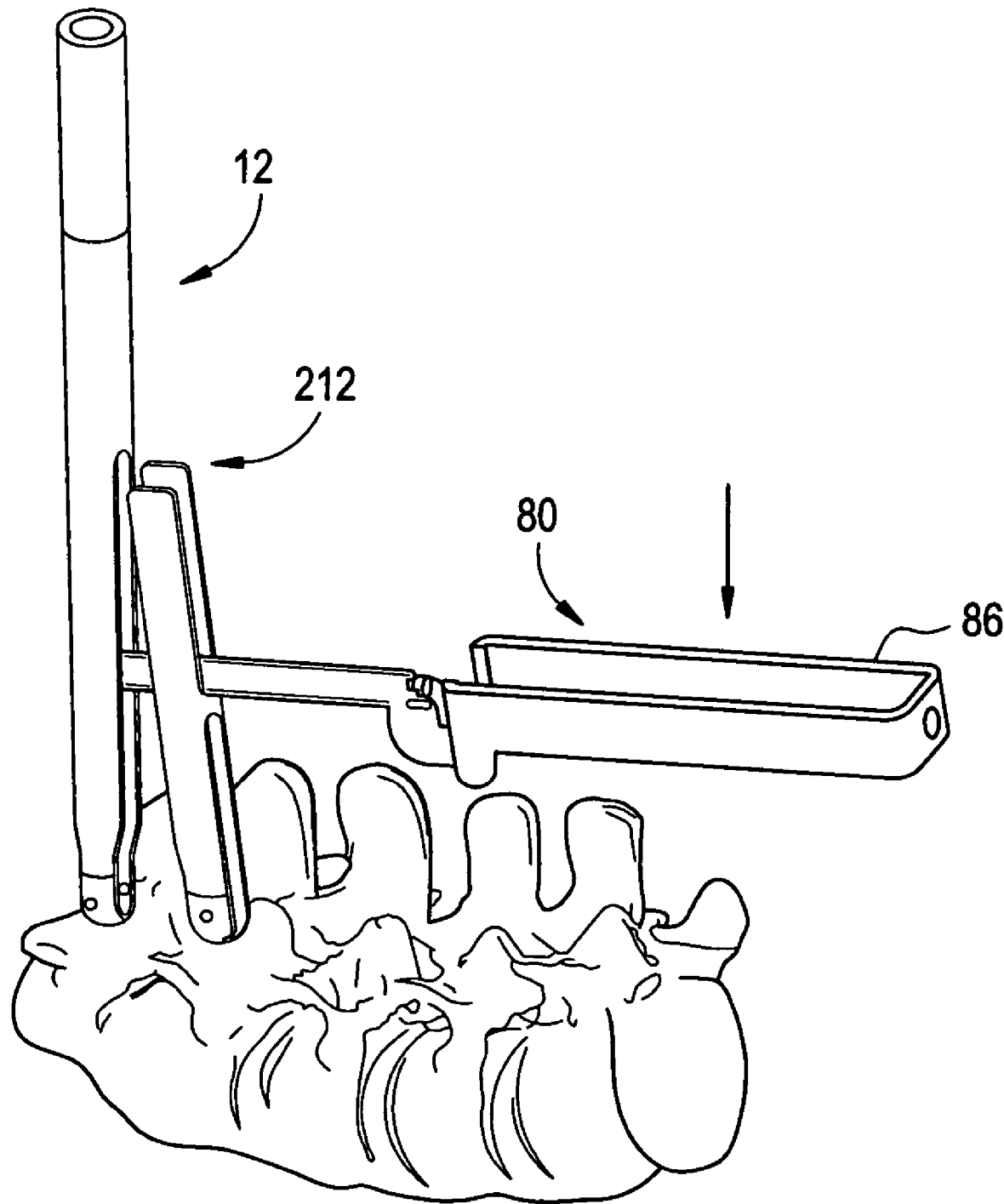
Figure 16:
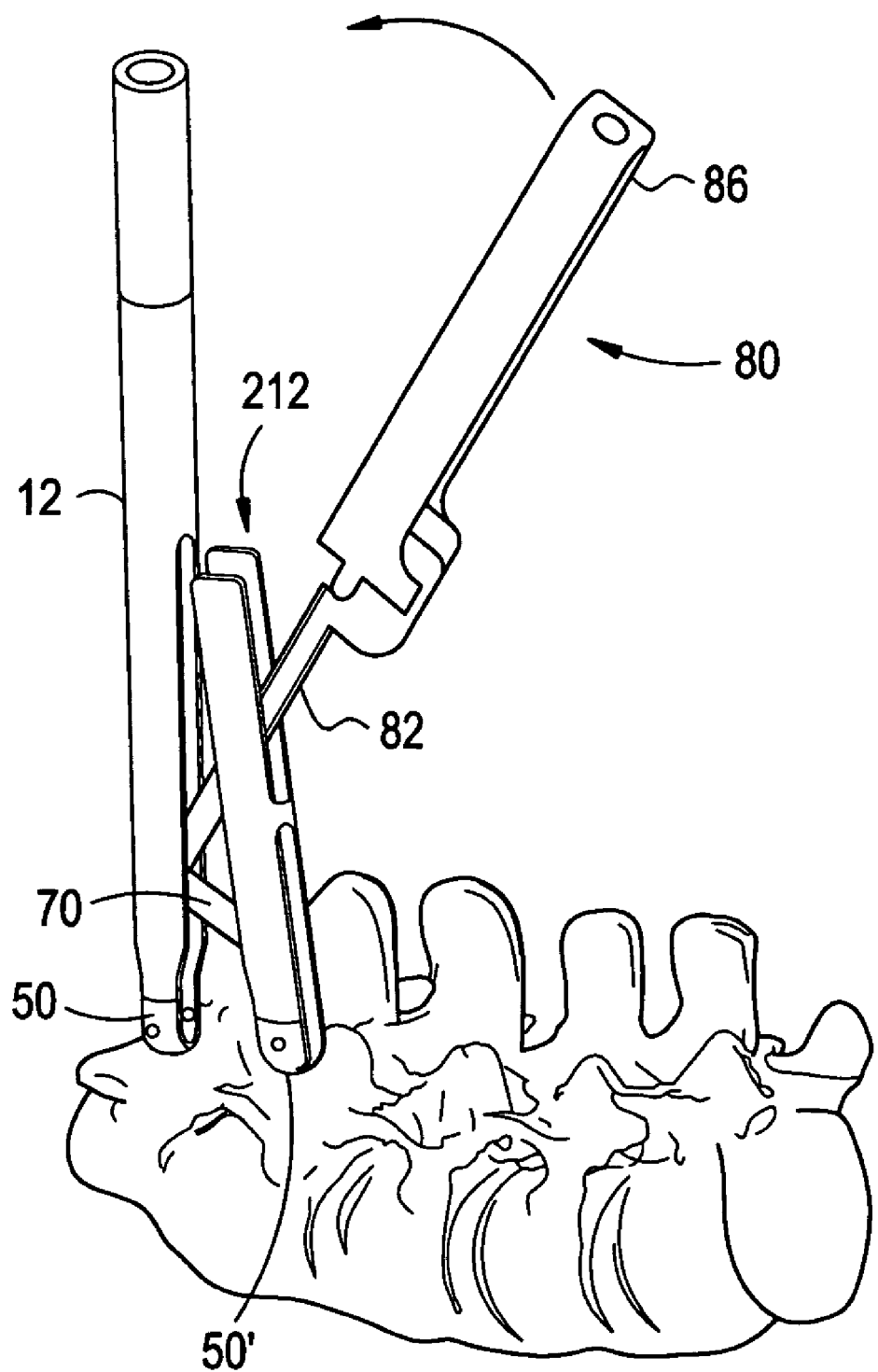
Figure 17:
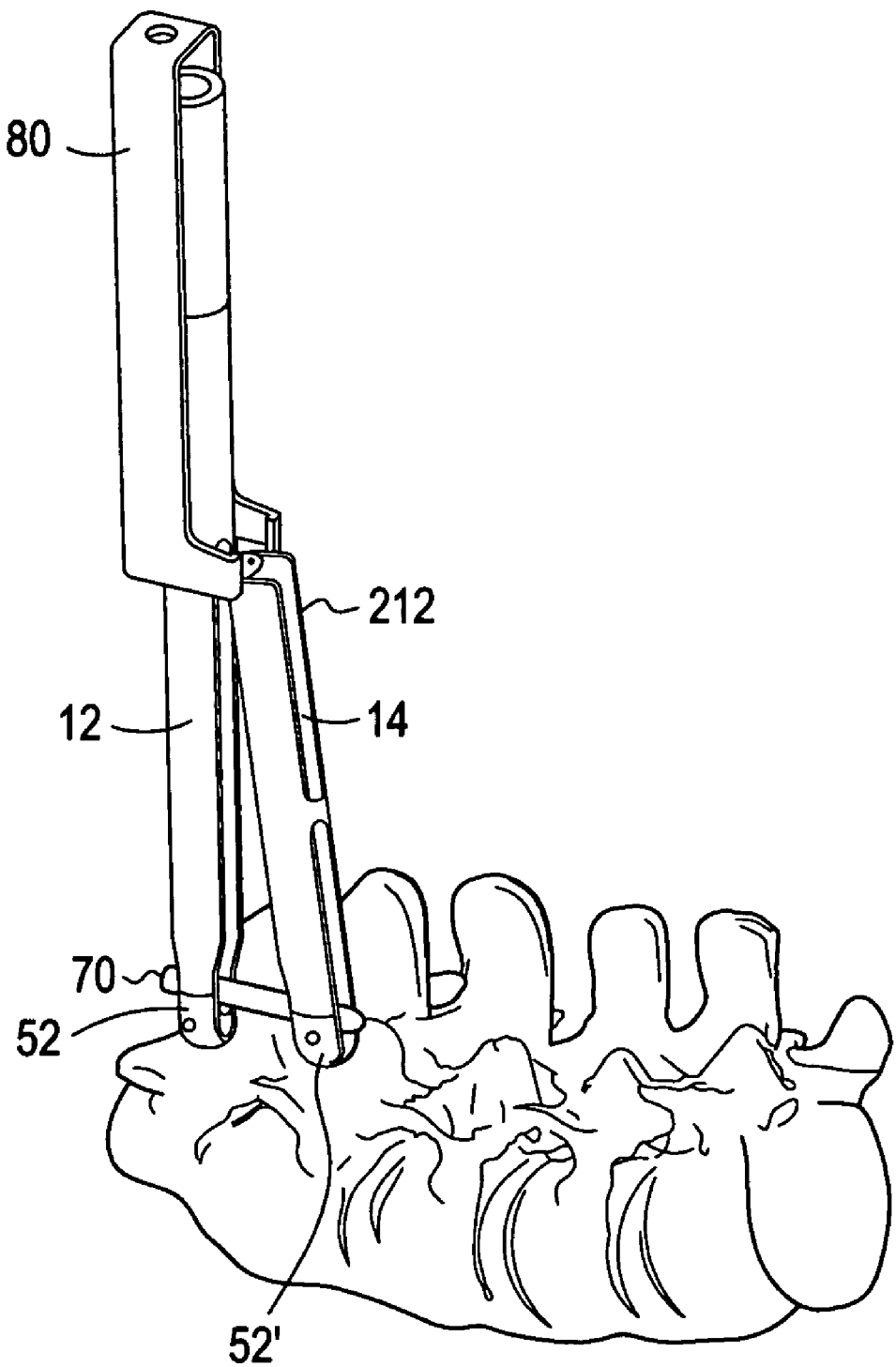

The spinal rod 70 may be moved through the lumen of the percutaneous access device 12 toward the distal end 12b, by moving the handle 86 of the instrument 80 distally, as shown in FIG. 15. Referring now to FIGS. 16 and 17, as the spinal rod 70 approaches the distal end 12b of the access device 12, the orientation of the spinal fixation element 70 can be manipulated to direct it towards the spinal anchor 50' by rotating the handle 86 of the instrument 80 from a position parallel to the patient's spine to a position parallel to the percutaneous access device 12 such that the handle straddles the proximal end of the percutaneous access device 12. Rotating the handle causes the spinal fixation element 70 to assume a second orientation that is different from the first orientation, and that is substantially parallel to the patient's spinal column and/or transverse to the first orientation. As the handle is rotated to straddle the percutaneous access device 12, the shaft 82 of the instrument moves through the proximal sidewall opening 14 of device 212 and exits through the proximal end of the device 212. The shaft 82 of the instrument 80 maintains contact with percutaneous access device 12 until the spinal fixation element 70 has established contact with the distal sidewall opening of percutaneous access device 212. The sizing of the shaft 82 of the instrument 80 aids in keeping the sidewall openings 14 of the percutaneous access devices 12, 212 in alignment while the spinal fixation element 70 is being manipulated into position in relation to the spinal anchors 50, 50'.

It is understood that the angle of the fixation element 70 in the second orientation will vary depending on the type of fixation device being implanted, as well as the orientation of the access device 12, which can vary throughout the surgical procedure since the access device 12 can be positioned at several angles with respect to the patient's spinal column.

During transition of the spinal fixation element 70 from the first orientation to the second orientation, a leading end of the spinal fixation element 70 may be positioned below the fascia layer. Referring to FIGS. 16-17, manipulation of the spinal fixation element 70 is continued until the spinal fixation element 70 is positioned in relation to one or more spinal anchors. Depending on the type of spinal anchor used, the fixation element can be positioned to be directly or indirectly mated to the spinal anchor. As shown in FIG. 17, the fixation element 70 is fully seated in the receiver heads 52, 52' of the adjacent spinal anchors 50, 50'.

A person skilled in the art will appreciate that the spinal fixation element 70 does not need to be directly attached to each anchor 50, 50', and that it can be indirectly attached to the anchors 50, 50' using, for example, a band clamp, or slotted or offset connectors.

Figure 18:
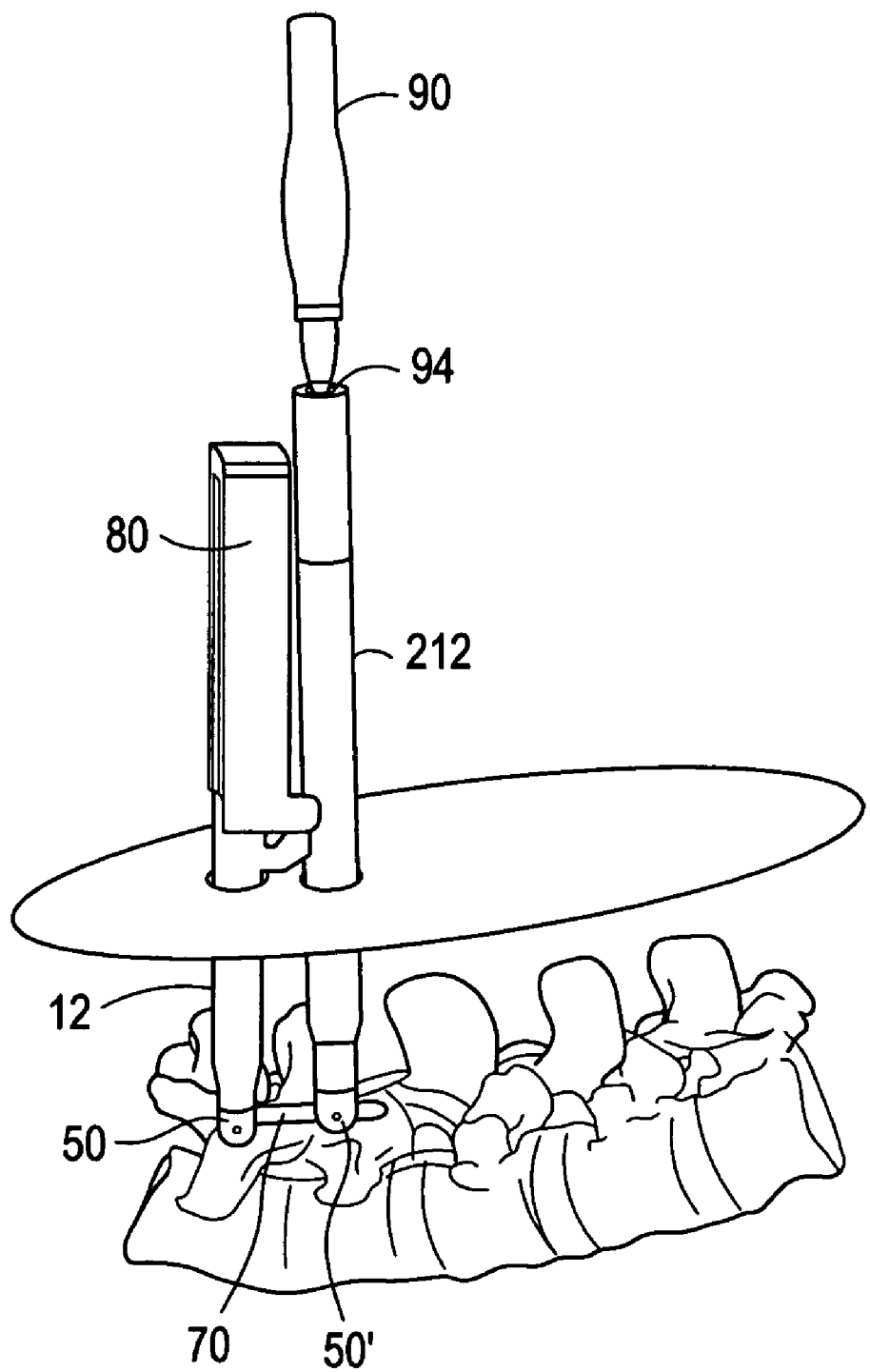
FIGS. 18-19 illustrate an instrument for determining the position of a spinal fixation element relative to a spinal anchor.
Figure 19:
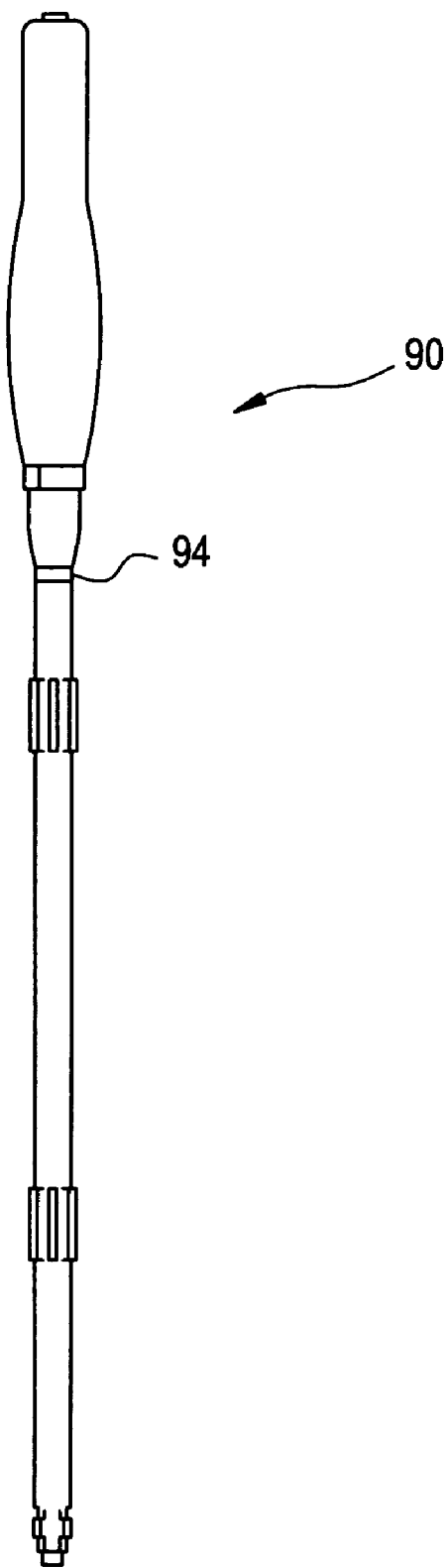
Figure 20:
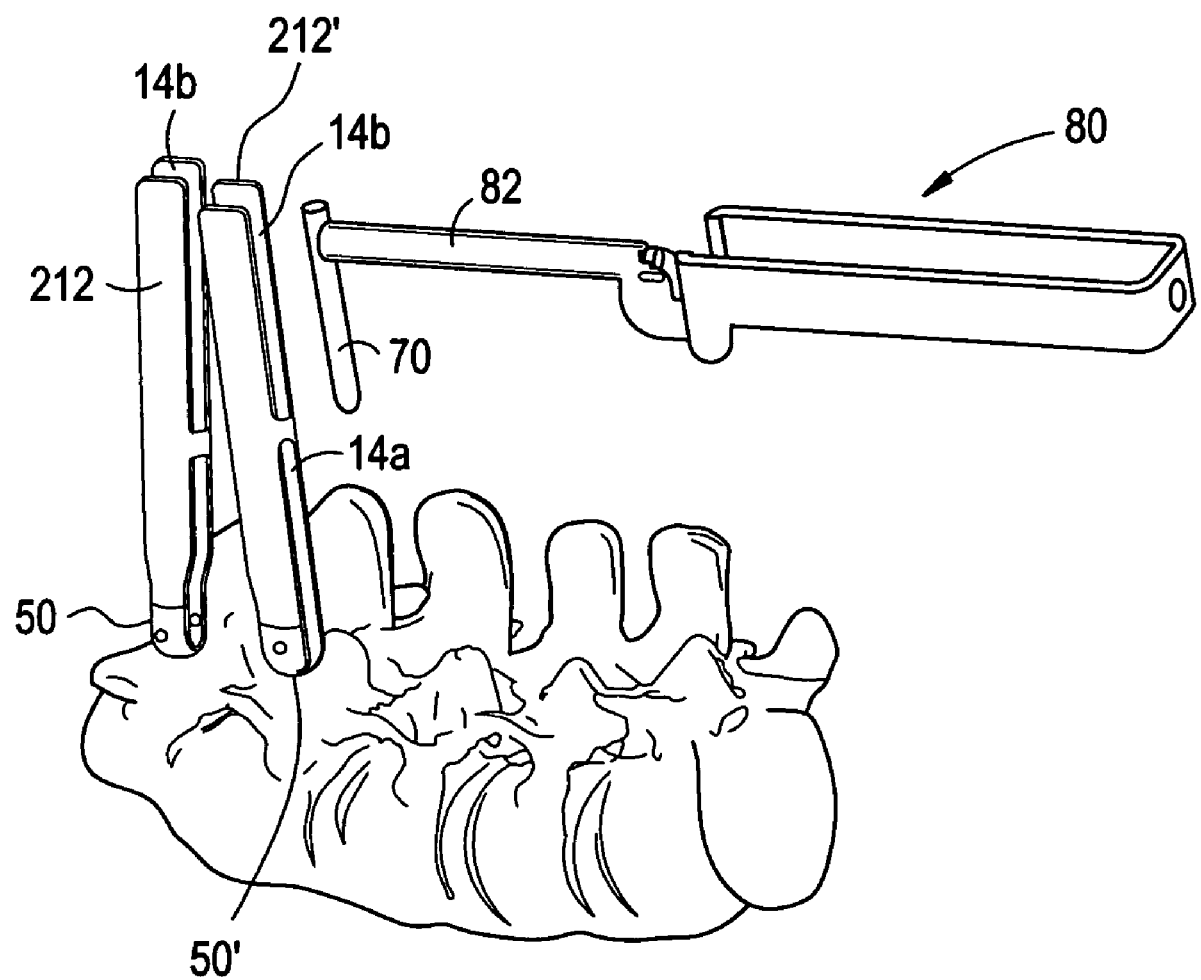
FIGS. 20-25 illustrate a method of inserting a spinal fixation element through the percutaneous access devices shown in FIG. 4.
Figure 21:
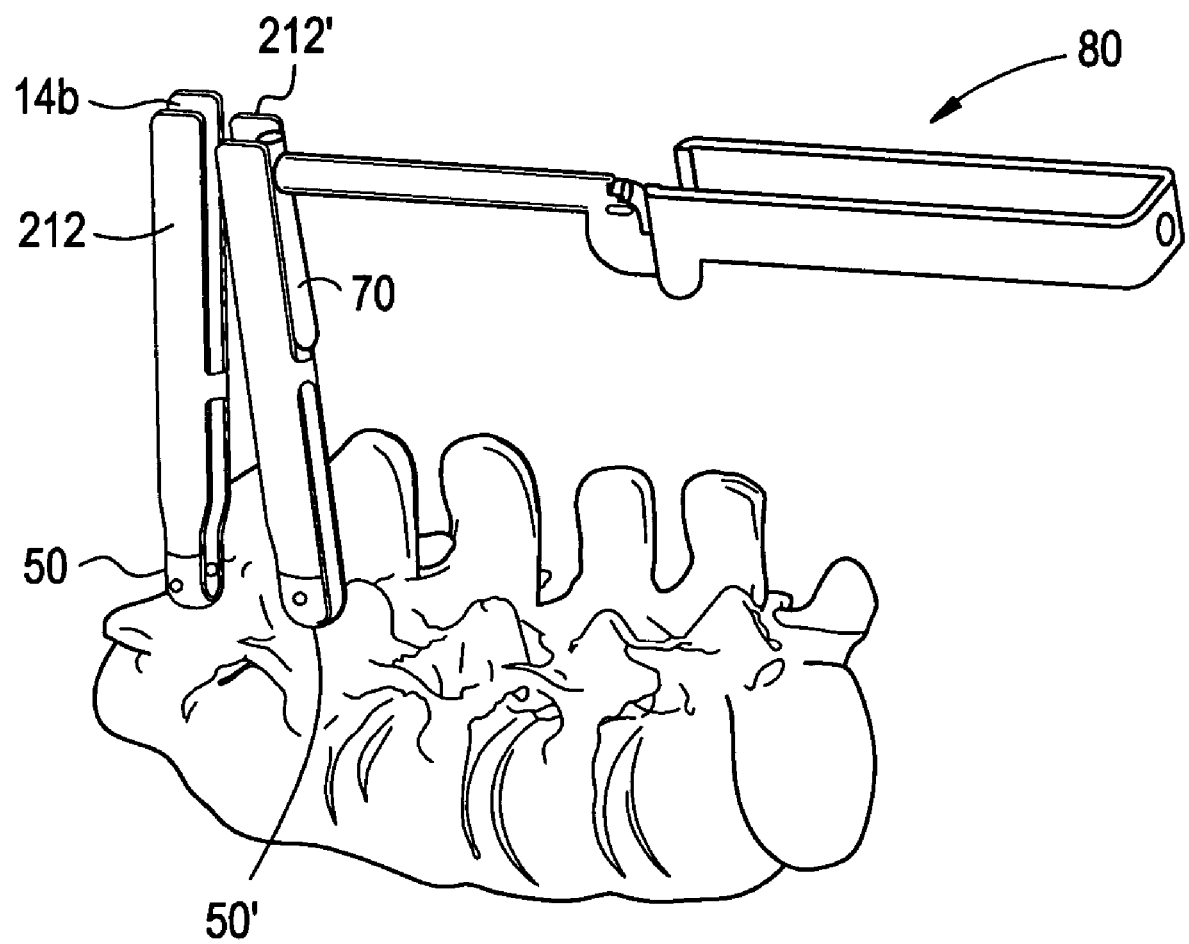
Figure 22:
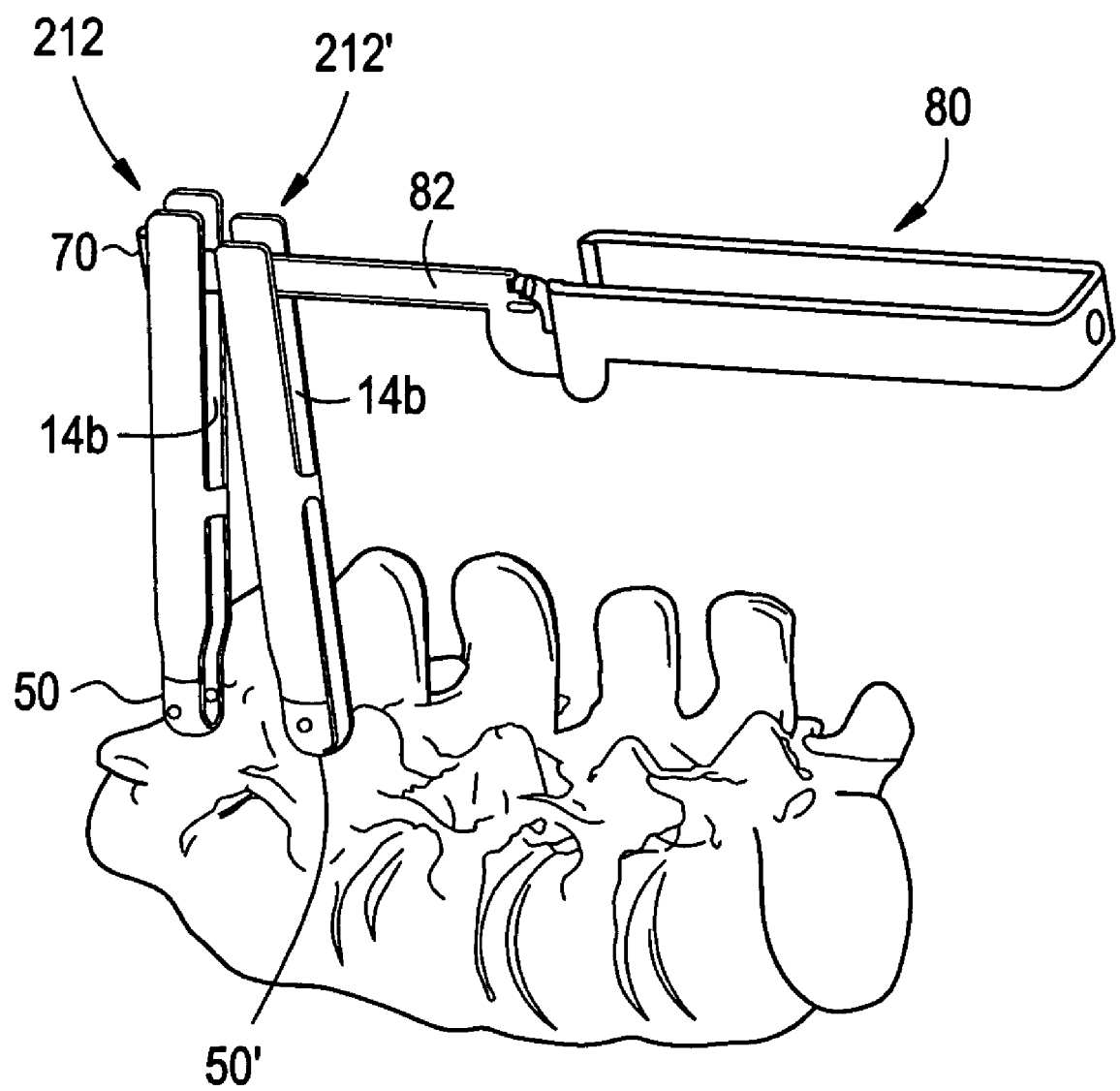
Figure 23:
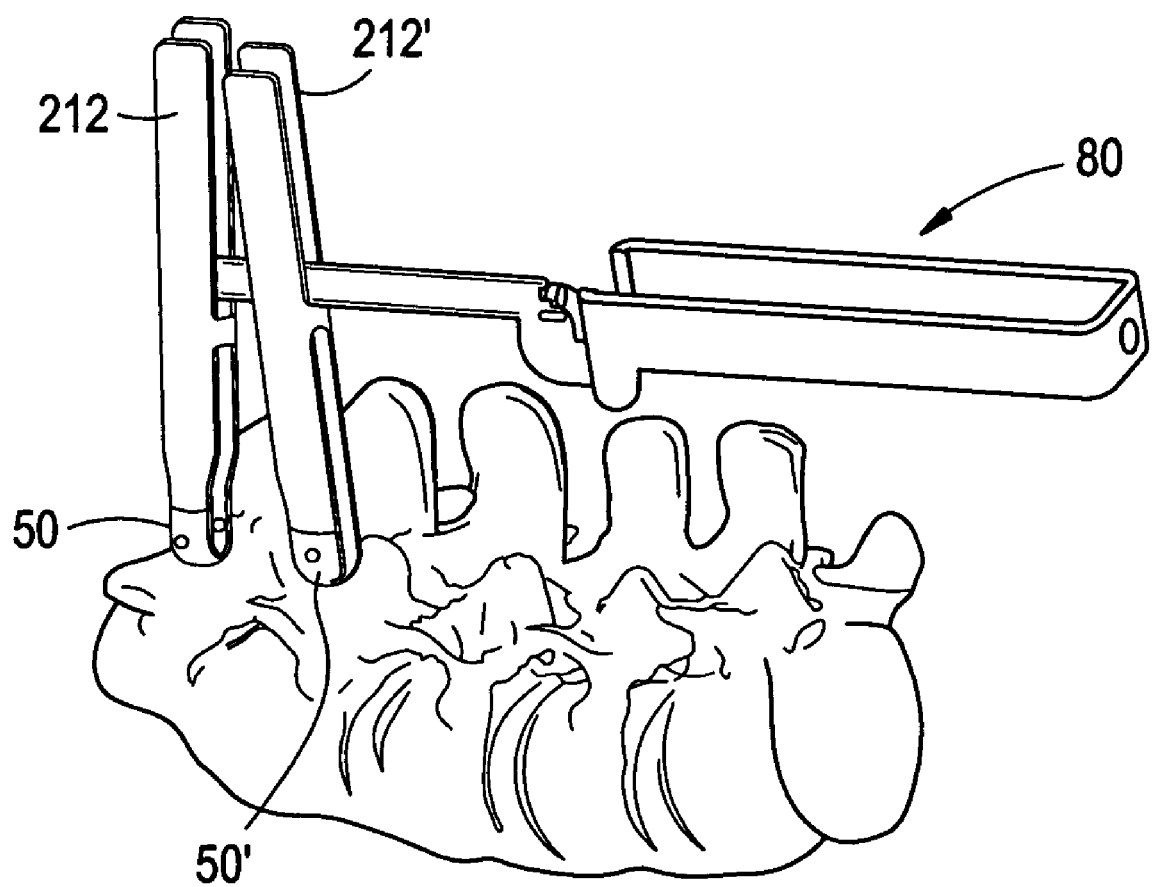

To verify that the spinal fixation element is fully seated in the receiver head of the spinal anchor an instrument 90 can be inserted through the proximal end of the percutaneous access device 12 until it can not be advanced any further, as illustrated in FIGS. 18-19. The proximal end 90a of the instrument has a marker 94 to indicate the depth from the proximal end of the percutaneous access device to the top of a spinal fixation element fully seated in a spinal anchor. If the marker 94 is aligned with the proximal end 12a of the access device, when the instrument is placed down the lumen of the access device, then the spinal fixation element is in the proper position within the spinal anchor and the closure mechanism can be applied, through the access device. The spinal fixation element 70 can then be disengaged from the instrument 80, which can be removed from the access device 12. If the marker is not visible above the proximal end of the access device, the fixation element is in not in the proper position and should be repositioned. In an alternate embodiment of the instrument 90, a closure mechanism may be attached to the instrument 90 and the marker may be employed to indicate if the spinal fixation element is fully seated and if closure mechanism is properly inserted.

Once the fixation element 70 is secured in relation to the implants 50, 50', the access devices 12, 212 can be removed from the implants 50, 50', leaving only minimally invasive percutaneous incisions in the patient where each access device 12, 212 was introduced. This is particularly advantageous in that it reduces the amount of trauma caused to the patient, and it minimizes the damage to muscle surrounding the surgical site.

Figure 24:
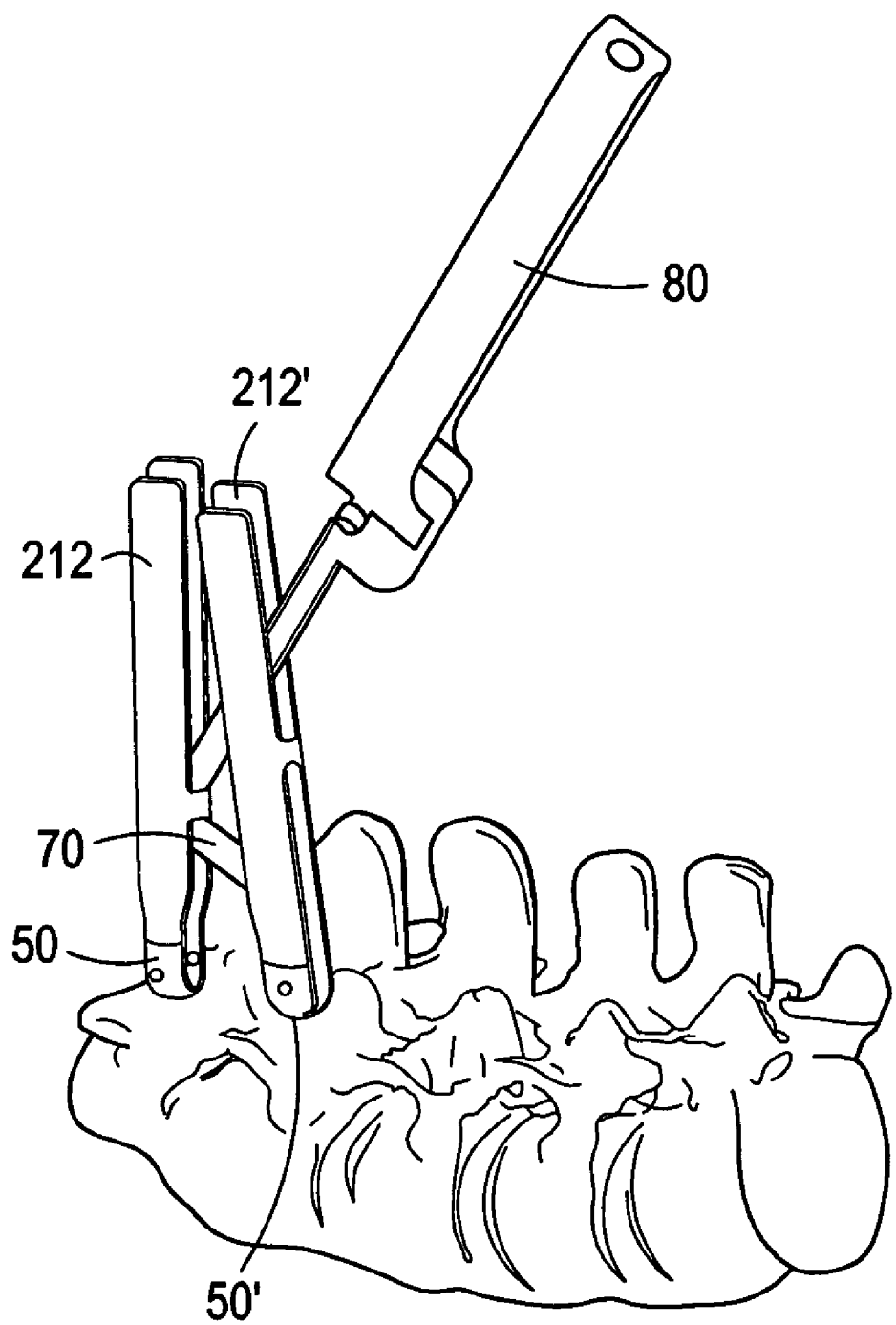
Figure 25:
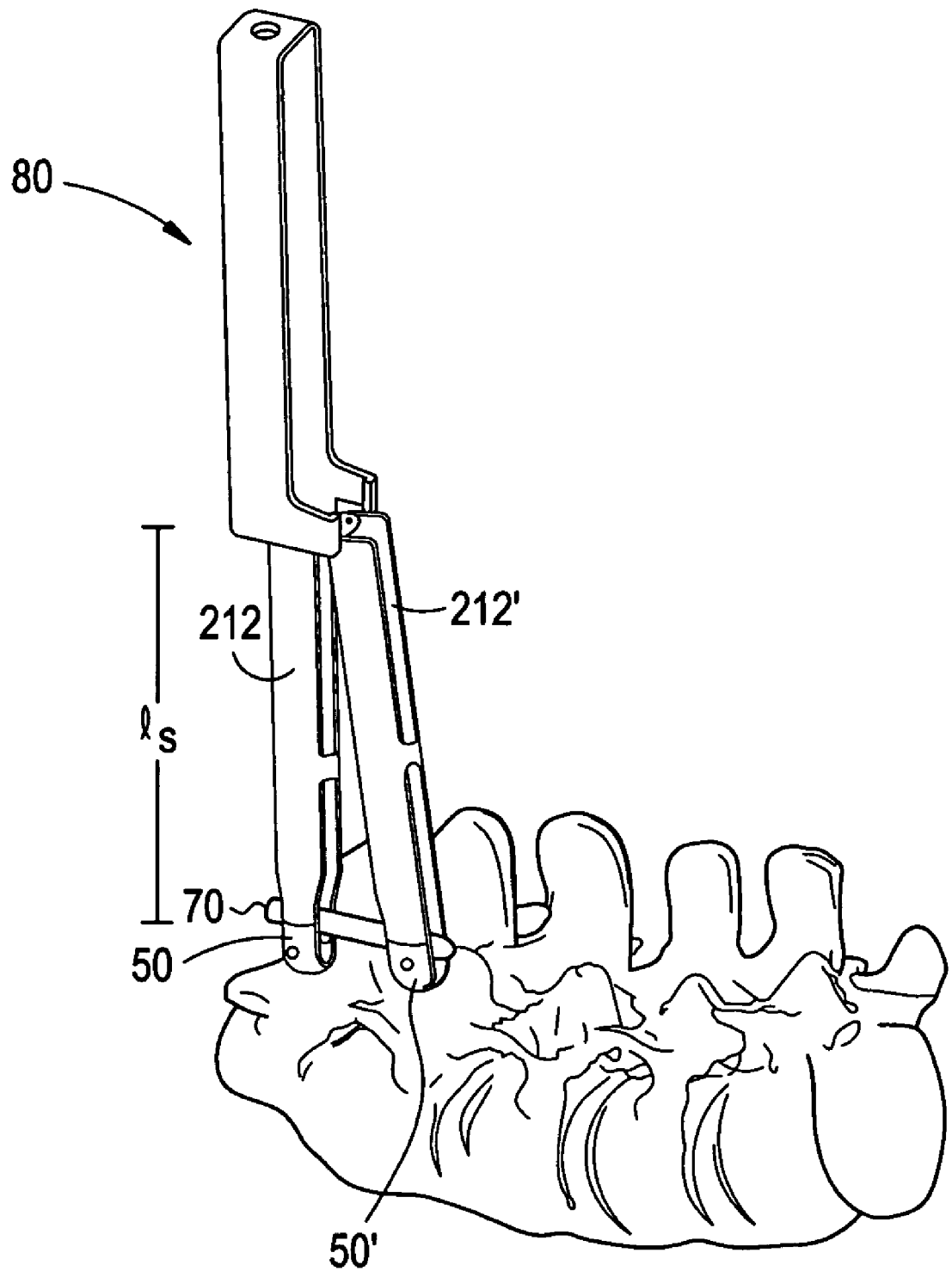

An alternative embodiment of delivering a spinal fixation element, spinal rod 70 to a first bone anchor 50 and a second bone anchor 50' is illustrated in FIGS. 20-25. In the illustrated embodiment, a first percutaneous access device 212 (FIG. 3) and a second percutaneous access device 212' are connected to a first bone anchor 50 and a second bone anchor 50'. An instrument 80 is connected to the spinal rod 80 (FIG. 20) and may be employed to position the spinal rod 70 in the proximal side wall openings 14b of the first and a second percutaneous access devices 212, 212' (FIGS. 21-23) and to manipulate the spinal rod 70 into proximity to the first bone anchor 50 and the second bone anchor 50' (FIGS. 24-25).

Figure 26:
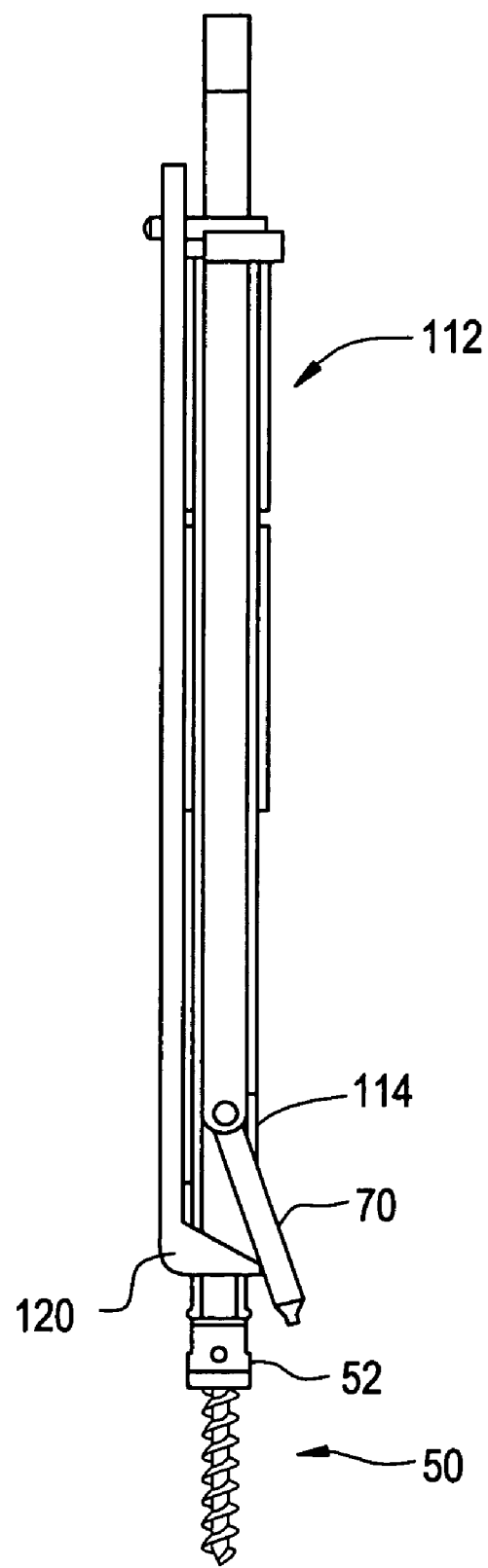
FIGS. 26-28 illustrate a method of inserting a spinal fixation element through the percutaneous access devices shown in FIGS. 6A-6B.
Figure 27:
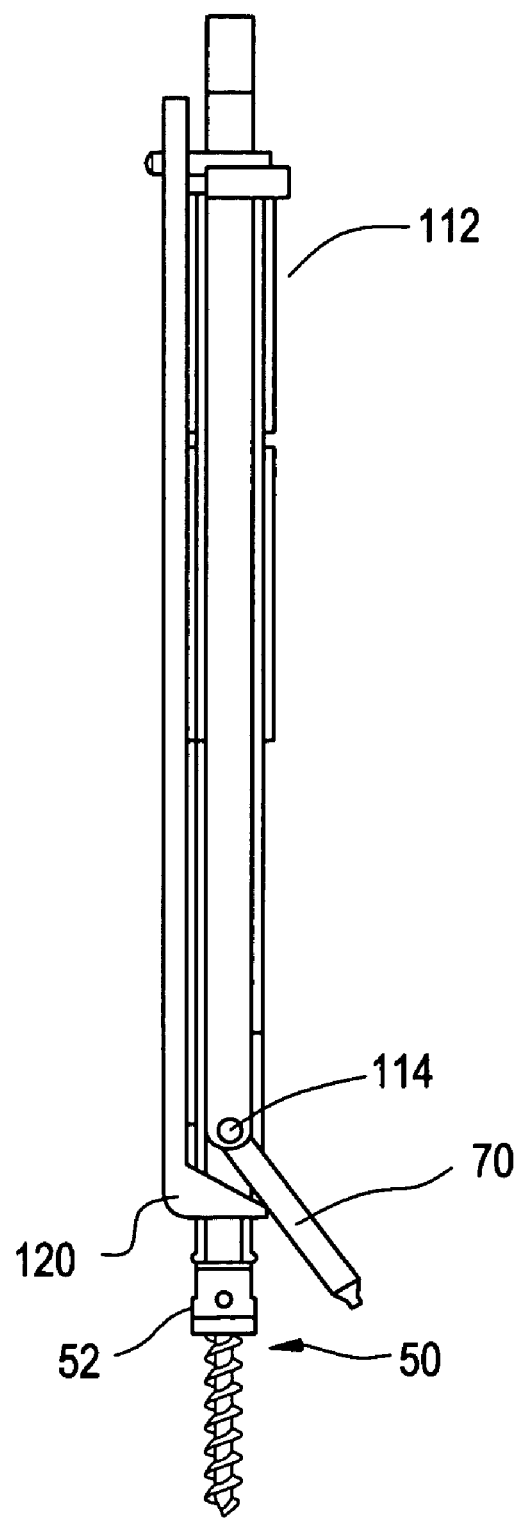
Figure 28:
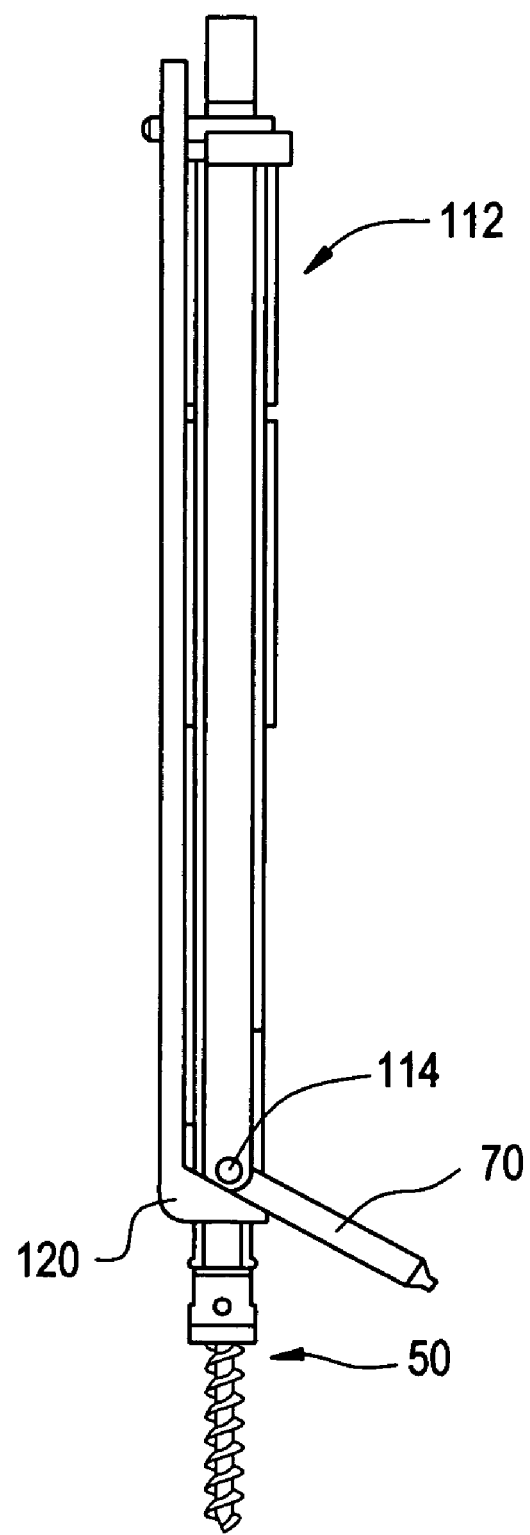

In another embodiment, the percutaneous access device 112 shown in FIGS. 5-6B can be used to facilitate introduction of a spinal fixation element into a surgical anchor site. As previously stated, access device 112 includes a guide member 120 to direct the spinal fixation element 70 from the first orientation to the second orientation. This is illustrated in FIGS. 26-28. As shown, as the spinal fixation element 70 is moved distally to come into contact with the guide member 120, the guide member 120 causes the spinal fixation element 70 to rotate and extend toward the opening 114 in the percutaneous access device 112. As a result, the spinal fixation element 70 is directed into the second orientation, whereby it can be positioned in or adjacent to the receiver heads 52, 52' of the adjacent spinal implants 50, 50'. The guide member 120 can be adjusted along the longitudinal axis of the access device to position the guide at the desired location to contact the spinal fixation element and begin changing its orientation.

As previously stated, a person skilled in the art will appreciate that the exemplary methods described herein can be performed in any sequence using some or any of the steps. Moreover, the percutaneous access devices, instruments, and methods described can be used in any combination to deliver multiple spinal fixation elements simultaneously or sequentially, and/or to perform a variety of other surgical procedures not illustrated or described herein.

Figure 47A:
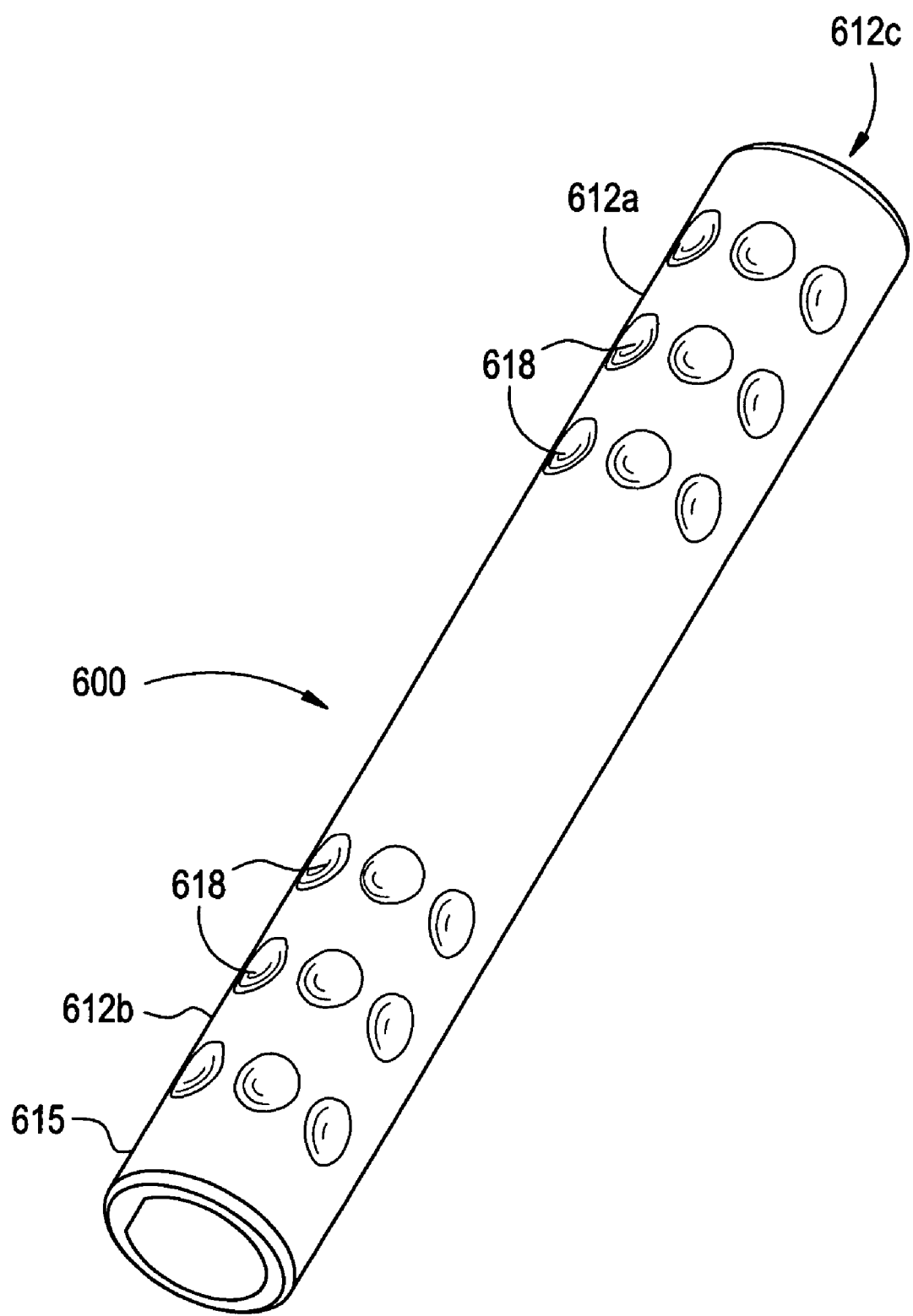
FIG. 47A is a perspective view of an exemplary embodiment of a sleeve for use with a percutaneous access device to facilitate manipulation of the percutaneous access device.
Figure 47B:
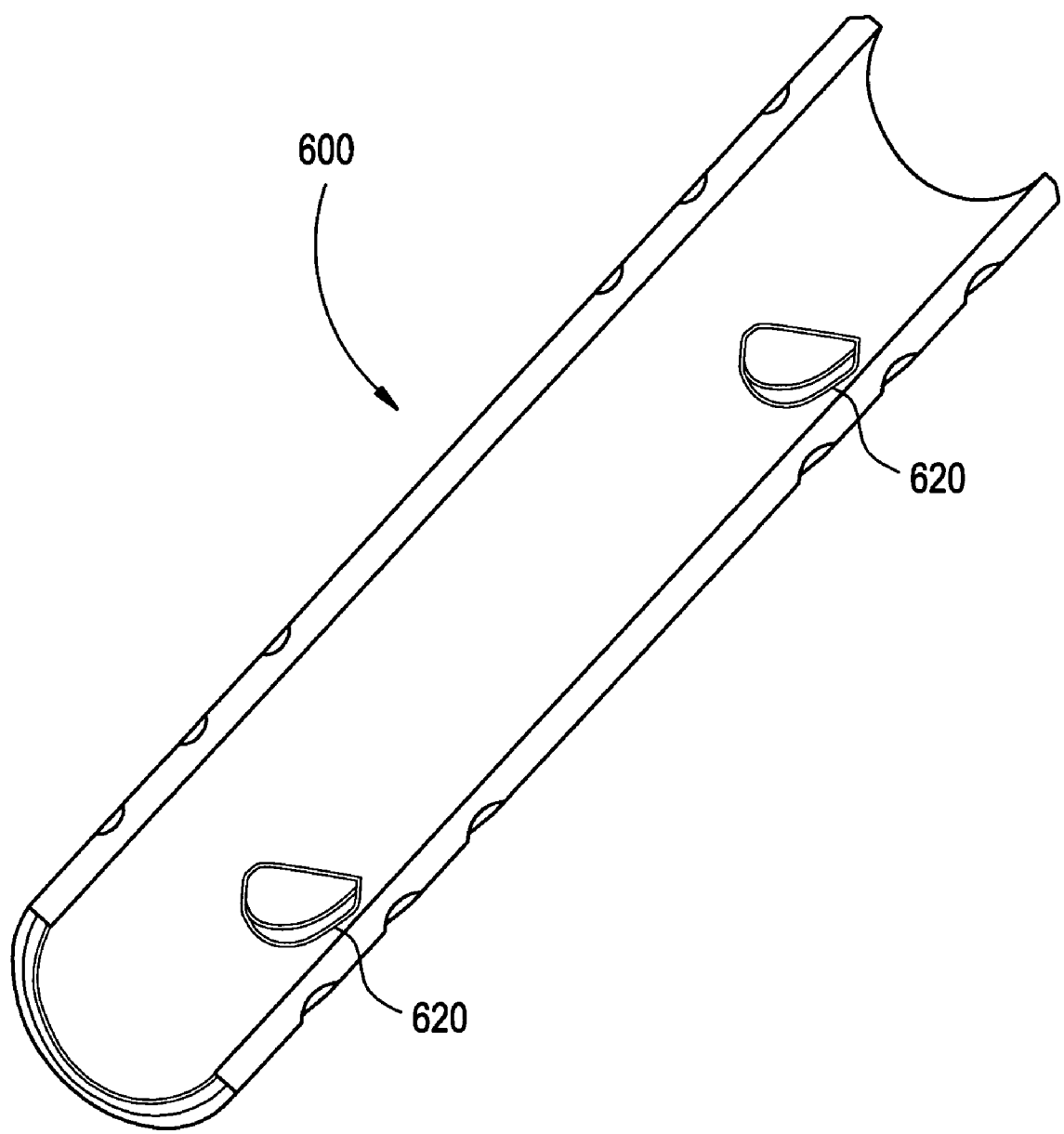
FIG. 47B is a cut away view of the sleeve of FIG. 47A.
Figure 47C:
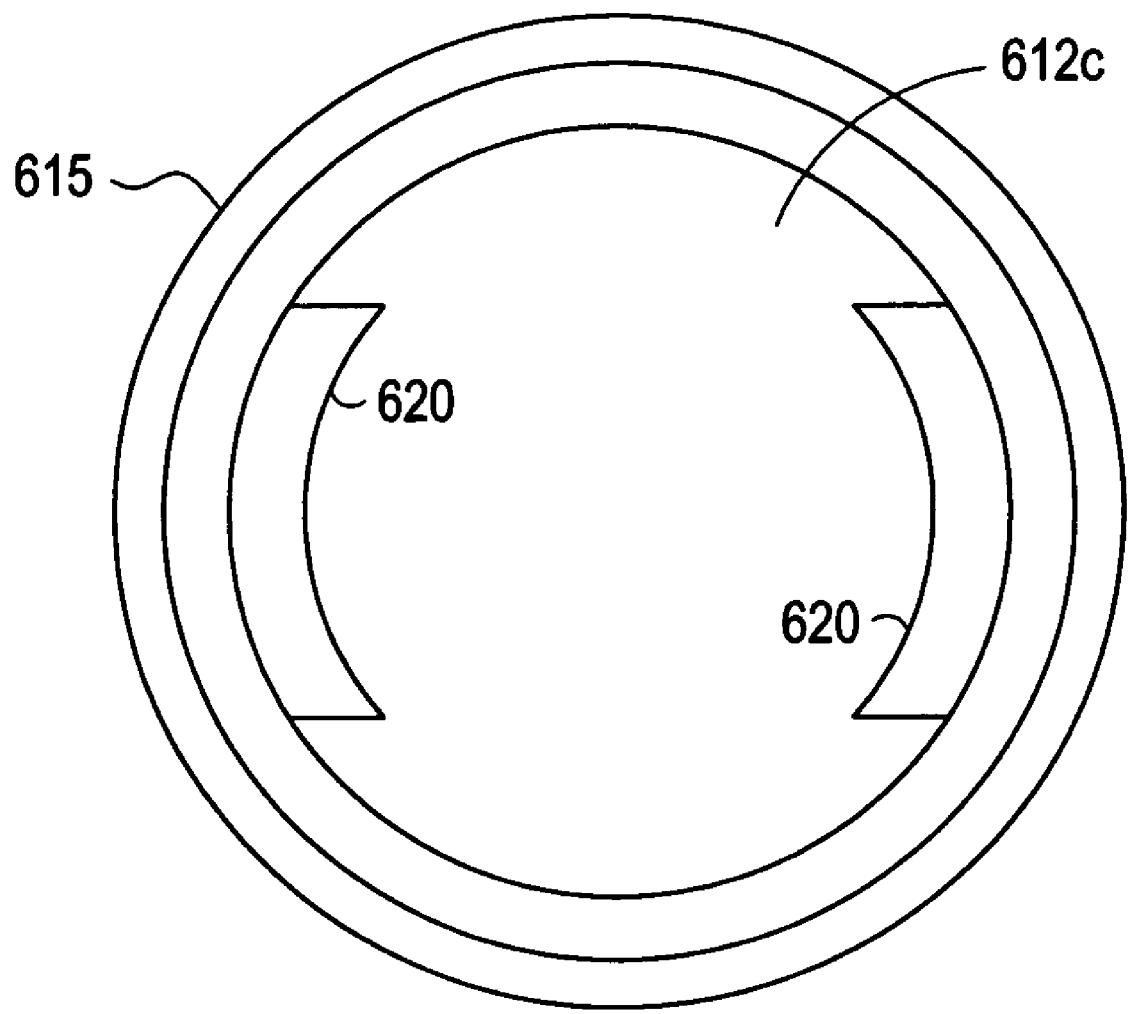
FIG. 47C is an end view of the sleeve of FIG. 47A.
Figure 48:
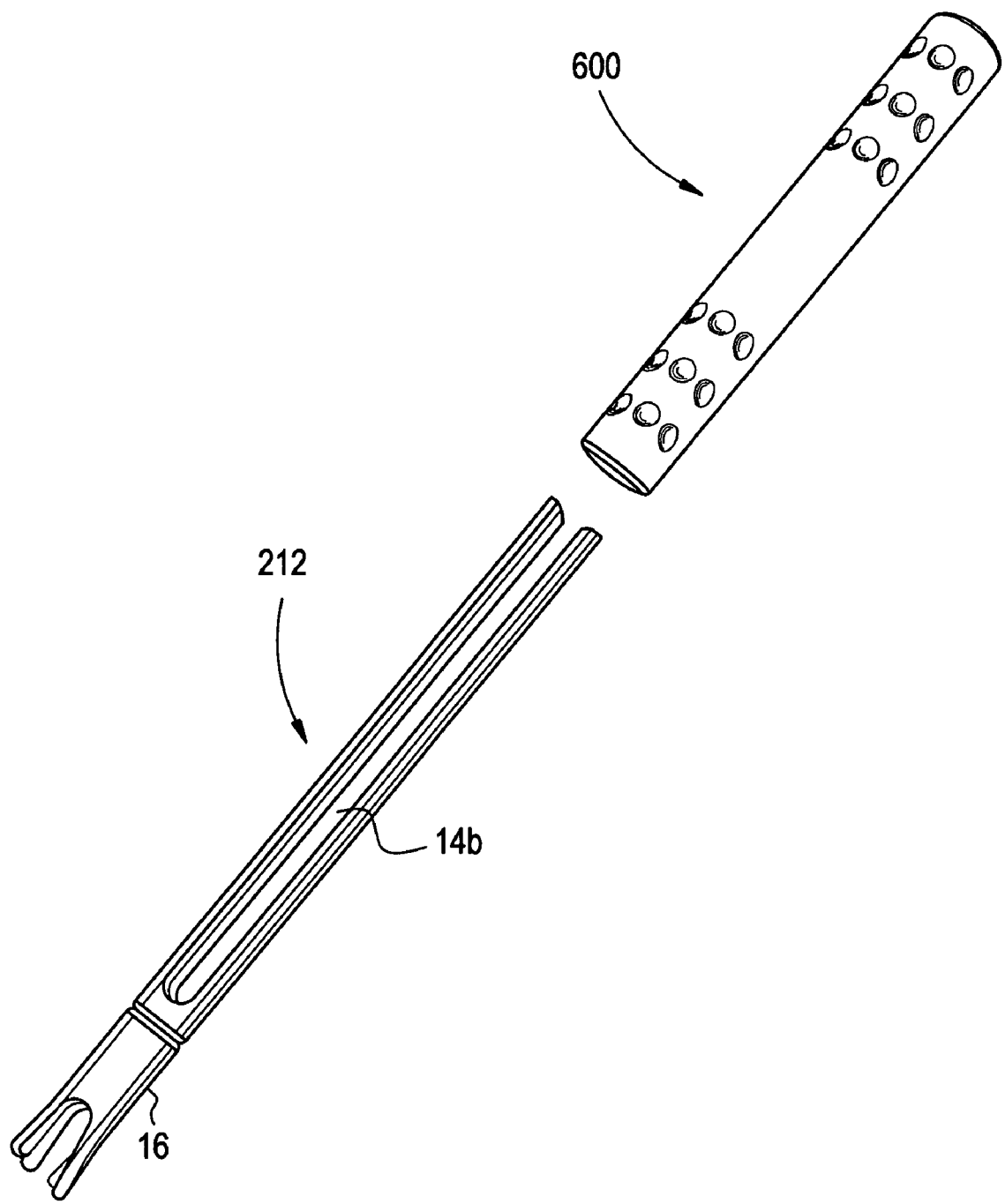
FIG. 48 is a perspective view of the sleeve of FIG. 47A, illustrating the sleeve being positioned over a percutaneous access device.

FIGS. 47A-48 illustrate an instrument 600 for aiding in the insertion and manipulation of a percutaneous access device, such one of the exemplary percutaneous access devices described above. The instrument 600, as discussed below, is particularly suited to facilitate the delivery and manipulation of a percutaneous device having one or more sidewall openings, such as the exemplary percutaneous access device illustrated in FIG. 3. The instrument 600 is in the form of a cylindrically-shaped sleeve having a proximal end 612a, a distal end 612b, and an inner lumen 612c formed therein that extends between proximal and distal ends 612a, 612b. The length of the instrument 600 may vary depending on, for example, the length of the percutaneous access device. In the illustrated exemplary embodiment, for example, the instrument 600 is approximately equal to or less than the length of the percutaneous access device 212. The distal end 612b of the instrument 600 may have a chamfer 615 to ease insertion. The outer surface of the instrument 600 may have surface features to facilitate gripping of the instrument 600. For example, in the illustrated exemplary embodiment, the outer surface of the instrument 600 includes a plurality of dimples 618 arranged about the circumference of the instrument 600 proximate the distal end 612b and the proximal end 612a. The inner surface of the instrument 600, which defines the lumen 612c, may have one or more projections extending inwardly therefrom to engage a sidewall opening in the percutaneous access device and inhibit rotation of the instrument 600 relative to the percutaneous access device. In the illustrated exemplary embodiment, for example, in the inner surface of the instrument includes a pair of projections 620 proximate the distal end 612b and a pair of projections 620 at the proximal end 612. The projections 620 are each sized to fit within a sidewall opening of a percutaneous access device, for example, the sidewall openings 14b of the percutaneous access device 212, as illustrated in FIG. 48. In the illustrated embodiment, each projection 620 in a pair of projections is positioned diametrically opposite the other projection 620 in the pair. In use, the instrument 600 provides rigidity to the percutaneous access device to aid in insertion of the percutaneous access device and bone anchor assembly. Moreover, the instrument 200 may be employed after insertion to facilitate manipulation of the percutaneous access device. For example, the instrument 600 may be used to provide countertorque and/or for compression or distraction of the bone anchors. The instrument 600 may be removed prior to insertion of the spinal fixation element.

Figure 44A:
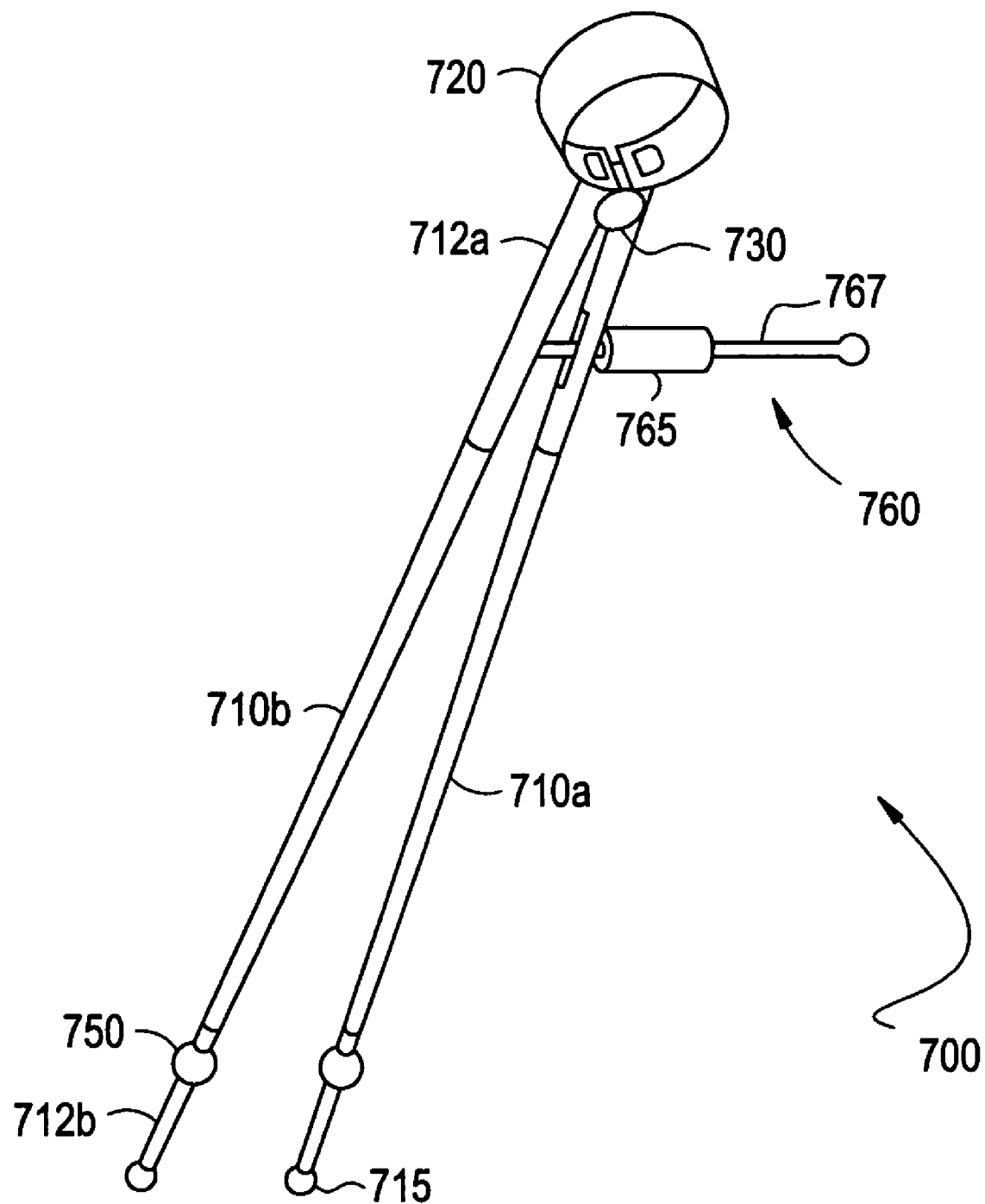
FIGS. 44A and 44B are perspective views of exemplary embodiments of an instrument for determining the distance between two bone anchors.
Figure 44B:
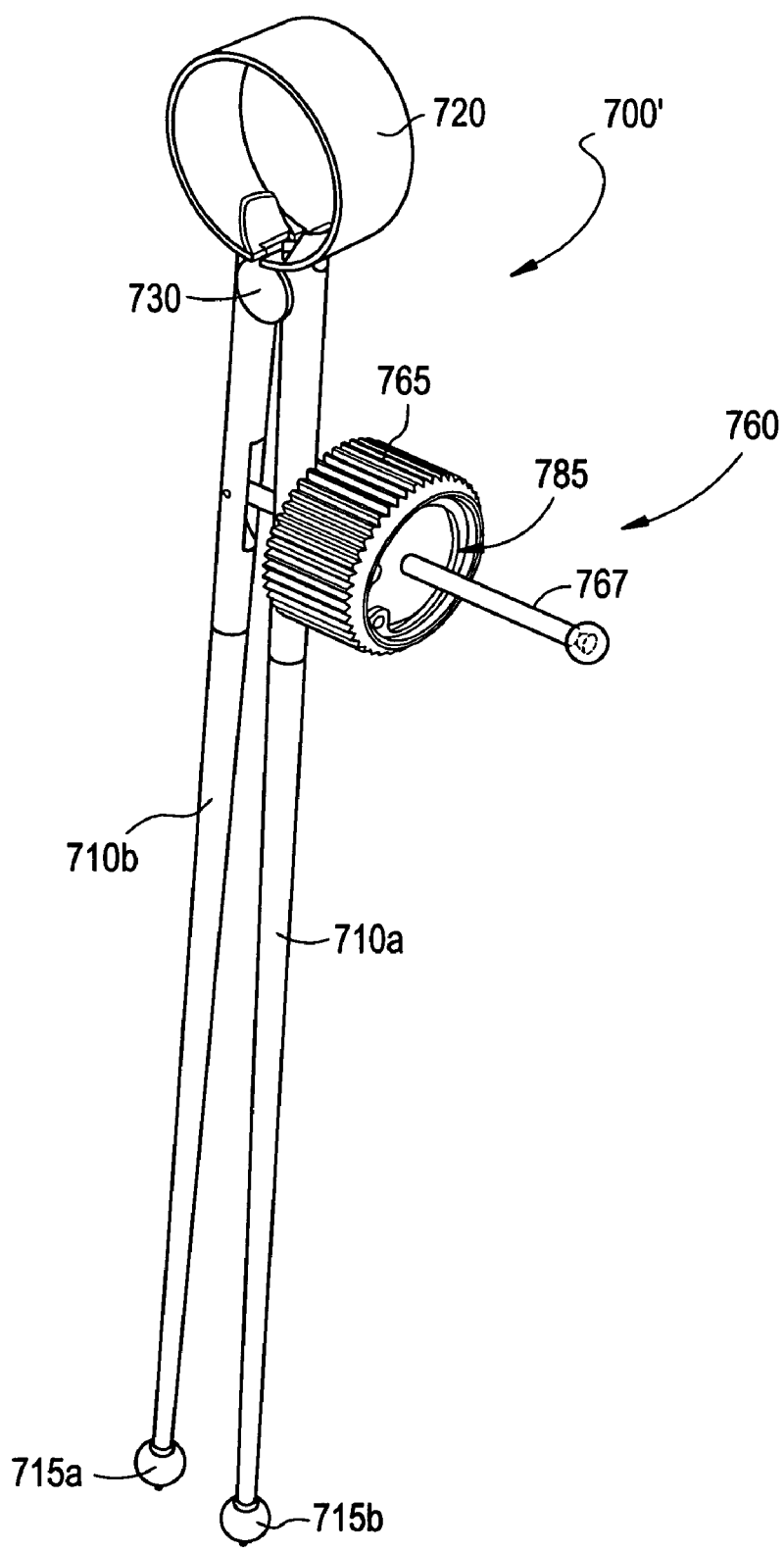
Figure 45:
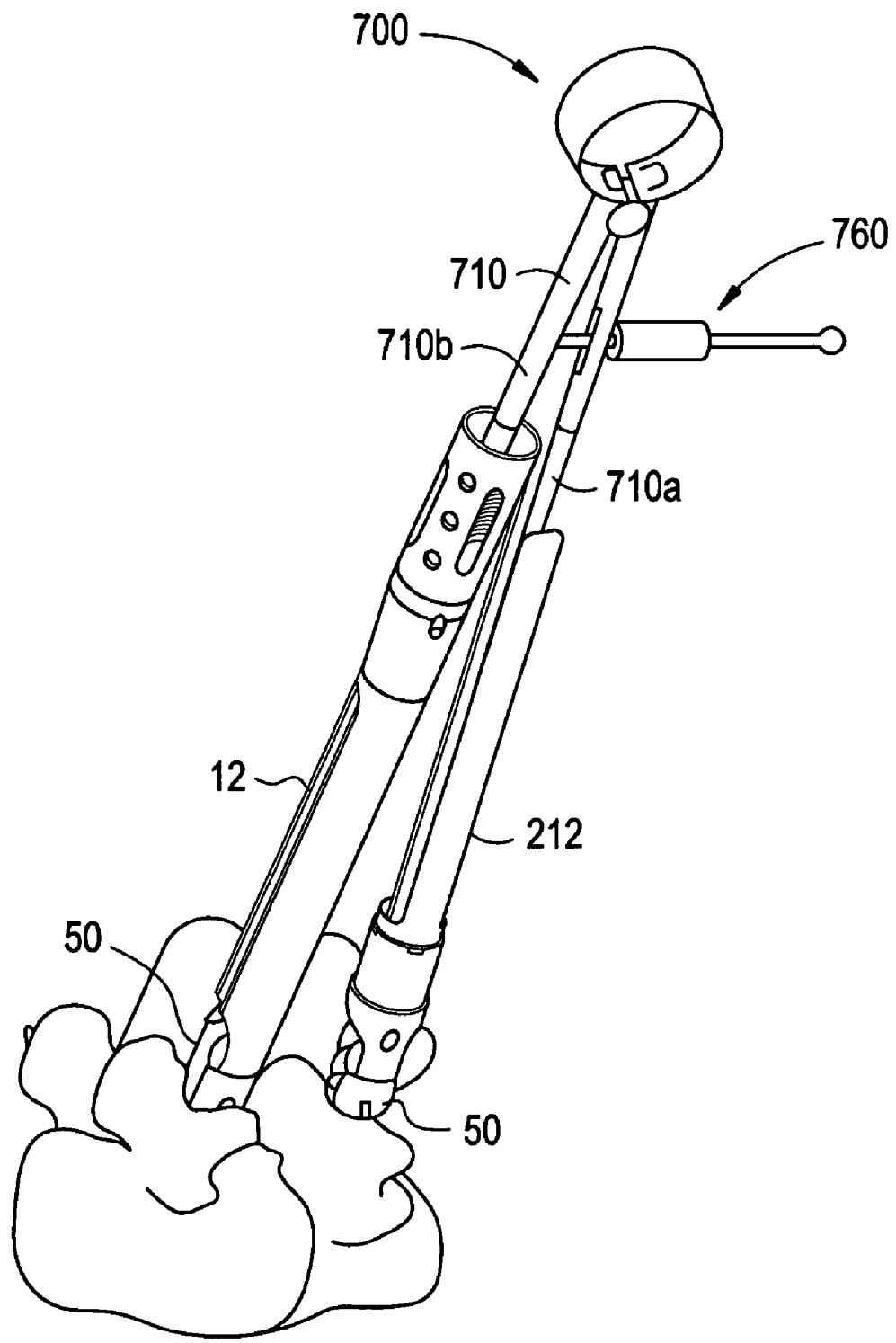
FIG. 45 is a perspective view of the instrument of FIG. 44A, illustrating the instrument inserted through two percutaneous access devices.

To facilitate insertion of the spinal fixation element having the proper length, a measuring instrument 700 may be used to determine the length of the spinal fixation element for insertion between two bone anchors. The measuring instrument 700, in the illustrated exemplary embodiment, may have a first arm 710a and second arm 710b that are connected proximate the proximate end 712a of the measuring instrument 700. In the illustrated exemplary embodiment, the two arms 710a, 710b pivot around a pivot point 730 relative to one another. The first arm 710a and the second arm 710b may be connected by a spring 720 that biases the arms 710 away from each other. In the illustrated embodiment, each arm 710 may have a generally cylindrical shape and may tapers along the length from a first diameter at the proximal end 712a to a second, reduced diameter at the distal end 712b. In the illustrated exemplary embodiment, the diameter of each arm 710 may be less than the inner diameter of a percutaneous access device to permit the arm 710 to be inserted through the percutaneous access device, distally, into proximity with a bone anchor connected to the percutaneous access device and engaged to a vertebra. The distal end 712b of each arm 710 may have a spherical tip 715 having a size analogous to a size of a spinal fixation element to facilitate placement of the spherical tip 715 into a bone anchor, for example into the receiver head of the bone anchor. A centering ball 750 may be located along each arm 710 near the distal end 712b to center the arm 710 within the percutaneous access device and facilitate proper measurement of the distance between distal ends of the arms 710a,b, and thus, the distance between the bone anchors. The measuring instrument may include a locking system 760 to fix the position of the first arm 710a relative to the second arm 710b and, thus, permit the distance between the distal ends of the arms 710a, b to be fixed during a measurement. In the illustrated exemplary embodiment, the locking system 760 may include a threaded rod 767 that intersects the first arm 710a and the second arm 710b and an internally threaded knob 765 that engages the external threads on the rod 767 and is adjustable along the length of the rod 767. The knob 765 may be advanced along the rod 767 into contact with the second arm 710b to fix the position of the second arm 710b relative to the first arm 710a. In an alternative embodiment illustrated in FIG. 44B, a measuring instrument 700' may have a locking system 760 that includes a slip friction clutch 785 to inhibit over tightening of the knob 765 against the second arm 710b.

Figure 46:
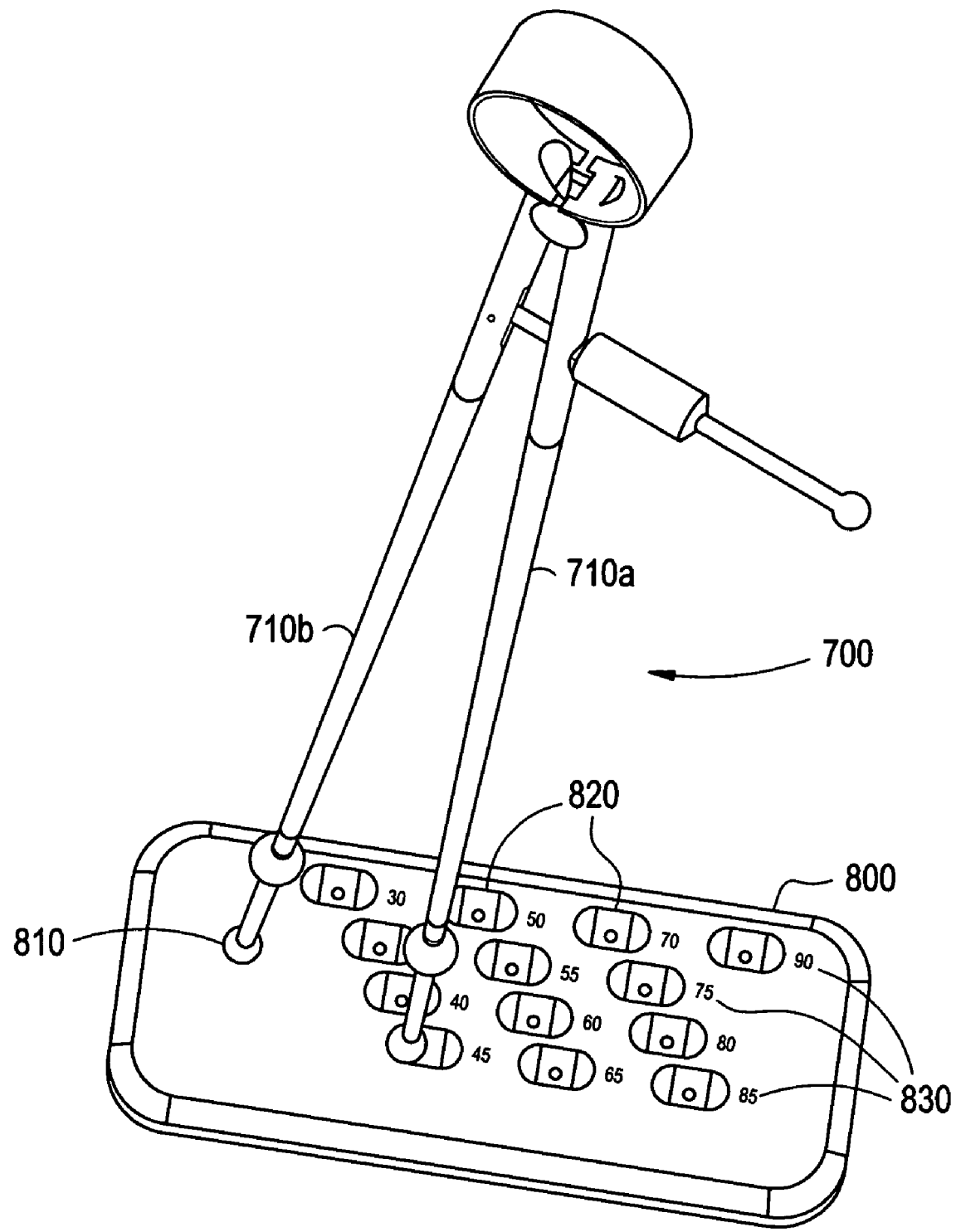
FIG. 46 is a perspective view of the instrument of FIG. 44A, illustrating the instrument positioned within a template block.

In operation, the first arm 710a of the measuring instrument 700 may be inserted through a first percutaneous access device 212 into proximity to a first bone anchor 50 connected to the first percutaneous access 212 and a first vertebra. The second arm 710b of the measuring instrument 700 may be inserted through a second percutaneous access device 12 into proximity to a second bone anchor 50 connected to the second percutaneous access 212 and a second vertebra. In the illustrated exemplary embodiment, the spherical tip 715 of each arm is advanced into contact with the receiver head of the bone anchor. The arms 710a and 710b may be fixed relative to one another using, for example, the locking system 760. The arms 710a and 710b may be removed from the percutaneous access devices 212, 12 to determine the distance between the distal ends 712b of the arms 710a, 710b. For example, a template block 800 may be employed to facilitate measurement of the distance between the distal ends 712b of the arms 710a, 710b, as illustrated in FIG. 46. The exemplary template block 800 may include a plurality of openings, markings, or other reference points that are spaced apart a predetermined distance. For example, the template block 800 may include a first opening 810 for receiving the distal end of one of the arms 710 and a plurality of additional openings 820 that spaced apart predetermined distances from the first opening 810. The template block 800 may include indicia 830 proximate the plurality of second openings that is indicative of the distance between the first opening 810 and one or more of the second openings 820. A fixation element may be selected based upon the distance measured between the distal ends 712b of the arms 710a, 710b.

In alternative exemplary embodiments, the measuring instrument 700 may include a scale or other device mounted to the instrument to facilitate measuring the distance between the distal ends 712b of the arms 710a, 710b without necessitating removal of the arms 710 from the percutaneous access devices or without necessitating a locking system to facilitate fixing the position of the arms relative to one another.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A method for introducing a spinal fixation element into a patient's spinal column, comprising:
providing a first percutaneous access devices, the first percutaneous access device having
a proximal end positioned outside a patient's body,
a distal end adapted to couple to a spinal anchor,
a lumen extending between the proximal and distal ends of the first percutaneous access device and defining a longitudinal axis, and
first and second opposed sidewall openings extending from the distal end through at least a portion of the first percutaneous access device, the first and second opposed sidewall openings communicating with the lumen;
providing a second percutaneous access devices, the second percutaneous access device having a proximal end positioned outside a patient's body, a distal end adapted to couple to a spinal anchor, a lumen extending between the proximal and distal ends of the second percutaneous access device and defining a longitudinal axis, and at least one sidewall opening extending from the distal end through at least a portion of the second percutaneous access device and communicating with the lumen;

engaging a spinal fixation element to a shaft of a manipulator instrument;

wherein the first percutaneous access device has a sleeve disposed therearound and effective to prevent removal of the first percutaneous device from the spinal anchor coupled thereto, the sleeve including at least one sidewall opening formed therein that is adapted to align with the first sidewall opening in the first percutaneous access device;

positioning the shaft of the manipulator instrument through the first and second sidewall opening of the first percutaneous access device, through the at least one sidewall opening of the sleeve, and through the at least one sidewall opening of the second percutaneous access device with the spinal fixation element extends in an orientation substantially parallel to the longitudinal axis of each percutaneous access device; and rotating the manipulator instrument to change the orientation of the spinal fixation element to a substantially transverse orientation to seat the spinal fixation element in the two spinal anchors, the spinal fixation element rotating through the first sidewall opening of the first percutaneous access device into the lumen of the first percutaneous access device during rotation of the manipulator instrument.

2. The method of claim 1, wherein the second percutaneous access device includes first and second opposed sidewall openings.

3. The method of claim 2, wherein one of the percutaneous access devices includes a third and fourth opposed sidewall openings.

4. The method of claim 2, wherein both of the percutaneous access devices include a third and fourth opposed sidewall openings.

5. The method of claim 1, wherein the first sidewall opening extends from the distal end and terminates at a position distal to the proximal end.

6. The method of claim 1, wherein each percutaneous access device is threadably coupled to a receiver head of each spinal anchor.

7. The method of claim 1 wherein each percutaneous access device and spinal anchor are mated together by a twist-lock closure mechanism.

8. The method of claim 1, wherein the first percutaneous access device is coupled to a receiver head of a spinal anchor, and the first sidewall opening in the first percutaneous access device is adapted to align with a seating portion formed in each receiver head.

9. The method of claim 1, further comprising delivering a closure mechanism through each percutaneous access device and applying the closure mechanism to each spinal anchor to lock the spinal fixation element to the anchors.

10. The method of claim 1, further comprising compressing or distracting the bone anchors by manipulating the percutaneous access devices.

11. The method of claim 1, further comprising implanting the first percutaneous access device through a first minimally invasive incision and implanting the second percutaneous access device through a second minimally invasive incision.

12. The method of claim 1, further comprising
connecting a first bone anchor to the first percutaneous access device;
implanting the first percutaneous access device and the first bone anchor through a first minimally invasive incision;
anchoring the first bone anchor in a first vertebra;
connecting a second bone anchor to the second percutaneous access device;
implanting the second percutaneous access device and the second bone anchor through a second minimally invasive incision;
anchoring the second bone anchor in a second vertebra, wherein the manipulator instrument seats the spinal fixation element in the first and second bone anchors.

* * * * *